United States Patent
Graham et al.

(10) Patent No.: US 9,439,848 B2
(45) Date of Patent: Sep. 13, 2016

(54) COPOLYMERS USEFUL AS RHEOLOGY MODIFIERS AND HOME AND PERSONAL CARE COMPOSITIONS COMPRISING SAID COPOLYMERS

(75) Inventors: Keith Graham, Huddersfield (GB); David Normington, Leeds (GB); Howard R. Dungworth, Brighouse (GB); John M. Plonka, Leeds (GB)

(73) Assignee: BASF SE, Ludwigshafen (DE)

( * ) Notice: Subject to any disclaimer, the term of this patent is extended or adjusted under 35 U.S.C. 154(b) by 511 days.

(21) Appl. No.: 12/548,924

(22) Filed: Aug. 27, 2009

(65) Prior Publication Data

US 2010/0056647 A1 Mar. 4, 2010

Related U.S. Application Data

(60) Provisional application No. 61/190,785, filed on Sep. 2, 2008.

(51) Int. Cl.

| A61K 8/81 | (2006.01) |
|---|---|
| C08F 216/14 | (2006.01) |
| C08F 220/28 | (2006.01) |
| A61K 8/91 | (2006.01) |
| A61Q 5/00 | (2006.01) |
| A61Q 5/02 | (2006.01) |
| A61Q 5/12 | (2006.01) |
| A61Q 19/10 | (2006.01) |
| C08F 2/24 | (2006.01) |
| C08F 220/34 | (2006.01) |
| C11D 3/37 | (2006.01) |
| A61Q 5/06 | (2006.01) |
| C08F 220/06 | (2006.01) |
| C08F 220/18 | (2006.01) |
| C08F 220/56 | (2006.01) |
| C08F 222/10 | (2006.01) |

(52) U.S. Cl.
CPC ............. *A61K 8/91* (2013.01); *A61Q 5/004* (2013.01); *A61Q 5/02* (2013.01); *A61Q 5/12* (2013.01); *A61Q 19/10* (2013.01); *C08F 2/24* (2013.01); *C08F 220/34* (2013.01); *C11D 3/3773* (2013.01); *C11D 3/3788* (2013.01); *A61Q 5/006* (2013.01); *A61Q 5/06* (2013.01); *C08F 220/06* (2013.01); *C08F 220/18* (2013.01); *C08F 220/56* (2013.01); *C08F 222/1006* (2013.01)

(58) Field of Classification Search
None
See application file for complete search history.

(56) References Cited

U.S. PATENT DOCUMENTS

| 3,399,159 A | 8/1968 | Samour |
|---|---|---|
| 4,542,175 A | 9/1985 | Fink et al. |
| 4,892,916 A | 1/1990 | Hawe et al. |
| 4,966,712 A | 10/1990 | Nishibayashi et al. |
| 5,011,978 A | 4/1991 | Barron et al. |
| 5,053,448 A | 10/1991 | Tsaur et al. |
| 5,073,591 A | 12/1991 | Tsaur et al. |
| 5,100,660 A | 3/1992 | Hawe et al. |
| 5,294,692 A | 3/1994 | Barron et al. |
| 5,840,789 A | 11/1998 | Verstrat et al. |
| 5,990,233 A | 11/1999 | Barron et al. |
| 6,025,431 A | 2/2000 | Cardinali et al. |
| 6,271,192 B1 | 8/2001 | Verstrat et al. |
| 6,326,430 B1 | 12/2001 | Berte et al. |
| 6,338,855 B1 * | 1/2002 | Albacarys et al. ........... 424/409 |
| 6,465,416 B2 | 10/2002 | Verstrat et al. |
| 6,667,029 B2 | 12/2003 | Zhong et al. |
| 2004/0052746 A1 | 3/2004 | Tamareselvy et al. |
| 2004/0241130 A1 | 12/2004 | Tamareselvy et al. |
| 2005/0119401 A1 | 6/2005 | Bavouzet et al. |
| 2008/0014160 A1 | 1/2008 | Faivre et al. |
| 2009/0746969 | 3/2009 | Biganska |

FOREIGN PATENT DOCUMENTS

| EP | 2039346 | 3/2009 |
|---|---|---|
| JP | H07-285831 | 10/1995 |
| JP | 2002-322219 | 11/2002 |
| JP | 2006-176641 | 7/2006 |
| WO | 2004024779 | 3/2004 |
| WO | 2005092276 | 10/2005 |
| WO | WO 2007090759 A1 * | 8/2007 |
| WO | 2008036587 | 3/2008 |

OTHER PUBLICATIONS

International Search Report Dated Nov. 4, 2009.

* cited by examiner

*Primary Examiner* — Bethany Barham
*Assistant Examiner* — Peter Anthopolos
(74) *Attorney, Agent, or Firm* — Lowenstein Sandler LLP

(57) ABSTRACT

The present invention relates to aqueous personal care, household care, and/or fabric care compositions comprising the instant copolymers. Also disclosed are methods for the rheological modification of aqueous personal care, household care, and/or fabric care compositions comprising the instant copolymers.

16 Claims, No Drawings

COPOLYMERS USEFUL AS RHEOLOGY MODIFIERS AND HOME AND PERSONAL CARE COMPOSITIONS COMPRISING SAID COPOLYMERS

This application claims the benefit of Provisional Application No. 61/190,786, filed Sep. 2, 2008, herein incorporated entirely by reference.

FIELD OF THE INVENTION

This invention relates to the field of polymers, and in particular, to copolymers and home and personal care compositions comprising said copolymers.

BACKGROUND OF THE INVENTION

Formulations having an acidic pH, (i.e., <7), containing cationic components, such as cationic surfactants and salts thereof or active acidic components are commonly referred to as "low pH" formulations. Stable low pH viscous emulsion and gel formulations are difficult to obtain. Most commonly used thickeners are synthetic associative thickeners that are frequently anionic and hence typically are incompatible with the cationic component, especially quaternary ammonium salts, or are ineffective thickeners at low pH.

Consequently, the formulator of low pH compositions, especially emulsions, has a limited choice of either nonionic thickeners, such as nonionic surfactants, or cationic thickeners. Nonionic thickeners are uncharged and thus are assumed to be less reactive, but nonionics tend to inactivate preservatives and in some cases promote microbial growth. While some cationic polymeric rheology modifiers, such as hydrophobically modified aminoacrylate copolymers, are available commercially, their rheological properties are unpredictable, or aesthetically unsatisfactory.

US 2004/0241130 discloses multi-purpose polymers, methods and compositions, which is incorporated herein by reference.

US 2004/0052746 discloses multi-purpose polymers, methods and compositions, which is incorporated herein by reference.

U.S. Pat. No. 5,073,591 discloses polymeric thickeners and methods of producing the same, which is incorporated herein by reference.

U.S. Pat. No. 5,053,448 discloses polymeric thickeners and method of producing the same, which is incorporated herein by reference.

U.S. Pat. No. 4,892,916 discloses polymeric thickeners and their production, which is incorporated herein by reference.

U.S. Pat. No. 5,100,660 discloses thickened acidic aqueous compositions using cationic polymers, which is incorporated herein by reference.

US 2005/0119401 discloses the use of charged amphiphilic statistic polymers for thickening aqueous compositions, which is incorporated herein by reference.

U.S. Pat. No. 6,667,029 discloses stable, aqueous cationic hydrogels, which is incorporated herein by reference.

U.S. Pat. No. 4,542,175 discloses a method for thickening aqueous systems, which is incorporated herein by reference.

U.S. Pat. No. 6,326,430 discloses thickening agents for acidic aqueous compositions, which is incorporated herein by reference.

U.S. Pat. No. 6,271,192 discloses an associative thickener for aqueous fabric softener, which is incorporated herein by reference.

U.S. Pat. No. 5,011,978 discloses copolymers as thickeners and modifiers for latex systems, which is incorporated herein by reference.

U.S. Pat. No. 3,399,159 discloses cationic lattices and methods of preparing the same, which is incorporated herein by reference.

U.S. Pat. No. 5,990,233 discloses rheology modifiers for use in aqueous systems, which is incorporated herein by reference.

U.S. Pat. No. 5,840,789 discloses aqueous compositions thickened with acrylate-based polymeric rheology modifiers, which is incorporated herein by reference.

U.S. Pat. No. 6,465,416 discloses associative thickeners for aqueous fabric softener, which is incorporated herein by reference.

U.S. Pat. No. 6,025,431 discloses thickened personal care compositions, which is incorporated herein by reference.

Thus, there is an ongoing need and desire for a cationic compatible polymeric rheology modifier for low pH formulations.

SUMMARY OF THE INVENTION

The present invention provides multi-purpose copolymers, which have generally cationic and associative characteristics.

The copolymers of the present invention are multifunctional vinyl addition polymers having a combination of amino substituents that provide hydrophilicity and cationic properties at low pH, hydrophobic substituents to attenuate the hydrophilicity, hydrophobically modified polyoxyalkylene substituents that provide associative properties, and hydrophilic polyoxyalkylene substituents that attenuate the associative properties and provide beneficial rheological properties. The polymers are produced by polymerization of a monomer mixture comprising at least one amino-substituted vinyl monomer; at least one hydrophobic nonionic vinyl monomer; at least one associative vinyl monomer; and, optionally, comprising one or more hydroxy-substituted nonionic vinyl monomer, crosslinking monomer, chain transfer agent, polymeric stabilizer, and the like.

The polymers can swell upon acidification with either inorganic acid or organic acid, including amino acid, or upon alkylation, or by both acidification and alkylation. The inventive, multi-purpose copolymers can be employed as thickeners, emulsifiers, stabilizers, suspending agents, film formers, conditioners, moisturizers, spreading aids and carriers for enhancing the efficacy, deposition or delivery of chemically and physiologically active ingredients and cosmetic materials, and as vehicles for improving the psychosensory, and aesthetic properties of a formulation in which they are included. The cationic character of the copolymers at low pH makes them useful as antistatic agents, and, under certain conditions, may also provide biocidal, anti-microbial, or other preservative activity.

The copolymers of the instant invention beneficially can thicken acidic aqueous formulations to provide aesthetically smooth-textured products that flow smoothly and spread easily. The form of the copolymer containing product can range from a non-pourable, stiff to soft gel, a semisolid paste to a substantially solid stick or bar, and aerosolized foam to squeezable gel, as well as a non-runny, yet flowable, product, suitable for pumpable spray or roll-on products and liquid lotions. The inventive copolymers are surprisingly effective at thickening aqueous systems containing cationic ingredients (e.g., quaternary ammonium compounds and amines), cationic conditioning agents, fabric softeners, surfactants, and the like.

In another embodiment, the invention relates to the incorporation of a basic material to the previously acid thickened cationic copolymeric compositions to increase the pH of the composition without negatively impacting the viscosity, rheology and turbidity of the composition.

Advantageously, the copolymers of this invention can be employed, without being limited thereto, in personal care compositions and products, health care compositions and products, household care compositions and products, fabric care compositions and products, institutional and industrial (collectively "I&I") care products, and the like. The copolymers can be employed as a film forming conditioner, and for promoting the deposition of color cosmetics and of polar and non-polar oils on skin, hair, or both. Further, the copolymers can be employed in products for industrial chemical processes, textile finishing processes, printing, adhesive coating, and like applications as, for example, rheology modifiers, emulsifiers, stabilizers, solubilizers, suspending agents, flocculants, and pigment and grinding additives.

DETAILED DESCRIPTION OF THE INVENTION

The copolymers of the present invention are generally basic, aqueous acid-swellable, or aqueous acid-soluble, copolymers, and salts thereof, which contain at least one basic amino substituent that is cationic at low pH, two or more hydrophobically modified polyoxyalkylene substituent derived from an associative vinyl monomer. The copolymer of the present invention can also optionally contain substituent groups derived from other monomer units, such as crosslinking monomer units, hydroxy-substituted nonionic vinyl monomer units, chain transfer agent units, polymeric stabilizers, and the like. The copolymers of the present invention generally exhibit associative properties in aqueous solution.

The term "low pH formulation" refers to formulations having an acidic pH in the range of about 0.5 to not more than about 7, preferably to not more than about 6.5. For example, the pH may range from about 0.5 to about 3, 4, 5 or 6.

The term "aqueous" as applied to formulations or media means that water is present in an amount sufficient to at least swell or dissolve the copolymer in the composition into which it is included.

It has been surprisingly discovered that the instant copolymers provide desirable rheological properties to low pH aqueous personal care, health care, household care, fabric care, industrial and institutional care products. The inventive copolymers are cationic compatible making them particularly useful as thickeners in products containing quaternary ammonium salts or amines. The instant copolymers are useful thickeners in products containing active acid components and are useful thickeners and emulsifiers for emulsions (creams, lotions). In addition to thickening, the instant copolymers are useful film formers, spreading aids and deposition aids for products containing colorants and emollient oils. Surprisingly, the instant copolymers are useful in compositions containing a relatively high concentration (e.g. 10-40%) of anionic surfactant, and also provide hair setting efficacy.

The term "personal care compositions and/or products" as used herein includes, without being limited thereto, cosmetics, toiletries, cosmeceuticals and beauty aids, personal hygiene and cleansing products applied to the skin, hair, scalp, and nails of humans and animals. The term "health care compositions and/or products" as used herein includes, without being limited thereto, pharmaceuticals, pharmacosmetics, oral care products (mouth, teeth), eye care products, ear care products and over-the-counter products and appliances, such as patches, plasters, dressings and the like, and medical devices externally applied to or into the body of humans and animals for ameliorating a health-related or medical condition, for generally maintaining hygiene or well-being, and the like. The term "body" includes the keratinous (hair, nails) and non-keratinous skin areas of the entire body (face, trunk, limbs, hands and feet), the tissues of body openings and eyes, and the term "skin" includes the scalp and mucous membranes. The term "household care products and/or compositions" or "home care products or compositions" as used herein includes, without being limited thereto, products employed in a domestic household for surface cleaning or biocidal cleaning products for maintaining sanitary conditions, such as in the kitchen and bathroom, and laundry products for fabric care and cleaning, and the like. The term "institutional and industrial care" and "I&I", as used herein includes, without being limited thereto, products employed for cleaning or maintaining sanitary conditions in industrial and institutional environments, including hospital and health care facilities, and the like.

The inventive copolymers of the present invention are multi-purpose copolymers, which are preferably prepared by polymerizing a monomer mixture containing: at least one basic, amino-substituted vinyl monomer or salt thereof; at least one hydrophobic nonionic vinyl monomer; at least one associative vinyl monomer; and, optionally one or more hydroxy-substituted nonionic vinyl or crosslinking monomer. The inventive copolymers of the present invention can also be prepared from monomer mixtures containing chain transfer agents (CTA) or other functional components commonly utilized in emulsion polymers and emulsion polymerization processes.

The inventive copolymers of the present invention are the copolymers described in formulae (I) and (II)

 (I)

wherein a, b, c, and d represent the percentage by weight that each repeating unit or derived monomer is contained within the copolymer;

a, b, c, and d add up to total substantially 100 weight percent relative to the total weight of the copolymer;

a is from about 81 to about 99.8% by weight of the copolymer;

b is from about 0.1% to about 18.9% by weight of the copolymer;

c is from about 0.1% to about 18.9% by weight of the copolymer;

d is from about 0% to about 18.8% by weight of the copolymer;

* is a terminal group, for example, a catalyst residue;

A is an amino-substituted vinyl monomer or salt thereof selected from the group consisting of mono-(C1-C4)alkylamino(C1-C8)alkyl(meth)acrylate, di-(C1-C4)alkylamino (C1-C8)alkyl(meth)acrylate, mono-(C1-C4)alkylamino(C1-C8)alkyl-(meth)acrylamide, di-(C1-C4)alkylamino(C1-C8)alkyl(meth)acrylamide, nitrogen-containing heterocyclic (meth)acrylamide, nitrogen-containing heterocyclic (meth)acrylate, and mixtures thereof.

B is a hydrophobic nonionic vinyl monomer selected from the group consisting of $C_1$-$C_{30}$ alkyl ester of acrylic acid, $C_1$-$C_{30}$ alkyl ester of methacrylic acid, and mixtures thereof;

C is an associative-like monomer of formula (V)

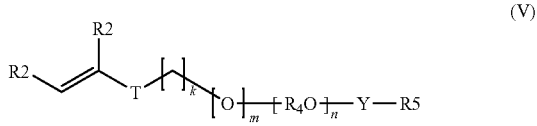

(V)

wherein, each R2 is independently H, methyl, —C(O)OH, or —C(O)OR3; R3 is C1-C30 alkyl; T is —CH$_2$C(O)O—, —C(O)O—, —O—, —CH$_2$O—, —NHC(O)NH—, —C(O)NH—, —Ar—(CE$_2$)z-NHC(O)O—, —Ar—(CE$_2$)z-NHC(—O)NH—, or —CH$_2$CH$_2$NHC(O)—; Ar is a divalent aryl; E is H or methyl; z is 0 or 1; k is an integer in the range of 0 to about 30, and m is 0 or 1, with the proviso that when k is 0, m is 0, and when k is in the range of 1 to about 30, m is 1; (R4-O)n is a polyoxyalkylene, which is a homopolymer, a random copolymer, or a block copolymer of $C_2$-$C_4$ oxyalkylene units, wherein R4 is $C_2H_4$, $C_3H_6$, $C_4H_8$, or a mixture thereof, and n is an integer in the range of about 5 to about 250, preferably about 5 to about 100, more preferably about 10 to about 80, and most preferably about 10 to about 60; Y is —R4O—, —R4NH—, —C(O)—, —C(O)NH—, —R4NHC(O)NH—, or —C(O)NHC(O)—; and R5 is a substituted or unsubstituted alkyl selected from the group consisting of a $C_8$-$C_{40}$ linear alkyl, a $C_8$-$C_{40}$ branched alkyl, a $C_8$-$C_{40}$ carbocyclic alkyl, a $C_2$-$C_{40}$ alkyl-substituted phenyl, an aryl-substituted $C_2$-$C_{40}$ alkyl, and a $C_8$-$C_{80}$ complex ester; wherein the R5 alkyl group optionally comprises one or more substituents selected from the group consisting of a hydroxyl group, an alkoxyl group, and a halogen group; and D is an associative-like vinyl monomer selected from the group consisting of cetyl polyethoxylated methacrylate (CEM), cetearyl polyethoxylated methacrylate (CSEM), stearyl polyethoxylated (meth)acrylate, arachidyl polyethoxylated (meth)acrylate, behenyl polyethoxylated methacrylate (BEM), lauryl polyethoxylated methacrylate (LEM), cerotyl polyethoxylated (meth)acrylate, monthanyl polyethoxylated (meth)acrylate, melissyl polyethoxylated (meth)acrylate, lacceryl polyethoxylated (meth) acrylate, tristyryl phenolpolyethoxylated methacrylate (TEM), hydrogenated castor oil polyethoxylated methacrylate (HCOEM), canola polyethoxylated (meth)acrylate, and cholesterol polyethoxylated methacrylate (CHEM), A, B, C, and D, when present, are covalently attached to each other;

with the proviso that when both C and D are present in the copolymer, C and D are not the same;

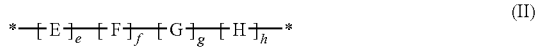

(II)

wherein e, f, g, and h represent the percentage by weight that each repeating unit or derived monomer is contained within the copolymer;

e, f, g, and h add up to total substantially 100 weight percent relative to the total weight of the copolymer;

e is from about 5% to about 99.6% by weight of the copolymer;

f is from about 5% to about 99.6% by weight of the copolymer;

g is from about 0.1% to about 40% by weight of the copolymer;

h is from about 0.1% to about 40% by weight of the copolymer;

* is a terminal group, for example, a catalyst residue;

E is an amino-substituted vinyl monomer or salt thereof selected from the group consisting of mono-(C1-C4)alkylamino(C1-C8)alkyl(meth)acrylate, di-(C1-C4)alkylamino(C1-C8)alkyl(meth)acrylate, mono-(C1-C4)alkylamino(C1-C8)alkyl-(meth)acrylamide, di-(C1-C4)alkylamino(C1-C8)alkyl(meth)acrylamide, nitrogen-containing heterocyclic (meth)acrylamide, nitrogen-containing heterocyclic (meth)acrylate, and mixtures thereof.

F is a hydrophobic nonionic vinyl monomer selected from the group consisting of $C_1$-$C_{30}$ alkyl ester of acrylic acid, $C_1$-$C_{30}$ alkyl ester of methacrylic acid, and mixtures thereof;

G is an associative-like monomer of formula (V)

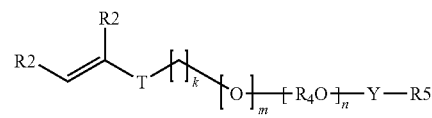

(V)

wherein, each R2 is independently H, methyl, —C(O)OH, or —C(O)OR3; R3 is C1-C30 alkyl; T is —CH$_2$C(O)O—, —C(O)O—, —O—, —CH$_2$O—, —NHC(O)NH—, —C(O)NH—, —Ar—(CE$_2$)z-NHC(O)O—, —Ar—(CE$_2$)z-NHC(—O)NH—, or —CH$_2$CH$_2$NHC(O)—; Ar is a divalent aryl; E is H or methyl; z is 0 or 1; k is an integer in the range of 0 to about 30, and m is 0 or 1, with the proviso that when k is 0, m is 0, and when k is in the range of 1 to about 30, m is 1; (R4-O)n is a polyoxyalkylene, which is a homopolymer, a random copolymer, or a block copolymer of $C_2$-$C_4$ oxyalkylene units, wherein R4 is $C_2H_4$, $C_3H_6$, $C_4H_8$, or a mixture thereof, and n is an integer in the range of about 5 to about 250, preferably about 5 to about 100, more preferably about 10 to about 80, and most preferably about 15 to about 60; Y is —R4O—, —R4NH—, —C(O)—, —C(O)NH—, —R4NHC(O)NH—, or —C(O)NHC(O)—; and R5 is a substituted or unsubstituted alkyl selected from the group consisting of a $C_8$-$C_{40}$ linear alkyl, a $C_8$-$C_{40}$ branched alkyl, a $C_8$-$C_{40}$ carbocyclic alkyl, a $C_2$-$C_{40}$ alkyl-substituted phenyl, an aryl-substituted $C_2$-$C_{40}$ alkyl, and a $C_8$-$C_{80}$ complex ester; wherein the R5 alkyl group optionally comprises one or more substituents selected from the group consisting of a hydroxyl group, an alkoxyl group, and a halogen group; and H is an associative-like vinyl monomer selected from the group consisting of cetyl polyethoxylated methacrylate (CEM), cetearyl polyethoxylated methacrylate (CSEM), stearyl polyethoxylated (meth)acrylate, arachidyl polyethoxylated (meth)acrylate, behenyl polyethoxylated methacrylate (BEM), lauryl polyethoxylated methacrylate (LEM), cerotyl polyethoxylated (meth)acrylate, monthanyl polyethoxylated (meth)acrylate, melissyl polyethoxylated (meth)acrylate, lacceryl polyethoxylated (meth) acrylate, tristyryl phenolpolyethoxylated methacrylate (TEM), hydrogenated castor oil polyethoxylated methacrylate (HCOEM), canola polyethoxylated (meth)acrylate, and cholesterol polyethoxylated methacrylate (CHEM), E, F, G, and H are covalently attached to each other;

with the proviso that G and H are not the same.

In another embodiment of the instant invention, the inventive multi-purpose copolymer according to formula (I) is the polymerization product of a monomer mixture comprising, on a total monomer mixture weight basis: (a) about 81 to about 99.8 weight percent of at least one amino-substituted vinyl monomer (monomer A) or a salt thereof; (b) about 0.1 to about 18.9 weight percent of at least one hydrophobic nonionic vinyl monomer (monomer B); (c) about 0.1 to about 18.9 weight percent of at least one associative-like monomer (monomer C); (d) about 0 to about 18.8 weight percent of at least associative-like monomer (monomer D); optionally, (w) about 0 to about 10 weight percent of a hydroxyl-substituted vinyl monomer (monomer W); optionally, (x) about 0 to about 5 weight percent of a cross linking monomer (monomer X); optionally (y) about 0 to about 10 weight percent of a chain transfer agent (Y); and, optionally, (z) about 0 to about 2 weight percent of a polymeric stabilizer (Z), with the proviso that when both C and D are present in the copolymer, C and D are not the same.

In another embodiment of the instant invention, the inventive multi-purpose copolymer according to formula (II) is the polymerization product of a monomer mixture comprising, on a total monomer mixture weight basis: (e) about 5 to about 99.6 weight percent of at least one amino-substituted vinyl monomer (monomer E) or a salt thereof; (f) about 5 to about 99.6 weight percent of at least one hydrophobic nonionic vinyl monomer (monomer F); (g) about 0.1 to about 40 weight percent of at least one associative-like monomer (monomer G); (h) about 0.1 to about 40 weight percent of at least associative-like monomer (monomer H); optionally, (w) about 0 to about 10 weight percent of a hydroxyl-substituted vinyl monomer (monomer W); optionally, (x) about 0 to about 5 weight percent of a cross linking monomer (monomer X); optionally (y) about 0 to about 10 weight percent of a chain transfer agent (Y); and, optionally, (z) about 0 to about 2 weight percent of a polymeric stabilizer (Z), with the proviso that G and H are not the same.

In another embodiment of the instant invention, the inventive multi-purpose copolymer according to formula (I) is the polymerization product of a monomer mixture comprising, on a total monomer mixture weight basis: (a) about 81 to about 99.8 weight percent of at least one amino-substituted vinyl monomer (monomer A) or a salt thereof; (b) about 0.1 to about 18.9 weight percent of at least one hydrophobic nonionic vinyl monomer (monomer B); (c) about 0.1 to about 18.9 weight percent of at least one associative-like monomer (monomer C); (d) about 0 to about 18.8 weight percent of at least associative-like monomer (monomer D); (w) about 0.01 to about 10 weight percent of a hydroxyl-substituted vinyl monomer (monomer W); (x) about 0.01 to about 5 weight percent of a cross linking monomer (monomer X); (y) about 0.01 to about 10 weight percent of a chain transfer agent (Y); and, (z) about 0.01 to about 2 weight percent of a polymeric stabilizer (Z), with the proviso that when both C and D are present in the copolymer, C and D are not the same.

In another embodiment of the instant invention, the inventive multi-purpose copolymer according to formula (II) is the polymerization product of a monomer mixture comprising, on a total monomer mixture weight basis: (e) about 5 to about 99.6 weight percent of at least one amino-substituted vinyl monomer (monomer E) or a salt thereof; (f) about 5 to about 99.6 weight percent of at least one hydrophobic nonionic vinyl monomer (monomer F); (g) about 0.1 to about 40 weight percent of at least one associative-like monomer (monomer G); (h) about 0.1 to about 40 weight percent of at least associative-like monomer (monomer H); (w) about 0.01 to about 10 weight percent of a hydroxyl-substituted vinyl monomer (monomer W); (x) about 0.01 to about 5 weight percent of a cross linking monomer (monomer X); (y) about 0.01 to about 10 weight percent of a chain transfer agent (Y); and, (z) about 0.01 to about 2 weight percent of a polymeric stabilizer (Z), with the proviso that G and H are not the same.

The terms "and/or" or "or/and" in the present context are meant to express that not only one of the defined alternatives (substituents) may be present, but also several of the defined alternatives (substituents) together, namely mixtures of different alternatives (substituents).

The term "at least" is meant to define one or more than one, for example one or two or three, etc.

The term "optionally substituted" means that the radical to which it refers is either unsubstituted or substituted.

Throughout this specification and the claims which follow, unless the context requires otherwise, the word "comprise", or variations such as "comprises" or "comprising", will be understood to imply the inclusion of a stated integer or step or group of integers or steps but not the exclusion of any other integer or step or group of integers or steps.

The phrase "add up to substantially 100 weight percent relative to the total weight of the copolymer" used above in relation to "a, b, c, and d" and "e, f, g, and h" means that the copolymer is formed from primarily a, b, c and d or e, f, g and h. It is known that associative monomers such as those described by C, D, G and H may contain residual unsaturated carboxylic acids such as (meth)acrylic acid, crotonic, maleic, fumaric, itaconic or aconitic acid. Thus the formed copolymers of formulae (I) and (II) may contain from small amounts of the residual unsaturated carboxylic acids. Typically this incorporation will range from 0 to about 4, 5, 6 or 7 weight percent of the total formed copolymer. The range will of course depend on the purity of the associative monomers used.

Additionally, the phrase "add up to substantially 100 weight percent releative to the total weight of the copolymer" does not exclude the presence of crosslinkers or chain transfer agents.

As used herein the term "alkyl" means a substituted or unsubstituted aliphatic hydrocarbon moiety including linear, branched and carbocyclic alkyl moieties. The term "carbocyclic alkyl" means an alkyl group comprising one or more carbocyclic rings of from 3 to about 12 carbon atoms in size and optionally including alkyl substituents on the carbocyclic ring. The term "aryl" includes substituted and unsubstituted phenyl and naphthyl moieties. Modifiers of the form "Cx-Cy" designate that the alkyl or carbocyclic alkyl groups have molecular formulae containing a total of x to y carbon atoms, where x and y are specified integers. As used herein and in the attached claims, the term "complex ester" means a di-, tri-, or poly-ester of a polyol such as a sugar, having at least one hydroxyl group capable of being alkylated with a C2-C7 alkylene oxide. The term "complex ester" includes, in particular the complex hydrophobes described in Jenkins et al., in U.S. Pat. No. 5,639,841, the relevant disclosure of which is incorporated herein by reference.

The terms "halogen-substituted", "hydroxy-substituted", "carboxy-substituted", "polyoxyalkylene-substituted", "alkyl-substituted", and "aryl-substituted" as used herein in reference to alkyl or aryl groups, and the like, mean that at least one hydrogen atom on an alkyl, aryl, or like group has been replaced by at least one halogen atom, hydroxyl group, carboxyl group, polyoxyalkylene group, alkyl group, or aryl group, respectively. The terms "poly(meth)acrylate" and "poly(meth)acrylamide" as used herein refer in the alternative to polyacrylate or polymethacrylate, and to polyacrylamide or polymethacrylamide, respectively.

Suitable monomers useful in the preparation of the copolymers of the present invention are described below.

Amino-substituted vinyl monomers suitable for the preparation of the inventive copolymers are basic, polymerizable, ethylenically unsaturated monomers preferably containing at least one amino functional group. These basic amino groups can be derived from mono-, di- or poly-amino alkyl groups or nitrogen containing heteroaromatic groups. The amino group can comprise primary, secondary or tertiary amines. The monomers can be used in the amino form or in the salt form, as desired.

The polymers of the present invention preferably include an amino-substituted vinyl monomer selected from the group consisting of mono-(C1-C4)alkylamino(C1-C8)alkyl (meth)acrylate, di-(C1-C4)alkylamino(C1-C8)alkyl(meth) acrylate, mono-(C1-C4)alkylamino(C1-C8)alkyl-(meth) acrylamide, di-(C1-C4)alkylamino(C1-C8)alkyl(meth) acrylamide, nitrogen-containing heterocyclic(meth) acrylamide, nitrogen-containing heterocyclic (meth) acrylate, and mixtures thereof.

Examples of amino-substituted vinyl monomers include, but are not limited to: a mono- or di-(C1-C4)alkylamino (C1-C4)alkyl(meth)acrylate, such as 2-(N,N-dimethylamino)ethyl(meth)acrylate, 3-(N,N-dimethylamino)propyl (meth)acrylate, 4-(N,N-dimethylamino)butyl(meth)acrylate, (N,N-dimethylamino)-t-butyl(meth)acrylate, 2-(N,N-diethylamino)ethyl(meth)acrylate, 3-(N,N-diethylamino)propyl (meth)acrylate, 4-(N,N-diethylamino)butyl(meth)acrylate, 2-(N,N-dipropylamino)ethyl(meth)acrylate, 3-(N,N-dipropylamino)propyl(meth)acrylate, 4-(N,N-dipropylamino)butyl(meth)acrylate, and the like; a mono- or di-(C1-C4) alkylamino(C1-C4)alkyl(meth)acrylamide such as N'-(2-N, N-dimethylamino)ethyl methacrylamide, N'-(3-N,N-dimethylamino)propyl acrylamide, and the like; and a nitrogen-containing heterocyclic (meth)acrylamide or (meth)acrylate such as N-(2-pyridyl)acrylamide, N-(2-imidazoyl)methacrylamide, 2-(4-morpholinyl)ethyl methacrylate, 2-(4-morpholinyl)ethyl acrylate, N-(4-morpholinyl) methacrylamide, N-(4-morpholinyl)acrylamide, 2-vinyl pyridine, 4-vinyl pyridine, and the like.

Suitable salt forms of the amino-substituted monomers include, but are not limited to, mineral acid salts such as the hydrochloride, sulfate, and phosphate salts; and organic acid salts such as the acetate, maleate, and fumarate salts; and the like.

The foregoing monomers or salts thereof can be used as the amino-substituted vinyl monomer component of the inventive copolymers, individually, or in mixtures of two or more. Particularly preferred amino-substituted monomers are 2-(N,N-dimethylamino)ethyl(meth)acrylate, 3-(N,N-dimethylamino)propyl(meth)acrylate, and N'-(3-N,N-dimethylamino)propyl(meth)acrylamide. Most preferred are 2-(N, N-dimethylamino)ethyl methacrylate (DMAEMA), 2-(N,N-diethylamino)ethyl methacrylate (DEAEMA), 2-(tert-butylamino)ethyl methacrylate (TBAEMA), 2-(N,N-dimethylamino)propyl methacrylamide (DMAPMAm), and 2-(N,N-dimethylamino)neopentyl acrylate (DMANPA).

The amino-substituted vinyl monomer (monomer A of formula (I)) preferably comprises about 81 to about 99 weight percent of the total monomer mixture by weight, more preferably about 85 to about 99 weight percent, and most preferably about 85 to about 95 weight percent, on a total monomer mixture weight basis. More precisely, the amino-substituted vinyl monomer (monomer A of formula (I)) weight percent level, based on the total monomer mixture, is selected from the group consisting of 81, 82, 83, 84, 85, 86, 87, 88, 89, 90, 91, 92, 93, 94, 95, 96, 97, 98 and 99 weight percent.

The amino-substituted vinyl monomer (monomer E of formula (II)) preferably comprises from about 10 to about 90 weight percent of the total monomer mixture by weight, more preferably from about 20 to about 80 weight percent, most preferably from about 30 to about 70 weight percent, and even more preferably from about 40 to about 60 weight percent, based on a total monomer mixture weight basis. More precisely, the amino-substituted vinyl monomer (monomer E of formula (II)) weight percent level, based on the total monomer mixture, is selected from the group consisting of 10, 15, 20, 30, 35, 40, 45, 50, 55, 60, 65, 70, 75, 80, 85 and 90 weight percent.

Hydrophobic nonionic vinyl monomers suitable for use in the preparation of the inventive copolymers are copolymerizable, nonionic, ethylenically unsaturated monomers having either of the following formulae (III) or (IV):

$$CH_2=C(X)Z, \qquad (III)$$

$$CH_2=CH-OC(O)R; \qquad (IV)$$

wherein, in each of formulas (III) and (IV), X is H or methyl; and Z is —C(O)OR1, —C(O)NH2, —C(O)NHR1, —C(O)N(R1)2, —C6H4R1, —C6H4OR1-, —C6H4Cl, —CN, —NHC(O)CH3, —NHC(O)H, N-(2-pyrrolidonyl), N-caprolactamyl, —C(O)NHC(CH3)3, —C(O) NHCH2CH2-N-ethyleneurea, —SiR3, —C(O)O(CH2) xSiR3, —C(O)NH(CH2)xSiR3, or —(CH2)xSiR3; x is an integer in the range of 1 to about 6; each R is independently C1-C30 alkyl; each R1 is independently C1-C30 alkyl, hydroxy-substituted C2-C30 alkyl or halogen-substituted C1-C30 alkyl.

Non-limiting examples of preferred hydrophobic nonionic vinyl monomers include C1-C30 alkyl(meth)acrylates; C1-C30 alkyl(meth)acrylamides; styrene; substituted styrenes such as vinyl toluene, (e.g., 2-methyl styrene), butyl styrene, isopropyl styrene, p-chloro styrene, and the like; vinyl esters such as vinyl acetate, vinyl butyrate, vinyl caprolate, vinyl pivalate, vinyl neodecanoate, and the like; unsaturated nitrites such as methacrylonitrile, acrylonitrile and the like; and unsaturated silanes such as trimethylvinylsilane, dimethylethylvinylsilane, allyldimethylphenylsilane, allytrimethylsilane, 3-acrylamidopropyltrimethylsilane, 3-trimethylsilylpropyl methacrylate, and the like.

Particularly preferred hydrophobic nonionic vinyl monomers include C1-C30 alkyl esters of acrylic acid and of methacrylic acid and mixtures thereof, such as ethyl acrylate (EA), methyl methacrylate (MMA), 3,3,5-trimethylcyclohexyl methacrylate (TMCHMA), and mixtures thereof.

The hydrophobic nonionic vinyl monomers (monomer B of formula (I)) preferably comprises from about 0.1 to about 18 weight percent of the total monomer mixture by weight, more preferably from about 1 to about 15 weight percent, most preferably about 5 to about 15 weight percent, and even more preferably from about 5 to about 10 weight percent on a total monomer mixture weight basis. More precisely, the hydrophobic nonionic vinyl monomer (monomer B of formula (I)) weight percent level, based on the total monomer mixture, is selected from the group consisting of 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17 and 18 weight percent.

The hydrophobic nonionic vinyl monomer (monomer F of formula (II)) preferably comprises from about 10 to about 90 weight percent of the total monomer mixture by weight, more preferably from about 20 to about 80 weight percent, most preferably from about 30 to about 70 weight percent, and even more preferably from about 40 to about 60 weight percent, based on a total monomer mixture weight basis. More precisely, the hydrophobic nonionic vinyl monomer (monomer F of formula (II)) weight percent level, based on the total monomer mixture, is selected from the group consisting of 10, 15, 20, 30, 35, 40, 45, 50, 55, 60, 65, 70, 75, 80, 85 and 90 weight percent.

Associative vinyl monomers suitable for use in the production of the inventive copolymers are compounds preferably having an ethylenically unsaturated end group portion (i) for addition polymerization with the other monomers of the system; a polyoxyalkylene midsection portion (ii) for imparting selective hydrophilic properties to the product polymer and a hydrophobic end group portion (iii) for providing selective hydrophobic properties to the polymer.

The portion (i) supplying the ethylenically unsaturated end group preferably is derived from an alpha,beta-ethylenically unsaturated mono or di-carboxylic acid or the anhydride thereof, more preferably a C3 or C4 mono- or di-carboxylic acid or the anhydride thereof. Alternatively, portion (i) of the associative monomer can be derived from an allyl ether or vinyl ether; a nonionic vinyl-substituted urethane monomer, such as disclosed in U.S. Reissue Pat. No. 33,156 or U.S. Pat. No. 5,294,692; or a vinyl-substituted urea reaction product, such as disclosed in U.S. Pat. No. 5,011,978; the relevant disclosures of each are incorporated herein by reference.

The midsection portion (ii) is preferably a polyoxyalkylene segment of about 5 to about 250, more preferably about 10 to about 120, and most preferably about 15 to about 60 repeating C2-C7 alkylene oxide units. Preferred midsection portions (ii) include polyoxyethylene, polyoxypropylene, and polyoxybutylene segments comprising about 5 to about 150, more preferably about 10 to about 100, and most preferably about 15 to about 60 ethylene, propylene or butylene oxide units, and random or non-random sequences of ethylene oxide, propylene oxide and or butylene oxide units.

The hydrophobic end group portion (iii) of the associative monomers is preferably a hydrocarbon moiety belonging to one of the following hydrocarbon classes: a C8-C40 linear alkyl, an aryl-substituted C2-C40 alkyl, a C2-C40 alkyl-substituted phenyl, a C8-C40 branched alkyl, a C8-C40 carbocyclic alkyl; and a C8-C80 complex ester.

Non-limiting examples of suitable hydrophobic end group portions (iii) of the associative monomers are linear or branched alkyl groups having about 8 to about 40 carbon atoms such as capryl (C8), isooctyl (branched C8), decyl (C10), lauryl (C12), myristyl (C14), cetyl (C16), cetearyl (C16-C18), stearyl (C18), isostearyl (branched C18), arachidyl (C20), behenyl (C22), lignoceryl (C24), cerotyl (C26), montanyl (C28), melissyl (C30), lacceryl (C32), and the like.

Examples of linear and branched alkyl groups having about 8 to about 40 carbon atoms that are derived from a natural source include, without being limited thereto, alkyl groups derived from hydrogenated peanut oil, soybean oil and canola oil (all predominately C18), hydrogenated tallow oil (C16-C18), and the like; and hydrogenated C10-C30 terpenols, such as hydrogenated geraniol (branched C10), hydrogenated farnesol (branched C15), hydrogenated phytol (branched C20), and the like.

Non-limiting examples of suitable C2-C40 alkyl-substituted phenyl groups include octylphenyl, nonylphenyl, decylphenyl, dodecylphenyl, hexadecylphenyl, octadecylphenyl, isooctylphenyl, sec-butylphenyl, and the like.

Suitable C8-C40 carbocylic alkyl groups include, without being limited thereto, groups derived from sterols from animal sources, such as cholesterol, lanosterol, 7-dehydrocholesterol, and the like; from vegetable sources, such as phytosterol, stigmasterol, campesterol, and the like; and from yeast sources, such as ergosterol, mycosterol, and the like. Other carbocyclic alkyl hydrophobic end groups useful in the present invention include, without being limited thereto, cyclooctyl, cyclododecyl, adamantyl, decahydronaphthyl, and groups derived from natural carbocyclic materials such as pinene, hydrogenated retinol, camphor, isobornyl alcohol, and the like.

Exemplary aryl-substituted C2-C40 alkyl groups include, without limitation thereto, styryl (e.g., 2-phenylethyl), distyryl (e.g., 2,4-diphenylbutyl), tristyryl (e.g., 2,4,6-triphenylhexyl), 4-phenylbutyl, 2-methyl-2-phenylethyl, tristyrylphenolyl, and the like.

Non-limiting examples of suitable C8-C80 complex esters include hydrogenated castor oil (predominately the triglyceride of 12-hydroxystearic acid); 1,2-diacyl glycerols such as 1,2-distearyl glycerol, 1,2-dipalmityl glycerol, 1,2-dimyristyl glycerol, and the like; di-, tri-, or polyesters of sugars such as 3,4,6-tristearyl glucose, 2,3-dilauryl fructose, and the like; and sorbitan esters such as those disclosed in U.S. Pat. No. 4,600,761 to Ruffner et al., the pertinent disclosures of which are incorporated herein by reference.

Useful associative monomers can be prepared by any method known in the art. See, for example, U.S. Pat. No. 4,421,902 to Chang et al.; No. U.S. Pat. No. 4,384,096 to Sonnabend; U.S. Pat. No. 4,514,552 to Shay et al.; U.S. Pat. No. 4,600,761 to Ruffner et al.; U.S. Pat. No. 4,616,074 to Ruffner; U.S. Pat. No. 5,294,692 to Barron et al.; U.S. Pat. No. 5,292,843 to Jenkins et al.; U.S. Pat. No. 5,770,760 to Robinson; and U.S. Pat. No. 5,412,142 to Wilkerson, III et al.; the pertinent disclosures of which are incorporated herein by reference.

U.S. Pat. No. 4,075,411 describes several processes for preparing such useful associative monomers. These associative monomers are sometimes referred to as "vinyl surfactant esters". These vinyl surfactant esters or associative monomers may typically be prepared by the acid catalyzed condensation of commercially available nonionic polyoxyalkylene surfactant alcohols with acrylic, methacrylic, crotonic, maleic, fumaric, itaconic or aconitic acid.

It is therefore possible that unreacted ethylenically unsaturated acid may be mixed with the formed associative monomer. For example, about 0.01 to about 35.0 weight %, more typically 1.0 to about 20, 25 or 30 weight % or most typically 10.0 to about 20, 25, or 30 weight % residual unsaturated (meth)acylic acid may be present with the associative monomer. As the residual unreacted acid contains unsaturation, it will also be incorporated into the polymer of formulae (I) or (II) above. Thus if for example 4 wt. % associative monomer is incorporated into the polymer of formulae (I) or (II), and about 30 wt. % of the associative monomer is unreacted ethylenically unsaturated carboxylic acid, the formed polymer will contain about 1.2 wt. % acid functionality.

Examples of preferred associative vinyl monomers include those having the following formula (V):

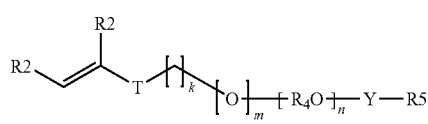

wherein, each R2 is independently H, methyl, —C(O)OH, or —C(O)OR3; R3 is C1-C30 alkyl; T is —CH₂C(O)O—, —C(O)O—, —O—, —CH₂O—, —NHC(O)NH—, —C(O)NH—, —Ar—(CE₂)z-NHC(O)O—, —Ar—(CE₂)z-NHC(—O)NH—, or —CH₂CH₂NHC(O)—; Ar is a divalent aryl; E is H or methyl; z is 0 or 1; k is an integer in the range of 0 to about 30, and m is 0 or 1, with the proviso that when k is 0, m is 0, and when k is in the range of 1 to about 30, m is 1; (R4-O)n is a polyoxyalkylene, which is a homopolymer, a random copolymer, or a block copolymer of C₂-C₄ oxyalkylene units, wherein R4 is C₂H₄, C₃H₆, C₄H₈, or a mixture thereof, and n is an integer in the range of about 5 to about 250, preferably about 5 to about 100, more preferably about 10 to about 80, and most preferably about 15 to about 60; Y is —R4O—, —R4NH—, —C(O)—, —C(O)NH—, —R4NHC(O)NH—, or —C(O)NHC(O)—; and R5 is a substituted or unsubstituted alkyl selected from the group consisting of a C₈-C₄₀ linear alkyl, a C₈-C₄₀ branched alkyl, a C₈-C₄₀ carbocyclic alkyl, a C₂-C₄₀ alkyl-substituted phenyl, an aryl-substituted C₂-C₄₀ alkyl, and a C₈-C₈₀ complex ester; wherein the R5 alkyl group optionally comprises one or more substituents selected from the group consisting of a hydroxyl group, an alkoxyl group, and a halogen group.

Particularly preferred associative vinyl monomers of formula (V) include cetyl polyethoxylated methacrylate (CEM), cetearyl polyethoxylated methacrylate (CSEM), stearyl polyethoxylated (meth)acrylate, arachidyl polyethoxylated (meth)acrylate, behenyl polyethoxylated methacrylate (BEM), lauryl polyethoxylated methacrylate (LEM), cerotyl polyethoxylated (meth)acrylate, montanyl polyethoxylated (meth)acrylate, melissyl polyethoxylated (meth)acrylate, lacceryl polyethoxylated (meth)acrylate, tristyryl phenolpolyethoxylated methacrylate (TEM), hydrogenated castor oil polyethoxylated methacrylate (HCOEM), canola polyethoxylated (meth)acrylate, and cholesterol polyethoxylated methacrylate (CHEM), where the polyethoxylated portion of the monomer comprises about 5 to about 100, preferably about 10 to about 80, and more preferably about 15 to about 60 ethylene oxide repeating units.

The associative vinyl monomer (monomer C of formula (I)) preferably comprises about 0.5 to about 18 weight percent of the total monomer mixture by weight, more preferably about 1 to about 15 weight percent, and most preferably about 1 to about 10 weight percent, on a total monomer mixture weight basis. More precisely, the associative vinyl monomer (monomer C of formula (I)) weight percent level, based on the total monomer mixture, is selected from the group consisting of 0.1, 0.5, 1, 2, 3, 4, 5, 6, 7, 8, 9, 10, 11, 12, 13, 14, 15, 16, 17 and 18 weight percent.

The associative vinyl monomer (monomer G of formula (II)) preferably comprises about 0.5 to about 40 weight percent of the total monomer mixture by weight, more preferably about 1 to about 30 weight percent, and most preferably about 1 to about 15 weight percent, on a total monomer mixture weight basis. More precisely, the associative vinyl monomer (monomer G of formula (II)) weight percent level, based on the total monomer mixture, is selected from the group consisting of 0.1, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and 40 weight percent.

The associative vinyl monomer (monomer D of formula (I)) preferably comprises about 0 to about 18 weight percent of the total monomer mixture by weight, more preferably (when present) about 1 to about 15 weight percent, and most preferably (when present) about 1 to about 10 weight percent, on a total monomer mixture weight basis. More precisely, the associative vinyl monomer (monomer D of formula (I)) weight percent level, based on the total monomer mixture, is selected from the group consisting of 0, 0.1, 0.5, 1, 2, 3, 4, 5, 6, 7, 8, 9, 10, 11, 12, 13, 14, 15, 16, 17 and 18 weight percent.

The associative vinyl monomer (monomer H of formula (II)) preferably comprises about 0.5 to about 40 weight percent of the total monomer mixture by weight, more preferably about 1 to about 30 weight percent, and most preferably about 1 to about 15 weight percent, on a total monomer mixture weight basis. More precisely, the associative vinyl monomer (monomer H of formula (II)) weight percent level, based on the total monomer mixture, is selected from the group consisting of 0.1, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and 40 weight percent.

The inventive copolymers can optionally be prepared from monomer mixtures containing hydroxy-substituted nonionic vinyl monomers (monomer W in formulae (I) and (II)). The hydroxy-substituted nonionic vinyl monomers are ethylenically unsaturated monomers comprising one or more hydroxyl substituents.

Examples of suitable hydroxy-substituted nonionic vinyl monomers (monomer W in formulae (I) and (II)) include, but are not limited to, a hydroxy-substituted (C1-C4)alkyl (meth)acrylate such as 2-hydroxyethyl methacrylate (HEMA), 2-hydroxyethyl acrylate (2-HEA), 3-hydroxypropyl acrylate, and the like; a hydroxy-substituted (C1-C4) alkyl(meth)acrylamide such as N-(2-hydroxyethyl)methacrylamide, N-(2-hydroxyethyl)acrylamide, N-(3-hydroxypropyl)acrylamide, N-(2,3-dihydroxypropyl)acrylamide, and the like. Other useful hydroxy-substituted nonionic vinyl monomers include allyl alcohol, glycerol monoallyl ether, 3-methyl-3-buten-1-ol, and vinyl alcohol precursors and equivalents, such as vinyl acetate.

When utilized, the monomer reaction mixture preferably contains one or more hydroxy-substituted nonionic vinyl monomers (monomer W in formulae (I) and (II)) in amounts up to about 10 weight percent based on the total monomer mixture weight. In a preferred embodiment, the amount of hydroxy-substituted nonionic vinyl monomer in the mixture is in the range of about 0.01 to about 10 weight percent based on the total monomer mixture weight, more preferably about 1 to about 8 weight percent, most preferably about 1 to about 5 weight percent.

The inventive copolymers can be prepared from a monomer mixture comprising one or more crosslinking monomers (monomer X in formulae (I) and (II)) for introducing branching and controlling molecular weight. Mono-unsaturated compounds carrying a reactive group that is capable of causing a formed copolymer to be cross linked before, during, or after polymerization has taken place can also be utilized. Other useful crosslinking monomers include polyfunctional monomers containing multiple reactive groups such as epoxide groups, isocyanate groups, and hydrolyzable silane groups. Various polyunsaturated compounds can be utilized to generate either a partially or substantially cross-linked three dimensional network.

Examples of suitable polyunsaturated crosslinking monomer (monomer X in formulae (I) and (II)) components include, without being limited thereto, polyunsaturated aromatic monomers such as divinylbenzene, divinyl naphthylene, and trivinylbenzene; polyunsaturated alicyclic monomers, such as 1,2,4-trivinylcyclohexane; di-functional esters of phthalic acid such as diallyl phthalate; polyunsaturated aliphatic monomers, such as dienes, trienes, and tetraenes, including isoprene, butadiene, 1,5-hexadiene, 1,5,9-decatriene, 1,9-decadiene, 1,5-heptadiene; and the like.

Other suitable polyunsaturated crosslinking monomers (monomer X in formulae (I) and (II)) include polyalkenyl ethers such as triallyl pentaerythritol, diallyl pentaerythritol, diallyl sucrose, octaallyl sucrose, and trimethylolpropane diallyl ether; polyunsaturated esters of polyalcohols or polyacids such as 1,6-hexanediol di(meth)acrylate, tetramethylene tri(meth)acrylate, allyl acrylate, diallyl itaconate, diallyl fumarate, diallyl maleate, trimethylolpropane tri(meth)acrylate, trimethylolpropane di(meth)acrylate, and polyethylene glycol di(meth)acrylate; alkylene bisacrylamides, such as methylene bisacrylamide, propylene bisacrylamide, and the like; hydroxy and carboxy derivatives of methylene bisacrylamide, such as N,N'-bismethylol methylene bisacrylamide; polyethyleneglycol di(meth)acrylates, such as ethyleneglycol di(meth)acrylate, diethyleneglycol di(meth)acrylate, and triethyleneglycol di(meth)acrylate; polyunsaturated silanes, such as dimethyldivinylsilane, methyltrivinylsilane, allyldimethylvinylsilane, diallyldimethylsilane, and tetravinylsilane; polyunsaturated stannanes, such as tetraallyl tin, and diallyldimethyl tin; and the like.

Useful monounsaturated compounds carrying a reactive group include N-methylolacrylamide; N-alkoxy(meth)acrylamide, wherein the alkoxy group is a C1-C18 alkoxy; and unsaturated hydrolyzable silanes such as triethoxyvinylsilane, tris-isopropoxyvinylsilane, and 3-triethoxysilylpropyl methacrylate; and the like.

Useful polyfunctional crosslinking monomers (monomer X in formulae (I) and (II)) containing multiple reactive groups include, but are not limited to, hydrolyzable silanes such as ethyltriethoxysilane and ethyltrimethoxysilane; epoxy-substituted hydrolyzable silanes, such as 2-(3,4-epoxycyclohexyl)ethyltriethoxysilane and 3-glycidoxypropyltrimethyoxysilane; polyisocyanates, such as 1,4-diisocyanatobutane, 1,6-diisocyanatohexane, 1,4-phenylenediisocyanate-, and 4,4'-oxybis(phenylisocyanate); unsaturated epoxides, such as glycidyl methacrylate and allylglycidyl ether; polyepoxides, such as diglycidyl ether, 1,2,5,6-diepoxyhexane, and ethyleneglycoldiglycidyl ether; and the like.

Particularly useful are polyunsaturated crosslinkers (monomer X in formulae (I) and (II)) derived from ethoxylated polyols, such as diols, triols and bis-phenols, ethoxylated with about 2 to about 100 moles of ethylene oxide per mole of hydroxyl functional group and end-capped with a polymerizable unsaturated group such as a vinyl ether, allyl ether, acrylate ester, methacrylate ester, and the like. Examples of such crosslinkers include bisphenol A ethoxylated dimethacrylate; bisphenol F ethoxylated dimethacrylate, ethoxylated trimethylol propane trimethacrylate, and the like. Other ethoxylated crosslinkers useful in the copolymers of the present invention include ethoxylated polyol-derived crosslinkers disclosed in U.S. Pat. No. 6,140,435 to Zanotti-Russo, the pertinent disclosures of which are incorporated herein by reference.

Examples of particularly preferred crosslinking monomers (monomer X in formulae (I) and (II)) are acrylate and methacrylate esters of polyols having at least two acrylate or methacrylate ester groups, such as trimethylolpropane triacrylate (TMPTA), trimethylolpropane dimethacrylate, triethylene glycol dimethacrylate (TEGDMA), ethoxylated (30) bisphenol A dimethacrylate (EOBDMA), and the like.

When utilized, crosslinking monomers are present in the monomer reaction mixture preferably in an amount of up to about 5 weight percent, based on total monomer mixture weight. In a preferred embodiment, the crosslinking monomers are present in an amount in the range of about 0.01 to about 3 weight percent, based on the total monomer mixture weight, more preferably about 0.05 to about 2 weight percent, most preferably about 0.1 to about 1 weight percent of the monomer mixture.

The inventive copolymers can optionally be prepared from a monomer mixture comprising one or more chain transfer agents (Y in formulae (I) and (II)).

Suitable chain transfer agents (Y in formulae (I) and (II)) for use in this invention, without being limited thereto, are selected from a variety of thio and disulfide containing compounds, such as C1-C18 alkyl mercaptans, mercaptocarboxylic acids, mercaptocarboxylic esters, thioesters, C1-C18 alkyl disulfides, aryldisulfides, polyfunctional thiols, and the like; phosphites and hypophosphites; haloalkyl compounds, such as carbon tetrachloride, bromotrichloromethane, and the like; and unsaturated chain transfer agents, such as alpha-methylstyrene.

Polyfunctional thiols include trifunctional thiols, such as trimethylolpropane-tris-(3-mercaptopropionate), tetrafunctional thiols, such as pentaerythritol-tetra-(3-mercaptopropionate), pentaerythritol-tetra(thioglycolate), and pentaerythritol-tetra-(thiolactate); hexafunctional thiols, such as dipentaerythritol-hexa(thioglycolate); and the like.

Alternatively, the chain transfer agent (Y in formulae (I) and (II)) can be any catalytic chain transfer agent which reduces molecular weight of addition polymers during free radical polymerization of vinyl monomers. Examples of catalytic chain transfer agents include, for example, cobalt complexes (e.g., cobalt (II) chelates). Catalytic chain transfer agents can often be utilized in relatively low concentrations relative to thiol-based chain transfer agents.

Examples of preferred chain transfer agents (Y in formulae (I) and (II)) include octyl mercaptan, n-dodecyl mercaptan, t-dodecyl mercaptan, hexadecyl mercaptan, octadecyl mercaptan (ODM), isooctyl 3-mercaptopropionate (IMP), butyl 3-mercaptopropionate, 3-mercaptopropionic acid, butyl thioglycolate, isooctyl thioglycolate, dodecyl thioglycolate, and the like. The chain transfer agents can be added to a monomer reaction mixture preferably in amounts of up to about 10 weight percent of polymerizable monomer mixture, based on total monomer mixture weight. When present, the chain transfer agent preferably comprises at least about 0.1 percent by weight based on the total monomer weight.

The inventive copolymers can be manufactured by conventional polymerization techniques, such as emulsion polymerization. The polymerization can be performed as a simple batch process, as a metered addition process, or the reaction can be initiated as a small batch and then the bulk of the monomers can be continuously metered into the reactor (seed process). Typically the polymerization process is carried out at a reaction temperature in the range of about 20 to about 80 C, however, higher or lower temperatures can be used. To facilitate emulsification of the monomer mixture, the emulsion polymerization is carried out in the presence of at least one surfactant. Preferably the emulsion polymerization is carried out in the presence of surfactant in the amount of about 1 to about 10 percent by weight, more preferably in the range of about 3 to about 8, most preferably in the range of about 5 to about 7 percent by weight, on a total emulsion weight basis. The emulsion polymerization reaction mixture also includes one or more free radical initiators, preferably in an amount in the range of about 0.01 to about 3 weight percent based on total monomer weight. The polymerization can be performed in an aqueous or aqueous alcohol medium at neutral to moderately alkaline pH.

In a typical polymerization, a mixture of monomers is added with mixing agitation to a solution of emulsifying surfactant, such as a nonionic surfactant, preferably a linear or branched alcohol ethoxylate, or mixtures of nonionic surfactants and anionic surfactants, such as fatty alcohol sulfates or alkyl sulfonates, in a suitable amount of water, in a suitable reactor, to prepare a monomer emulsion. The emulsion is deoxygenated by any convenient method, such as by sparging with nitrogen, and then a polymerization reaction is initiated by adding a polymerization catalyst (initiator) such as sodium persulfate, or any other suitable addition polymerization catalyst, as is well known in the emulsion polymerization art. The reaction is agitated until the polymerization is complete, typically for a time in the range of about 4 to about 16 hours. The monomer emulsion can be heated to a temperature in the range of about 20 to about 80 C prior to addition of the initiator, if desired. Unreacted monomer can be eliminated by addition of more catalyst, as is well known in the emulsion polymerization art. The resulting polymer emulsion product can then be discharged from the reactor and packaged for storage or use. Optionally, the pH or other physical and chemical characteristics of the emulsion can be adjusted prior to discharge from the reactor. Typically, the product emulsion has a total solids content in the range of about 10 to about 40 weight percent. Typically, the total polymer content of the product emulsion is in the range of about 15 to about 35 weight percent, generally not more than about 25 weight percent.

Suitable surfactants for facilitating emulsion polymerizations include nonionic, anionic, amphoteric, cationic surfactants, and mixtures thereof. Most commonly, nonionic and anionic surfactants are utilized or mixtures thereof. The physical properties of the neutralized polymer (e.g., viscosity, spreadability, clarity, texture, and the like) can be varied by appropriate selection of the hydrophobic and hydrophilic properties of the emulsifying surfactant.

Nonionic surfactants suitable for facilitating emulsion polymerizations include, without limitation, linear or branched alcohol ethoxylates, C8-C12 alkylphenol alkoxylates, such as octylphenol ethoxylates, polyoxyethylene polyoxypropylene block copolymers, and the like. Other useful nonionic surfactants include C8-C22 fatty acid esters of polyoxyethylene glycol, mono and diglycerides, sorbitan esters and ethoxylated sorbitan esters, C8-C22 fatty acid glycol esters, block copolymers of ethylene oxide and propylene oxide having an HLB value of greater than about 15, ethoxylated octylphenols, and combinations thereof.

Preferred alkylphenol alkoxylate surfactants include an octylphenol sold under the trade name IGEPAL CA-897 by Rhodia, Inc. Preferred linear alcohol alkoxylates include polyethylene glycol ethers of cetearyl alcohol (a mixture of cetyl and stearyl alcohols) sold under the trade names PLURAFAC C-17, PLURAFAC A-38 and PLURAFAC A-39 by BASF Corp. Preferred polyoxyethylene polyoxypropylene block copolymers include copolymers sold under the trade names PLURONIC F127, and PLURONIC L35 by BASF Corp.

Other preferred nonionic surfactants include Ethoxylated (50) linear fatty alcohols such as DISPONIL A 5060 (Cognis), branched alkyl ethoxylates such as GENAPOL X 1005 (Clariant Corp.), secondary C12-C14 alcohol ethoxylates such as TERGITOL S15-30 and S15-40 (Dow Chemical Co.), ethoxylated octylphenol-based surfactants such as TRITON X-305, X-405 and X-705 (Dow Chemical Co.), IGEPAL CA 407, 887, and 897 (Rhodia, Inc.), ICONOL OP 3070 and 4070 (BASF Corp.), SYNPERONIC OP 30 and 40 (Uniqema), block copolymers of ethylene oxide and propylene oxide such as PLURONIC L35 and F127 (BASF Corp.), and secondary C11 alcohol ethoxylates such as EMULSOGEN EPN 407 (Clariant Corp.). Numerous other suppliers are found in the trade literature.

Anionic surfactants suitable for facilitating emulsion polymerizations include sodium lauryl sulfate, sodium dodecyl benzene sulfonate, sodium dioctyl sulfosuccinate, sodium di-sec-butyl naphthylene sulfonate, disodium dodecyl diphenyl ether sulfonate, and disodium n-octadecyl sulfosuccinate, and the like.

Suitable polymeric stabilizers [also known as protective colloids, (Z in formulae (I) and (II))] for the emulsion polymerization process of this invention are water-soluble polymers, including, for example, synthetic polymers, such as polyvinyl alcohol, partially hydrolyzed polyvinyl acetate, polyvinylpyrrolidone, polyacrylamide, polymethacrylamide, carboxylate-functional addition polymers, polyalkyl vinyl ethers and the like; water-soluble natural polymers, such as gelatin, pectins, alginates, casein, starch, and the like; and modified natural polymers, such as methylcellulose, hydroxypropylcellulose, carboxymethylcellulose, allyl modified hydroxyethylcellulose, and the like. In some cases, it can be of advantage to use mixtures of a synthetic and a natural protective colloid, for example, a mixture of polyvinyl alcohol and casein. Further suitable natural polymers are mixed ethers such as methylhydroxyethylcellulose and carboxymethylmethylcellulose. Polymeric stabilizers can be utilized in amounts up to about 2 weight percent based on the total emulsion weight. When utilized, a polymeric stabilizer preferably is included in an amount in the range of about 0.0001 to about 1 weight percent, more preferably about 0.01 to about 0.5 weight percent.

The polymeric stabilizers (Z in formulae (I) and (II)) which are used according to this invention are termed water-soluble when they are miscible in water in any proportion or have a solubility in 20 C water of at least about 0.1% by weight and do not precipitate from these aqueous solutions on dilution with water at the foregoing temperature. The molecular weight of the water-soluble synthetic polymeric stabilizers is typically in the range of about 5,000 to about 2,000,000, preferably about 25,000 to about 1,500,000 Daltons. The viscosity of aqueous solutions of the polymeric stabilizers is typically in the range of about 1 to about 10,000 mpa at a concentration of about 2 to about 10% by weight and a temperature of about 20 C.

A particularly preferred polymeric stabilizer (Z in formulae (I) and (II)) is an allyl modified hydroxyethylcellulose, such as TYLOSE AM-HEC grades available from Clariant. The reactive allyl groups in the side chain increase the grafting power of the cellulose ether resulting in a stable emulsion. A preferred TYLOSE stabilizer is allyl modified hydroxyethylcellulose powder (particle size <180 .mu.m) TYLOSE AM H40 YP2 (AMHEC).

Exemplary preferred free radical initiators include, without being limited thereto, the water-soluble inorganic persulfate compounds, such as ammonium persulfate, potassium persulfate, and sodium persulfate; peroxides such as hydrogen peroxide, benzoyl peroxide, acetyl peroxide, and lauryl peroxide; organic hydroperoxides, such as cumene hydroperoxide and t-butyl hydroperoxide; organic peracids, such as peracetic acid; and oil soluble, free radical producing agents, such as 2,2'-azobisisobutyronitrile, and the like, and mixtures thereof. Peroxides and peracids can optionally be activated with reducing agents, such as sodium bisulfite or ascorbic acid, transition metals, hydrazine, and the like. Particularly suitable free-radical polymerization initiators include water soluble azo polymerization initiators, such as 2,2'-azobis(tert-alkyl) compounds having a water solubilizing substituent on the alkyl group. Preferred azo polymerization catalysts include the VAZO free-radical polymerization initiators, available from DuPont, such as VAZO 44 (2,2'-azobis(2-(4,5-dihydroimidazolyl)propane), VAZO 56 (2,2'-azobis(2-methylpropionamidine) dihydrochloride), and VAZO 68 (4,4'-azobis(4-cyanovaleric acid)).

Optionally, other emulsion polymerization additives, such as solvents, buffering agents, chelating agents, inorganic electrolytes, chain terminators, and pH adjusting agents can be included in the polymerization system.

A preferred general emulsion polymerization procedure for the preparation of copolymers of the present invention and of cationic emulsion polymers, in general, is provided below:

A monomer emulsion is preferably prepared in a reactor equipped with a nitrogen inlet and an agitator by combining a desired amount of each monomer in a quantity of water containing an emulsifying amount of a nonionic surfactant, or a mixture of a nonionic surfactant and an anionic surfactant, under a nitrogen atmosphere, and with mixing agitation. The degree of agitation required to form an emulsion from a monomer mixture of the type described above is well known to those of skill in the art. The so-formed emulsion is substantially deoxygenated by any suitable method known in the art, such as by sparging with nitrogen, and then a free radical initiator is added to the emulsion, with continuous mixing agitation, to initiate polymerization. The temperature of the emulsion can be adjusted, before or after addition of the initiator, to a temperature in the range of about 20 to about 60 C if desired. After the addition of initiator, the temperature of the polymerization reaction mixture is typically adjusted to a temperature in the range of about 60 to 80 C and held at such temperature for a time sufficient to complete the polymerization, typically in the range of about 3 to about 14 hours. Optionally, unreacted residual monomers can be destroyed or further polymerized by the addition of various redox reagents or catalysts. The resulting polymer emulsion can then be cooled and discharged from the reactor and collected.

Varying proportions of water can also be utilized, as desired. Water miscible solvents, such as alcohols, and other polymerization additives, as described above, may also be included in the reaction mixture. Preferred alcohols include glycols such as ethylene glycol, propylene glycol, butylene glycol, hexylene glycol, glycerol, and the like.

The product polymer emulsions can be prepared to preferably contain about 1 percent to about 60 percent total polymer solids, more preferably about 10 percent to about 40 percent total polymer solids, most preferably about 15 percent to about 25 percent total polymer solids based on the weight of the polymer.

Prior to any neutralization, the polymer emulsions, as produced, typically have a pH in the range of about 7.5 or greater, a Brookfield viscosity of not more than about 100 mPa at ambient room temperature (spindle #2, 20 rpm), and a particle size of not more than about 300 nm.

Optionally, the produced copolymer emulsions can be further processed by adjusting the pH to a value preferably in the range of about 1 to not more than about 7, if an acidic pH is desired, with acidic materials, preferably organic acids, mineral acids, and the like. The copolymer emulsions typically swell to form smooth, viscous solutions that are flowable and sprayable, or gels at neutral to acidic pH, and the polymers are generally substantially stable at such pH values. The copolymer emulsions can be diluted with water or solvent, or concentrated by evaporating a portion of the water. Alternatively, the obtained copolymer emulsion can be substantially dried to a powder or crystalline form by utilizing equipment well known in the art, such as, for example, a spray drier, a drum drier, a freeze drier, and the like.

The inventive copolymers can be prepared by emulsion polymerization and utilized by incorporating various known additives and conventional adjuvants, and solvents other than water, into the liquid copolymer emulsion product, as needed, to achieve the intended form for use of the final composition without altering or adversely affecting the performance or properties of the copolymer. Alternatively, the copolymer can be incorporated as an ingredient into a formulation, preferably in a liquid form, employing conventional mixing equipment.

A preferred copolymer of this invention, at a weight concentration of about 2% in deionized water, in its neutralized or acidic form at a pH in the range of about 1 to about 7, can provide a Brookfield viscosity ranging from about 300 mPa to about 100,000 mPa or more (Brookfield RVT, 20 rpm, at about 25 C ambient room temperature).

The inventive multi-purpose copolymers can be employed as emulsifiers, stabilizers, suspending agents, film formers, conditioners, moisturizers, spreading aids and carriers for enhancing the efficacy, deposition or delivery of chemically and physiologically active ingredients and cosmetic materials, and as vehicles for improving the psychosensory, and aesthetic properties of a formulation in which they are included. The cationic character of the copolymers makes them useful as antistats, and, under certain conditions, may also provide biocidal, bacteriostatic, preservative, and anti-microbial activity. The copolymers can be utilized in a variety of products for personal care, health care, household care, fabric care, institutional and industrial (collectively "I&I") care, and in a variety of products for medical and industrial applications. The copolymers are preferably incorporated in compositions that are non-alkaline, i.e., acidic to substantially neutral in pH, but are not limited thereto.

The amount of copolymer that can be employed depends upon the purpose for which they are included in the formulation and can be readily determined by person skilled in the formulation arts. The instant copolymers of formulae (I) and (II) of the personal care, household care or fabric care compositions preferably comprise no more than about 50 weight percent of the composition; more preferably no more than about 25 weight percent of said composition; even more preferably no more than about 7 weight percent; and still more preferably no more than about 5 weight percent.

The instant copolymers of formulae (I) and (II) of the personal care, household care or fabric care composition preferably comprise at least about 0.0001 weight percent of the said composition, more preferably at least about 0.01 weight percent, even more preferably at least about 0.1 weight percent, and still more preferably at least about 0.2 by weight of the composition.

According to the instant invention, the instant copolymers of formulae (I) and (II) of the personal care, household care or fabric care compositions comprise a weight average molecular weight from about 1,000 to about 10 million Daltons. Another embodiment of the instant invention is the instant copolymers of formulae (I) and (II) of the personal care, household care or fabric care compositions comprise a weight average molecular weight from about 25,000 to about 5 million Daltons. Another embodiment of the instant invention is the instant copolymers of formulae (I) and (II) of the personal care, household care or fabric care compositions comprise a weight average molecular weight from about 40,000 to about 4 million Daltons. Another embodiment of the instant invention is the instant copolymers of formulae (I) and (II) of the personal care, household care or fabric care compositions comprise a weight average molecular weight from about 50,000 to about 2 million Daltons. Another embodiment of the instant invention is the instant copolymers of formulae (I) and (II) of the personal care, household care or fabric care compositions comprise a weight average molecular weight from about 50,000 to about 1 million Daltons. Another embodiment of the instant invention is the instant copolymers of formulae (I) and (II) of the personal care, household care or fabric care compositions comprise a weight average molecular weight from about 50,000 to about 500,000 Daltons. Another embodiment of the instant invention is the instant copolymers of formulae (I) and (II) of the personal care, household care or fabric care compositions comprise a weight average molecular weight from about 50,000 to about 200,000 Daltons.

A copolymer of this invention can be employed as a rheology modifier or emulsion stabilizing agent in conventional emulsion formulations by incorporating the copolymer in the formulation at any step during the formation of an oil-in-water or water-in-oil or multiphase emulsion process. For example, an inventive copolymer, supplied as an aqueous emulsion product, can be included with the water phase components. In one preferred emulsion embodiment, the copolymer is added to the formulation after the final emulsion has formed and cooled, adjusting the pH downward with an organic acid or mineral acid to optimize acid swelling to the desired viscosity, and then adjusting the final composition to the desired pH. If the pH of a completed composition or formulation containing an acid-swollen copolymer is more acidic than required for the intended use of the formulation, the pH can then be further adjusted with any, preferably physiologically tolerable, inorganic or organic base.

Compositions containing said copolymer can be packaged and dispensed from containers, such as jars, bottles, tubes, spray bottles, wipes, cans, roll-on containers, stick containers, and the like, without limitation. There is no limitation as to the form of product in which the copolymer can be incorporated, so long as the purpose for which the product is used is achieved. For example, personal care and health care products containing said copolymer can be applied to the skin, hair, scalp and nails in the form of, without being limited thereto, gels, sprays (liquid or foam), emulsions (creams, lotions, pastes), liquids (rinses, shampoos), bars, ointments, suppositories, impregnated wipes, patches, and the like.

The copolymers of the invention are suitable for the preparation of personal care compositions and products (cosmetics, toiletries, cosmeceuticals) and topical health care products and compositions, including without limitation, hair care products, such as shampoos (including combination shampoos, such as "two-in-one" conditioning shampoos); post-shampoo rinses; setting and style maintenance agents including setting aids, such as gels and sprays, grooming aids, such as pomades, conditioners, perms, relaxers, hair smoothing products, and the like; skin care products (facial, body, hands, scalp and feet), such as creams, lotions, conditioners, and cleansing products; antiacne products; antiaging products (exfoliant, keratolytic, anticellulite, antiwrinkle, and the like); skin protectants such as sunscreens, sunblock, barrier creams, oils, silicones, and the like; skin color products (whiteners, lighteners, sunless tanning accelerators, and the like); hair colorants (hair dyes, hair color rinses, highlighters, bleaches and the like); pigmented skin colorants (face and body makeups, foundation creams, mascara, rouge, lip products, and the like); bath and shower products (body cleansers, body wash, shower gel, liquid soap, soap bars, syndet bars, conditioning liquid bath oil, bubble bath, bath powders, and the like); nail care products (polishes, polish removers, strengtheners, lengtheners, hardeners, cuticle removers, softeners, and the like); and any aqueous acidic to substantially neutral composition to which an effective amount of copolymer can be incorporated for achieving a beneficial or desirable, physical or chemical, effect therein during storage and/or usage.

Toiletries and health and beauty aids, commonly referred to as HBAs, containing said copolymer, can include, without limitation, hair-removal products (shaving creams and lotions, depilatories, after-shave skin conditioners, and the like); deodorants and antiperspirants; oral care products (mouth, teeth and gums), such as mouthwash, dentifrice, such as toothpaste, tooth powder, tooth polishes, tooth whiteners, breath fresheners, denture adhesives, and the like; facial and body hair bleach; and the like. Other health and beauty aids that can contain said copolymers, include, without limitation, sunless tanning applications containing artificial tanning accelerators, such as dihydroxyacetone (DHA), tyrosine, tyrosine esters, and the like; skin depigmenting, whitening, and lightening formulations containing such active ingredients as kojic acid, hydroquinone, arbutin, fruital, vegetal or plant extracts, (lemon peel extract, chamomile, green tea, paper mulberry extract, and the like), ascorbyl acid derivatives (ascorbyl palmitate, ascorbyl stearate, magnesium ascorbyl phosphate, and the like); foot care products, such as keratolytic corn and callous removers, foot soaks, foot powders (medicated, such as antifungal athlete's foot powder, ointments, sprays, and the like, and antiperspirant powders, or non-medicated moisture absorbent powder), liquid foot sprays (non-medicated, such as cooling, and deodorant sprays, and medicated antifungal sprays, antiperspirant sprays, and the like), and foot and toenail conditioners (lotions and creams, nail softeners, and the like).

Topical health and beauty aids that can include copolymers (e.g., as spreading aids and film formers) include, without being limited thereto, skin protective spray, cream, lotion, gel, stick and powder products, such as insect repellants, itch relief, antiseptics, disinfectants, sun blocks, sun screens, skin tightening and toning milks and lotions, wart removal compositions, and the like.

The inventive copolymers are particularly useful as suspending agents for particulates, such as mica, pearlizing agents, beads, and the like, making them suitable for dermal products containing particulates, microabrasives, and abrasives, such as shower gels, masks and skin cleansers containing exfoliative scrub agents. Numerous cosmetically useful particulate exfoliating agents are known in the art, and the selection and amount is determined by the exfoliating effect desired from the use of the composition, as recognized by those skilled in the cosmetic arts. Useful exfoliating agents include, but are not limited to, biological abrasives, inorganic abrasives, synthetic polymers, and the like, and mixtures thereof. Biological abrasives include, without limitation, shell, seed, and kernel or stone granules or powders, obtained from nuts, such as from walnut (Juglans regia) shells, almonds, pecans, and the like; fruital sources, such as apricots, avocados, coconuts, olives, peaches, and the like; vegetal sources, such as corn cob, oat bran, rice, rose hip seed, jojoba (wax, seed powder), microcrystalline cellulose, ground loofa, ground seaweed, and the like; animal sources, such as oyster shell, silk, microcrystalline collagen, and the like. Inorganic abrasives include, without limitation, stannic oxide, talc, silica (hydrated, colloidal and the like), kaolin, precipitated chalk, salts (sodium chloride, dead sea salt, and the like), ground pumice, and the like. Synthetic polymers include, without limitation, microcrystalline polyamides (nylons), microcrystalline polyesters (polycarbonates), and the like. The copolymers of the present invention are also useful for suspending gaseous bubbles in a liquid medium.

The instant copolymers are useful as thickeners and film-formers in a variety of dermatological, cosmeceutical compositions employed for topically ameliorating skin conditions caused by drying, photodamage, aging, acne, and the like, containing conditioners, moisturizers, antioxidants, exfoliants, keratolytic agents, vitamins, and the like, typically containing an active acidic ingredient and having a pH in the range of about 0.5 to about 5. When a copolymer is incorporated into these foregoing acidic product embodiments, the active acid ingredient can serve as both the active skin treatment agent and acid swelling agent for the copolymer to achieve the desired viscosity.

In one cosmeceutical aspect, said copolymer can be employed as a thickener for active skin treatment lotions and creams containing, as active ingredients, acidic anti-aging, anti-cellulite, and anti-acne agents, hydroxy carboxylic acids, such as alpha-hydroxy acid (AHA), beta-hydroxy acid (BHA), alpha-amino acid, alpha-keto acids (AKAs), and mixtures thereof. In such cosmeceuticals, AHAs can include, but are not limited to, lactic acid, glycolic acid, fruit acids, such as malic acid, citric acid, tartaric acid, extracts of natural compounds containing AHA, such as apple extract, apricot extract, and the like, honey extract, 2-hydroxyoctanoic acid, glyceric acid (dihydroxypropionic acid), tartronic acid (hydroxypropanedioic acid), gluconic acid, mandelic acid, benzilic acid, azelaic acid, alpha-lipoic acid, salicylic acid, AHA salts and derivatives, such as arginine glycolate, ammonium glycolate, sodium glycolate, arginine lactate, ammonium lactate, sodium lactate, alpha-hydroxybutyric acid, alpha-hydroxyisobutyric acid, alpha-hydroxyisocaproic acid, alpha-hydroxyisovaleric acid, atrolactic acid, and the like. BHAs can include, but are not limited to, 3-hydroxy propanoic acid, beta-hydroxybutyric acid, beta-phenyl lactic acid, beta-phenylpyruvic acid, and the like. Alpha-amino acids include, without being limited thereto, alpha-amino dicarboxylic acids, such as aspartic acid, glutamic acid, and mixtures thereof, sometimes employed in combination with fruit acid. AKAs include pyruvic acid. In some antiaging compositions, the acidic active agent may be retinoic acid, a halocarboxylic acid, such as trichloroacetic acid, an acidic antioxidant, such as ascorbic acid (vitamin C), a mineral acid, phytic acid, lysophosphatidic acid, and the like. Some acidic anti-acne actives, for example, can include salicylic acid, derivatives of salicylic acid, such as 5 octanoylsalicylic acid, retinoic acid, and its derivatives.

A discussion of the use and formulation of active skin treatment compositions is in COSMETICS & TOILETRIES, C&T Ingredient Resource Series, "AHAs & Cellulite Products How They Work", published 1995, and "Cosmeceuticals", published 1998, both available from Allured Publishing Corporation, incorporated herein by reference. Compositions containing alpha-amino acids acidified with ascorbic acid are described in U.S. Pat. No. 6,197,317, and a commercial cosmeceutical preparation utilizing these acids in an anti-aging, skin care regimen is sold under the trade name, AFAs, by exCel Cosmeceuticals (Bloomfield Hills, Mich.). The term "AFA", as described in the supplier's trade literature, was coined by the developer to describe the amino acid/vitamin C combination as Amino Fruit Acids and as the acronym for "Amino acid Filaggrin based Antioxidants."

Other health care products in which the instant copolymers can be included are medical products, such as topical and non-topical pharmaceuticals, and devices. In the formulation of pharmaceuticals, said copolymer can be employed as a thickener and/or lubricant in such products as creams, pomades, gels, pastes, ointments, tablets, gel capsules, purgative fluids (enemas, emetics, colonics, and the like), suppositories, anti-fungal foams, eye products (ophthalmic products, such as eye drops, artificial tears, glaucoma drug delivery drops, contact lens cleaner, and the like), ear products (wax softeners, wax removers, otitis drug delivery drops, and the like), nasal products (drops, ointments, sprays, and the like), and wound care (liquid bandages, wound dressings, antibiotic creams, ointments, and the like), without limitation thereto.

The film-forming and acid-swellable character of the copolymer makes the copolymer particularly suitable as a vehicle for topical medical compositions for promoting and enhancing the transdermal delivery of active ingredients to or through the skin, for enhancing the efficacy of anti-acne agents formulations and topical analgesics, and for controlling release of drugs, such as antacids from tablets, or syrups, at low pH, such as in the stomach; controlling drug release from tablets, lozenges, chewables, and the like in the mildly acidic environment of the mouth; or from suppositories, ointments, creams, and the like in the mildly acidic environment of the vagina; to promote deposition of dandruff control agents from shampoos, salves, and the like; to enhance the deposition of colorants on skin from pigmented cosmetics (makeups, lipsticks, rouges, and the like) and on hair from hair dyes, and the like.

In addition to the foregoing, the cationic character of the polymers of the present invention at acid pH, and its surprising cationic compatibility, makes the copolymer useful as a thickener for antistatic, biocidal, antimicrobial, and other preservative compositions, in a variety of personal care, health care, I&I, and medical applications. For example, the copolymer can be employed as a thickener in over-the-counter (OTC) health care and pharmaceutical products where cationic biocides are typically employed, such as in oral care compositions for plaque and tartar control, and liquid vehicles containing therapeutic agents, such as syrups, gels, and the like. Under certain controlled pH conditions, the cationic character of the copolymer, itself, may also provide antistatic activity or biocidal, antimicrobial, or like preservative activity.

The copolymers of the present invention can be employed, without being limited thereto, as a lubricant coating for medical devices, such as soft tissue implants, surgical gloves, catheters, cannulae, and the like, as removable protective film coatings for medical instruments, wound dressings, and the like, as a muco-adhesive, especially in the acid environment of the stomach, as a carrier and thickener in formulated products for medical applications, such as disinfectant hand creams, antiviral products (for anionic viruses), antibiotic ointments, sprays and creams, non-drip, sprayable disinfectant in hospitals, hard surface antimicrobial finish applied during routine maintenance, and the like.

The copolymers of the present invention can be used in home care, and I&I applications, for example, as a rheology modifier, fabric conditioning agent, antistatic agent, especially to improve formulation efficiency through "cling-on-surface" or improving efficacy of disinfectants, and biocidal formulations, and to synergistically improve fabric softening efficacy in combination with traditional fabric softeners. Typical household and I&I products that may contain polymers of the invention, include, without being limited thereto, laundry and fabric care products, such as detergents, fabric softeners (liquids or sheets), ironing sprays, dry cleaning aids, antiwrinkle sprays, spot removers and the like; hard surface cleansers for the kitchen and bathroom and utilities and appliances employed or located therein, such as toilet bowl gels, tub and shower cleaners, hard water deposit removers, floor and tile cleansers, wall cleansers, floor and chrome fixture polishes, alkali-strippable vinyl floor cleaners, marble and ceramic cleaners, air freshener gels, liquid cleansers for dishes, and the like; automatic dishwasher detergents and rinses; disinfectant cleaners, such as toilet bowl and bidet cleaners, disinfectant hand soaps, room deodorizers, and the like.

The copolymers of the present invention can be utilized as rheology modifiers, dispersants, stabilizers, promoters, or antimicrobials, and the like, in industrial product applications, such as, without being limited thereto, textiles (processing, finishing, printing, and dyeing aids, protective washable surface coatings, manufacture of synthetic leather by saturation of non-woven fabrics, and the like, manufacturing of woven fabrics, non-woven fabrics, natural and synthetic fibers and the like); water treatments (waste water, cooling water, potable water purification, and the like); chemical spill containments (acid-spill absorbent, and the like); leather and hide processing (processing aids, finishing, coating, embossing, and the like); paper and papermaking (surface coatings, such as pigmented coatings, antistatic coatings, and the like, pulp binders, surface sizings, dry and wet strength enhancers, manufacture of wet-laid felts, and the like); printing (inks, antiwicking ink-jet printer inks, thickeners for ink formulations containing cationic dyes for printing acrylic fabrics, and the like); paints (pigment and grinding additive, crosslinking agent for epoxy latex emulsions, particulate-suspending aid for clays, pigments, and the like); industrial plant effluent treatment (flocculants for phenolics in paper mill effluent, and the like); metal working (acid etch cleaners, low pH metal coatings, pickling agents in cold rolled steel processing, and the like); adhesives (clear adhesives, adhesion promoters for metal, plastic, wood, and the like, non-woven floc adhesive tie coatings, bonding, and the like); wood preservation; and industrial construction products for buildings and roads (cement plasticizers, asphalt emulsion stabilizers at low pH, acid etch for cement, consistency modifiers of concrete, mortar, putty, and the like). The copolymers of the present invention are particularly useful as thickeners for rust removers, acid truck cleaners, scale removers, and the like, and as dispersion stabilizers of products containing particulates, such as clay, pigments (titanium dioxide, calcium carbonate, and other minerals), abrasives, and the like, employed in a variety of the foregoing industrial applications, and in drilling muds.

Products containing copolymers of the present invention can contain various conventional additives and adjuvants known in the art, some of which can serve more than one function. The amounts employed will vary with the purpose and character of the product and can be readily determined by one skilled in the formulation arts and from the literature. The term "cosmetic adjuvant" includes cosmetically and pharmaceutically acceptable product stabilizing and product finishing agents that maintain the physical stability of the composition and its visible aesthetic appearance and market appeal during the useful shelf life of the composition.

The term "fixative" as applied to polymers encompasses the properties of film-formation, adhesion, or coating deposited on a surface on which the polymer is applied. The terms "hair styling and hair fixative" as commonly understood in the hair care arts, and as used herein, refer collectively to hair setting agents that are hair fixatives and film formers and which are topically applied to the hair to actively contribute to the ease of styling and/or holding of a hair set, and to maintain the restylability of the hair set. Hence, hair setting compositions include hair styling, hair fixative, and hair grooming products that conventionally are applied to the hair (wet or dry) in the form of gels, rinses, emulsions (oil-in-water, water-in-oil or multiphase), such as lotions and creams, pomades, sprays (pressurized or non-pressurized), spritzes, foams, such as mousses, shampoos, solids, such as sticks, semisolids and the like, or are applied from a hair setting aid having the hair setting composition impregnated therein or coated thereon, to leave the hair setting agent in contact on the hair for some period until removed, as by washing.

The term "conditioning agents", and grammatical variations thereof, as it relates to compositions for skin care and hair care includes cosmetically and pharmaceutically useful materials that are humectants, moisturizers, and emollients. It is recognized that some conditioning agents can serve more than one function in a composition, such as emulsifying agents, lubricants, and solvents.

A preferred hair care composition embodiment comprises a copolymer of the present invention in an amount effective to provide to the hair care composition a property, such as a hair fixative property, a hair conditioning property, a viscid property (thickening, rheology modifying), or a combination thereof. Optionally, the hair care composition can include one or more auxiliary film-forming agent, auxiliary hair-fixative agent, auxiliary hair conditioning agent, auxiliary rheology modifying agent, or a mixture thereof.

A preferred skin care composition embodiment comprises a copolymer of the present invention in an amount effective to provide to the skin care composition a property, such as a skin conditioning property, a viscid property (thickening, rheology modifying), or a combination thereof. Optionally, the skin care composition can include one or more auxiliary skin conditioning agent, auxiliary rheology modifying agent, or a mixture thereof.

Product formulations comprising a copolymer of this invention can contain various additives and cosmetic adjuvants, conventionally or popularly included in personal care, household care, institutional care, and industrial care products, and in industrial processes, including, without being limited thereto, acidifying or alkalizing pH adjusting agents and buffering agents; auxiliary fixatives and film formers, such as nonionic, anionic, cationic, or amphoteric polymers of synthetic or natural origin, and the like; auxiliary rheology modifiers, such as viscosity-increasing polymeric, gum, or resin thickeners or gellants; additives, such as emulsifiers, emulsion stabilizers, waxes, dispersants, and the like, and viscosity control agents, such as solvents, electrolytes, and the like; auxiliary conditioning agents, such as antistatic agents, synthetic oils, vegetable or animal oils, silicone oils, monomeric or polymeric quaternized ammonium compounds and derivatives thereof, sheen enhancers, moisturizers, emollients, humectants, lubricants, sunscreen agents, and the like; oxidizing agents; reducing agents; surfactants, such as anionic, cationic, nonionic, amphoteric, zwitterionic surfactants, and silicone derivatives thereof; polymer film modifying agents, such as plasticizers, tackifiers, detackifiers, wetting agents, and the like; product stabilizing and finishing agents, such as chelating agents, opacifiers, pearlescing agents, proteinaceous materials and derivatives thereof, vitamins and derivatives thereof, preservatives, fragrances, solubilizers, colorants (temporary or permanent), such as pigments and dyes, UV absorbers, and the like; propellants (water-miscible or water-immiscible), such as fluorinated hydrocarbons, liquid volatile hydrocarbons, compressed gases, and the like; and mixtures thereof.

Additives and adjuvant ingredients, products, or materials, which may be employed with the inventive copolymers discussed herein will be referred to by the international nomenclature commonly referred to as INCI name given them in the International Cosmetic Ingredient Dictionary, published by the Cosmetic, Toiletry, and Fragrance Association, Washington D.C. (hereafter INCI Dictionary), such as can be found in any edition thereof, for example, Volumes 1 and 2, Sixth Edition, (1995) or Volumes 1-3, Seventh and Eighth Editions, (1997, 2000), or by their commonly used chemical names. Numerous commercial suppliers of materials listed by INCI name, trade name or both can be found in the INCI Dictionary and in numerous commercial trade publications, including but not limited to the 2001 McCutcheon's Directories, Volume 1: Emulsifiers & Detergents and Volume 2: Functional Materials, published by McCutcheon's Division, The Manufacturing Confectioner Publishing Co., Glen Rock, N.J. (2001); and 2001 Cosmetic Bench Reference, edition of COSMETICS & TOILETRIES, 115 (13), published by Allured Publishing Corporation, Carol Stream, Ill. (2001); the relevant disclosures of each are incorporated herein by reference. Such components and the formulation of compositions are also described in detail in well known references, such as Cosmetics Science and Technology, First Edition (Sagarin (ed)), published 1957, and Second Edition (Balsam, et al. (eds)), published 1972-74; and The Chemistry and Manufacture of Cosmetics, Second Edition (deNavarre (ed)), published 1975, and Third Edition (Schlossman (ed)), published 2000, both available from Allured Publishing Corporation; Rieger (ed), Harry's Cosmeticology, 8th Edition, Chemical Publishing, Co., Inc., New York, N.Y. (2000); and various formularies available to those skilled in the pharmaceutical arts, such as Remington's Pharmaceutical Sciences, Fourteenth Edition, Mack Publishing Company, Easton, Pa. (1970); the relevant disclosures of each are incorporated herein by reference.

It is known that formulated compositions for personal care and topical, dermatological, health care, which are applied to the skin and mucous membranes for cleansing or soothing, are compounded with many of the same or similar physiologically tolerable ingredients and formulated in the same or similar product forms, differing primarily in the purity grade of ingredient selected, by the presence of medicaments or pharmaceutically accepted compounds, and by the controlled conditions under which products may be manufactured. Likewise, many of the ingredients employed in products for households, and I&I are the same or similar to the foregoing, differing primarily in the amounts and material grade employed. It is also known that the selection and permitted amount of ingredients also may be subject to governmental regulations, on a national, regional, local, and international level. Thus, discussion herein of various useful ingredients for personal care and health care products may apply to household and I&I products and industrial applications.

The choice and amount of ingredients in formulated compositions containing an inventive copolymer will vary depending on the product and its function. Formulation ingredients for personal care and topical health care products typically can include, but are not limited to, solvents, surfactants (as cleansing agents, emulsifying agents, foam boosters, hydrotropes, solubilizing agents, and suspending agents), nonsurfactant suspending agents, emulsifiers, skin conditioning agents (emollients, humectants, moisturizers, and the like), hair conditioning agents, hair fixatives, film-formers, skin protectants, binders, chelating agents, antimicrobial agents, antifungal agents, antidandruff agents, abrasives, adhesives, absorbents, dyes, deodorant agents, antiperspirant agents, opacifying and pearlescing agents, antioxidants, preservatives, propellants, spreading aids, sunscreen agents, sunless skin tanning accelerators, ultraviolet light absorbers, pH adjusting agents, botanicals, hair colorants, oxidizing agents, reducing agents, skin bleaching agents, pigments, physiologically active agents, anti-inflammatory agents, topical anesthetics, fragrance and fragrance solubilizers, and the like, in addition to ingredients previously discussed that may not appear herein. Oral care products, for example, can contain anticaries, antitartar and/or antiplaque agents in addition to surfactants, abrasives, humectants, and flavorants. An extensive listing of substances and their conventional functions and product categories appears in the INCI Dictionary, generally, and in Vol. 2, Sections 4 and 5 of the Seventh Edition, in particular, incorporated herein by reference.

The copolymers of the present invention prepared as aqueous emulsions are particularly useful for water-based formulations, and formulations containing water-miscible auxiliary solvents, but are not limited thereto. Useful solvents commonly employed are typically liquids, such as water (deionized, distilled or purified), alcohols, polyols, and the like, and mixtures thereof. Non-aqueous or hydrophobic auxiliary solvents are commonly employed in substantially water-free products, such as nail lacquers, aerosol propellant sprays, or for specific functions, such as removal of oily soils, sebum, make-up, or for dissolving dyes, fragrances, and the like, or are incorporated in the oily phase of an emulsion. Non-limiting examples of auxiliary solvents, other than water, include linear and branched alcohols, such as ethanol, propanol, isopropanol, hexanol, and the like; aromatic alcohols, such as benzyl alcohol, cyclohexanol, and the like; saturated C12-C30 fatty alcohol, such as lauryl alcohol, myristyl alcohol, cetyl alcohol, stearyl alcohol, behenyl alcohol, and the like. Non-limiting examples of polyols include polyhydroxy alcohols, such as glycerin, propylene glycol, butylene glycol, hexylene glycol, C2-C4 alkoxylated alcohols and C2-C4 alkoxylated polyols, such as ethoxylated, propoxylated, and butoxylated ethers of alcohols, diols, and polyols having about 2 to about 30 carbon atoms and 1 to about 40 alkoxy units, polypropylene glycol, polybutylene glycol, and the like. Non-limiting examples of non-aqueous auxiliary solvents include silicones, and silicone derivatives, such as cyclomethicone, and the like, ketones such as acetone and methylethyl ketone; natural and synthetic oils and waxes, such as vegetable oils, plant oils, animal oils, essential oils, mineral oils, C7-C40 isoparaffins, alkyl carboxylic esters, such as ethyl acetate, amyl acetate, ethyl lactate, and the like, jojoba oil, shark liver oil, and the like. Some of the foregoing non-aqueous auxiliary solvents may also be conditioners and emulsifiers.

Surfactants are generally employed as cleansing agents, emulsifying agents, foam boosters, hydrotropes and suspending agents. The copolymers of the present invention may be employed in formulations containing all classes of surfactants, i.e., anionic surfactants, cationic surfactants, nonionic surfactants, amphoteric surfactants. The term "amphoteric surfactant" as used herein includes zwitterionic surfactants. In addition to the foregoing references, discussions of the classes of surfactants are in Cosmetics & Toiletries C&T Ingredient Resource Series, "Surfactant Encyclopedia", 2nd Edition, Rieger (ed), Allured Publishing Corporation (1996); Schwartz, et al., Surface Active Agents, Their Chemistry and Technology, published 1949; and Surface Active Agents and Detergents, Volume II, published 1958, Interscience Publishers; each incorporated herein by reference.

Surprisingly, the copolymers of the present invention are useful as thickeners and deposition aids in compositions containing a relatively high concentration (about 10-40 weight percent) of anionic surfactant, such as shampoos and two-in-one type liquid conditioning/cleansers for hair and body (bath) products. The present copolymers are compatible with cationic surfactants having antistatic activity, such as are employed in hair care products and fabric care products.

Anionic surfactants include substances having a negatively charged hydrophobe or that carry a negative charge when the pH is elevated to neutrality or above, such as acylamino acids, and salts thereof, for example, acylglutamates, acyl peptides, sarcosinates, and taurates; carboxylic acids, and salts thereof, for example, alkanolic acids and alkanoates, ester carboxylic acids, and ether carboxylic acids; phosphoric acid ester and salts thereof; sulfonic acids and salts thereof, for example, acyl isethionates, alkylaryl sulfonates, alkyl sulfonates, and sulfosuccinates; and sulfuric acid esters, such as alkyl ether sulfates and alkyl sulfates.

Non-limiting examples of anionic surfactants include mono-basic salts of acylglutamates that are slightly acidic in aqueous solution, such as sodium acylglutamate and sodium hydrogenated tallow glutamate; salts of acyl-hydrolyzed protein, such as potassium, palmitoyl hydrolyzed milk protein, sodium cocoyl hydrolyzed soy protein, and TEA-abietoyl hydrolyzed collagen; salts of acyl sarcosinates, such as ammonium myristoyl sarcosine, sodium cocoyl sarcosinate, and TEA-lauroyl sarcosinate; salts of sodium methyl acyltaurates, such as sodium lauroyl taurate and sodium methyl cocoyl taurate; alkanoic acids and alkanoates, such as fatty acids derived from animal and vegetable glycerides that form water-soluble soaps and water-insoluble emulsifying soaps, including sodium stearate, aluminum stearate, and zinc undecylenate; ester carboxylic acids, such as dinonoxynol-9-citrate; salts of acyl lactylates such as calcium stearoyl lactylate and laureth-6 citrate; ethercarboxylic acids derived from ethyoxylated alcohols or phenols having varying lengths of polyoxyethylene chains, such as nonoxynol-8 carboxylic acid, and sodium trideceth-13 carboxylate; mono- and di-esters of phosphoric acid and their salts, such as phospholipids, dilaureth-4-phosphate, DEA-oleth-10 phosphate and triethanolamine lauryl phosphate; salts of acylisethionate, such as sodium cocoyl isethionate; alkylarylbenzene sulfonates, such as alpha-olefin sulfonate (AOS) and alkali metal, alkaline earth metal, and alkanolamine salts thereof, and sodium dodecylbenzene sulfonate; alkyl sulfonates, such as sodium C12-C14 olefin sulfonate, sodium cocomonoglyceride sulfonate, sodium C12-C15 pareth-15 sulfonate, and sodium lauryl sulfoacetate; sulfosuccinates, such as mono- and di-esters of sulfosuccinic acid, salts thereof and alkoxylated alkyl and alkylamido derivatives thereof, such as di-C4-C10 alkyl sodium sulfosuccinate, disodium laureth sulfosuccinate, disodium oleamido MEA-sulfosuccinate, and disodium C12-C15 pareth sulfosuccinate; alkyl ether sulfates, such as sodium and ammonium lauryl ether sulfate (having about 1 to about 12 moles ethylene oxide); alkyl sulfates, such as sodium, ammonium and triethanolamine salts of C12-C18 alkylsulfates, sodium C12-C14 olefin sulfates, sodium laureth-6 carboxylate, sodium C12-C18 pareth sulfate, and the like.

Cationic surfactants can have a hydrophobe that carries a positive charge or that is uncharged at pH values close to neutrality or lower, such as alkylamines, alkyl imidazolines, ethoxylated amines, and quaternary ammonium compounds. Cationic surfactants used in cosmetics are preferably N-derivatives and the neutralizing anion may be inorganic or organic. Among the cationic surfactant materials useful herein are quaternary ammonium compounds corresponding to the general formula: (R10R11R12R13N30)E-, wherein each of R10, R11, R12, and R13 are independently selected from an aliphatic group having from 1 to about 22 carbon atoms, or an aromatic, alkoxy, polyoxyalkylene, alkylamido, hydroxyalkyl, aryl or alkylaryl group having 1 to about 22 carbon atoms in the alkyl chain; and E- is a salt-forming anion such as those selected from halogen, (e.g. chloride, bromide), acetate, citrate, lactate, glycolate, phosphate, nitrate, sulfate, and alkylsulfate. The aliphatic groups can contain, in addition to carbon and hydrogen atoms, ether linkages, ester linkages, and other groups such as amino groups. The longer chain aliphatic groups, e.g., those of about 12 carbons, or higher, can be saturated or unsaturated.

Alkylamines can be salts of primary, secondary and tertiary fatty C12-C22 alkylamines, substituted or unsubstituted, and substances sometimes referred to as "amidoamines". Non-limiting examples of alkyl amines and salts thereof include dimethyl cocamine, dimethyl palmitamine, dioctylamine, dimethyl stearamine, dimethyl soyamine, soyamine, myristyl amine, tridecyl amine, ethyl stearylamine, N-tallowpropane diamine, ethoxylated stearylamine, dihydroxy ethyl stearylamine, arachidylbehenylamine, dimethyl lauramine, stearylamine hydrochloride, soyamine chloride, stearylamine formate, N-tallowpropane diamine dichloride, and amodimethicone (INCI name for a silicone polymer and blocked with amino functional groups, such as aminoethylamino propylsiloxane). Non-limiting examples of amidoamines and salts thereof include stearamido propyl dimethyl amine, stearamidopropyl dimethylamine citrate, palmitamidopropyl diethylamine, and cocamidopropyl dimethylamine lactate. Other cationic surfactants include distearyldimonium chloride, dicetyidimonium chloride, guar hydroxypropyltrimonium chloride, and the like. At low pH, amine oxides may protonate and behave similarly to N-alkyl amines.

Non-limiting examples of alkyl imidazolines include alkyl hydroxyethyl imidazoline, such as stearyl hydroxyethyl imidazoline, coco hydroxyethyl imidazoline, ethyl hydroxymethyl oleyl oxazoline, and the like. Non-limiting examples of ethyoxylated amines include PEG-cocopolyamine, PEG-15 tallow amine, quaternium-52, and the like.

Quaternary ammonium compounds are monomeric or polymeric materials containing at least one nitrogen atom that is linked covalently to four alkyl and/or aryl substituents, and the nitrogen atom remains positively charged regardless of the environmental pH. Quaternary ammonium compounds comprise a large number of substances that are used extensively as surfactants, conditioners, antistatic agents, and antimicrobial agents and include, alkylbenzyldimethyl ammonium salts, alkyl betaines, heterocyclic ammonium salts, and tetraalkylammonium salts. Long-chain (fatty) alkylbenzyldimethyl ammonium salts are preferred as conditioners, as antistatic agents, and as fabric softeners, discussed in more detail below. Other quaternary ammonium compounds include quaternary ammonium silicones.

Non-limiting examples of alkylbenzyldimethylammonium salts include stearalkonium chloride, benzalkonium chloride, quaternium-63, olealkonium chloride, didecyldimonium chloride, and the like. Alkyl betaine compounds include alkylamidopropyl betaine, alkylamidopropyl hydroxysultaine, and sodium alkylamido propyl hydroxyphostaine. Non-limiting examples of alkyl betaine compounds include oleyl betaine, coco-betaine, cocoamidopropyl betaine, coco-hydroxy sultaine, coco/oleamidopropyl betaine, coco-sultaine, cocoamidopropylhydroxy sultaine, and sodium lauramidopropyl hydroxyphostaine. Heterocyclic ammonium salts include alkylethyl morpholinium ethosulfate, isostearyl ethylimidonium ethosulfate, and alkylpyridinium chlorides, and are generally used as emulsifying agents. Non-limiting examples of heterocyclic ammonium salts include cetylpyridinium chloride, isostearylethylimidonium ethosulfate, and the like. Non-limiting examples of tetraalkylammonium salts include cocamidopropyl ethyldimonium ethosulfate, hydroxyethyl cetyidimonium chloride, quaternium-18, and cocodimonium hyroxypropyl hydrolyzed protein, such as hair keratin, and the like.

The copolymers of the present invention are surprisingly compatible with cationic surfactants and other cationic compounds suitable as antistatic agents. The term "antistatic agents" refers to ingredients that alter the electrical properties of cosmetic raw materials or of human body surfaces (skin, hair, etc.) and textiles, for example, by reducing their tendency to acquire an electrical charge and thus, can condition hair, skin and fabrics. The cationic compatibility of the copolymers makes them suitable for incorporation into formulations containing antistatic agents typically employed in hair care compositions, such as shampoos, post-shampoo conditioning rinses, hair sprays, hair dressings and the like. The antistatic agent can be employed in amounts up to about 30 weight percent of the final composition, but is not limited thereto.

Antistatic agents include, but are not limited to, quaternary ammonium compounds, protein derivatives, synthetic quaternary ammonium polymers, amines, protonated amine oxides, betaines, and the like, which may act as antistatic agents in specific formulations and under controlled pH conditions in addition to any surfactant properties imparted by such materials. In addition to antistatic agents previously discussed, non-limiting examples of quaternary ammonium compounds useful as antistatic agents are acetamidopropyl trimonium chloride, behenamidopropyl dimethylamine, behenamidopropyl ethyldimonium ethosulfate, behentrimonium chloride, cetethyl morpholinium ethosulfate, cetrimonium chloride, cocoamidopropyl ethyldimonium ethosulfate, dicetyldimonium chloride, dimethicone hydroxypropyl trimonium chloride, hydroxyethyl behenamidopropyl dimonium chloride, quaternium-26, quaternium-27, quaternium-53, quaternium-63, quaternium-70, quaternium-72, quaternium-76 hydrolyzed collagen, PPG-9 diethylmonium chloride, PPG-25 diethylmonium chloride, PPG-40 diethylmonium chloride, stearalkonium chloride, stearamidopropyl ethyl dimonium ethosulfate, steardimonium hydroxypropyl hydrolyzed wheat protein, steardimonium hydroxypropyl hydrolyzed collagen, wheat germamidopropalkonium chloride, wheat germamidopropyl ethyldimonium ethosulfate, and the like.

Synthetic quaternary ammonium polymers, include film-forming polymers and conditioning polymers. Non-limiting examples of synthetic quaternary ammonium polymers include polymers and copolymers of dimethyl diallyl ammonium chloride, such as polyquaternium-4, polyquaternium-6, polyquaternium-7, polyquaternium-22, polyquaternium-10, polyquaternium-11 polyquaternium-15, polyquaternium-16, polyquaternium-24, polyquaternium-28, polyquaternium-32, polyquaternium-33, polyquaternium-35, polyquaternium-37, polyquaternium-39, polyquaternium-44, PEG-2-cocomonium chloride, quaternium-52, and the like.

The term "hair setting composition" encompasses products comprising at least one copolymer of the present invention as a hair setting agent, which are applied to the hair (wet or dry) before, during or after configuring the hair into the shape (curly or straight) desired, without limitation as to product form.

The copolymers of the present invention are surprisingly useful in hair setting and hair styling compositions as the sole film-forming, rheology modifying, conditioning fixative agent. The copolymers of the present invention are also useful in combination with commercially available auxiliary hair fixative polymers, such as nonionic, cationic, and amphoteric hair setting polymers, cationic conditioning polymers, and combinations thereof. It is surprisingly found that unexpectedly increased viscosity and hair setting efficacy properties are produced by appropriate combinations of a polymer of the present invention with an auxiliary conventional hair fixative and/or hair conditioning polymer. Conventional polymeric hair fixative and hair styling polymers, well known in the art, include natural gums and resins and neutral or anionic polymers of synthetic origin. Listings of commercially available hair fixative and conditioning fixative polymers can be readily found in the INCI Dictionary, in supplier websites, and in the trade literature. See, for example, the Polymer Encyclopedia published in Cosmetics & Toiletries, 117(12), December 2002 (Allured Publishing Corporation, Carol Stream, Ill.), the relevant disclosures of which are incorporated herein by reference.

Suitable commercially available nonionic polymers (i.e., neutral) used as hair styling or fixative polymers include, without limitation thereto, polyvinylpyrrolidone (PVP), polyvinylpyrrolidone/vinylacetate copolymer (PVPNA), and the like. Commercially available cationic fixative polymers include, without limitation thereto, polymers having the INCI name, polyquaternium, such as polyquaternium-4, a diallyldimonium chloride/hydroxyethylcellulose copolymer (such as CELQUAT H-100, National Starch); polyquaternium-11, a quaternized vinyl pyrrolidone/dimethylaminoethyl methacrylate copolymer (such as GAFQUAT 734, 755, 755N, ISP); polyquaternium-16, a quaternized vinyl pyrrolidone/vinylimidazolium chloride copolymer (such as LUVIQUAT FC-370, BASF); polyquaternium-28, a vinylpyrrolidone/methacrylamidopropyl-trimethylammonium chloride copolymer (such as GAFQUAT HS-100, ISP); polyquaternium-46, a quaternized vinylcaprolactam/vinylpyrrolidone/methyl-vinylimidazolium methosulfate copolymer; polyquaternium-55, a quaternized vinylpyrrolidone/dimethylaminopropylmethylacrylamide/lauryldimethylpropyl-methacrylamidoammonium chloride copolymer (such as STYLEZE W, ISP), and the like; and amino-substituted polymers which are cationic under acidic pH conditions, such as vinylcaprolactam/PVP/dimethylaminoethylmeth-acrylate copolymer (such as GAFFIX VC-713, ISP); PVP/dimethylaminoethylmethacrylate copolymer (such as Copolymer 845, ISP), PVP/DMAPA acrylates copolymer (such as STYLEZE CC-10, ISP), the pyrrolidone carboxylic acid salt of chitosan, having the INCI name, Chitosan PCA (such as KYTAMER PC, Amerchol), and the like.

Suitable amphoteric fixative polymers include, without limitation thereto, octylacryamide/acrylates/butylaminoethylmethacrylate copolymer (such as the AMPHOMER polymers, National Starch), acrylates/lauryl acrylate/stearyl acrylate/ethylamine oxide methacrylate copolymers (such as the DIAFORMER polymers, Clariant Corp.), and the like.

Suitable commercial conditioning polymers include polymeric quaternary ammonium salts such as, without being limited thereto, polyquaternium-7, a polymeric quaternary ammonium salt of acrylamide and dimethyl diallylammonium chloride monomers (such as MACKERNIUM-007, Mcintyre Group, Ltd.); polyquaternium-10, a polymeric quaternary ammonium salt of hydroxyethylcellulose reacted with a trimethylammonium substituted epoxide (such as the UCARE Polymers JR, LK, LR, SR series, Amerchol and CELQUAT SC series, National Starch); polyquaternium-39, a polymeric quaternary ammonium salt of acrylic acid, diallyl dimethylammonium chloride and acrylamide (such as the MERQUAT and MERQUAT Plus polymers, Ondeo Nalco); quaternized derivatives of natural gums, e.g., guar hydroxypropyltrimonium chloride (such as the JAGUAR and JAGUAR Excel polymers, Rhodia, Inc.), and the like.

A number of quaternary ammonium compounds are used for fabric conditioning and fabric care, generally referred to as fabric softening agents, and are typically employed in amounts of up to about 20 weight percent of the total weight of the formulation, but are not limited thereto. Fabric softening agents useful in combination with the instant copolymers of the present invention generally include long-chain alkylated quaternary ammonium compounds such as dialkyldimethyl quaternary ammonium compounds, imidazoline quaternary compounds, amidoamine quaternary compounds, dialkyl ester quat derivatives of dihydroxypropyl ammonium compounds; dialkyl ester quat derivatives of methyltriethanol ammonium compounds, ester amide amine compounds, and diester quat derivatives of dimethyldiethanol ammonium chloride, as described in the review article by Whalley, "Fabric Conditioning Agents", HAPPI, pp. 55-58 (February 1995), incorporated herein by reference.

In addition to the previously discussed antistatic agents, non-limiting examples of dialkyldimethyl quaternary ammonium compounds, include N,N-dioleyl-N,N-dimethylammonium chloride, N,N-ditallowyl-N,N-dimethylammonium ethosulfate, N,N-di(hydrogenated-tallowyl)-N,N-dimethylammonium chloride, and the like. Non-limiting examples of imidazoline quaternary compounds include 1-N-methyl-3-N-tallowamidoethylimidazolium chloride, 3-methyl-1-tallowylamidoethyl-2-tallowylimidazolinium methylsulfate, available from Witco Chemical Company under the tradename VARISOFT 475, and the like. Non-limiting examples of amidoamine quaternary compounds include N-alkyl-N-methyl-N,N-bis(2-tallowamidoethyl)ammonium salts where the alkyl group can be methyl, ethyl, hydroxyethyl, and the like. Non-limiting examples of dialkyl ester quat derivatives of dihydroxypropyl ammonium compounds include 1,2-ditallowoyloxy-3-N,N,N-trimethylammoniopropane chloride, 1,2-dicanoloyloxy-3-N,N,N-trimethylammoniopropane chloride, and the like.

In addition, other types of long chain (e.g. natural oil and fatty acid-derived) alkylated quaternary ammonium compounds are suitable fabric softening agents, including, but not limited, to N,N-di(alkyloxyethyl)-N,N-dimethylammonium salts such as N,N-di(tallowyloxyethyl)-N,N-dimethylammonium chloride, N,N-di(canolyloxyethyl)-N,N-dimethylammonium chloride, and the like; N,N-di(alkyloxyethyl)-N-methyl-N-(2-hydroxyethyl)ammonium salts such as N,N-di(tallowyloxyethyl)-N-methyl-N-(2-hydroxyethyl) ammonium chloride, N,N-di(canolyloxyethyl)-N-methyl-N-(2-hydroxyethyl)ammonium chloride, and the like; N,N-di(2-alkyloxy-2-oxoethyl)-N,N-dimethylammonium salts, such as N,N-di(2-tallowyloxy-2-oxoethyl)-N,N-dimethylammonium chloride, N,N-di(2-canolyloxy-2-oxoethyl)-N,N-dimethylammonium chloride, and the like; N,N-di(2-alkyloxyethylcarbonyloxyethyl)-N,N-dimethylammonium salts, such as N,N-di(2-tallowyloxyethylcarbonyloxyethyl)-N,N-dimethylammonium chloride, N,N-di(2-canolyloxyethylcarbonyloxyethyl)-N,N-dimethylammonium chloride, and the like; N-(2-alkanoyloxy-2-ethyl)-N-(2-alkyloxy-2-oxoethyl)-N,N-dimethyl ammonium salts, such as N-(2-tallowoyloxy-2-ethyl)-N-(2-tallowyloxy-2-oxoethyl)-N,N-dimethyl ammonium chloride, N-(2-canoloyloxy-2-ethyl)-N-(2-canolyloxy-2-oxoethyl) N,N dimethyl ammonium chloride, and the like; N,N,N-tri(alkyloxyethyl)-N-methyl ammonium salts, such as N,N,N-tri(tallowyloxyethyl)-N-methylammonium chloride, N,N,N-tri(canolyloxyethyl)-N-methylammonium chloride, and the like; N-(2-alkyloxy-2-oxoethyl)-N-alkyl-N,N-dimethyl ammonium salts, such as N-(2-tallowyloxy-2-oxoethyl)-N-tallowyl-N,N-dimethyl ammonium chloride, N-(2-canolyloxy-2-oxoethyl)-N-canolyl-N,N-dimethyl ammonium chloride, and the like.

Preferably, the long-chain alkyl groups are derived from tallow, canola oil, or from palm oil, however, other alkyl groups derived from soybean oil and coconut oil, for example, are also suitable, as are lauryl, oleyl, ricinoleyl, stearyl, paimityl, and like fatty alkyl groups. The quaternary ammonium salt compounds can have any anionic group as a counter-ion, for example, chloride, bromide, methosulfate (i.e. methylsulfate), acetate, formate, sulfate, nitrate, and the like.

Examples of preferred quaternary ammonium fabric softening compounds include N-methyl-N,N-bis(tallowamidoethyl)-N-(2-hydroxyethyl)ammonium methylsulfate and N-methyl-N,N-bis(hydrogenated-tallowamidoethyl)-N-(2-hydroxyethyl) ammonium methylsulfate, each of which materials are available from Witco Chemical Company under the trade names VARISOFT 222 and VARISOFT 110, respectively; dialkyl esterquat derivatives of methyltriethanol ammonium salts such as the DEHYQUART AU series of bis(acyloxyethyl)hydroxyethylmethylammonium methosulfate esterquats available from Cognis, such as DEHYQUART AU35, AU46, AU56, and the like; and N,N-di(tallowoyloxyethyl)-N,N-dimethylammonium chloride, where the tallow chains are at least partially unsaturated. Other preferred fabric softening agents include the well-known dialkyldimethyl ammonium salts such as N,N-ditallowyl-N,N-dimethyl ammonium methylsulfate, N,N-di(hydrogenatedtallowyl)-N,N-dimethyl ammonium chloride, N,N-distearyl-N,N-dimethyl ammonium chloride, N,N-dibehenyl-N,N-dimethylammonium chloride, N,N-di(hydrogenated tallow)-N,N-dimethyl ammonium chloride (trade name ADOGEN 442), N,N-ditallowyl-N,N-dimethyl ammonium chloride (trade name ADOGEN 470, PRAEPAGEN 3445), N,N-distearyl-N,N-dimethyl ammonium chloride (trade name AROSURF TA-100), all available from Witco Chemical Company; N,N-dibehenyl-N,N-dimethyl ammonium chloride, sold under the trade name KEMAMINE Q-2802C by Humko Chemical Division of Witco Chemical Corporation; and N,N-dimethyl-N-stearyl-N-benzylammonium chloride sold under the trade names VARISOFT SDC by Witco Chemical Company and AMMONYX 490 by Onyx Chemical Company.

Any of the foregoing fabric softening agents, and mixtures thereof, can be utilized in combination with the instant copolymers of the present invention, particularly in laundry and fabric care products. For ester-containing fabric softening agents, the pH of the compositions can influence the stability of the fabric softening agents, especially in prolonged storage conditions. The pH, as defined in the present context, is measured in the neat compositions at about 20 C. Preferably, the pH of the composition is less than about 7. For optimum hydrolytic stability of these compositions, the pH is preferably in the range of from about 2 to about 5, more preferably about 2.5 to about 3.5.

In addition to protein derivatives previously described, non-limiting examples of protein derivatives include cocodimonium hydroxypropyl hydrolyzed casein, cocodimonium hydroxypropyl hydrolyzed collagen, cocodimonium hydroxypropyl hydrolyzed hair keratin, cocodimonium hydroxypropyl hydrolyzed rice protein, cocodimonium hydroxypropyl hydrolyzed silk, cocodimonium hydroxypropyl hydrolyzed soy protein, cocodimonium hydroxypropyl hydrolyzed wheat protein, cocodimonium hydroxypropyl hydrolyzed silk amino acids, hydroxypropyl trimonium hydrolyzed collagen, hydroxypropyl trimonium hydrolyzed keratin, hydroxypropyl trimonium hydrolyzed silk, hydroxypropyl trimonium hydrolyzed rice bran, hydroxypropyl trimonium hydrolyzed soy protein, hydroxypropyl trimonium hydrolyzed vegetable protein, hydroxypropyl trimonium hydrolyzed wheat protein, soyethyldimonium ethosulfate, soyethyl morpholinium ethosulfate, and the like.

Nonionic surfactants are generally uncharged amphiphiles and usually are alkoxylated to varying degrees. Classes of nonionic surfactants include alcohols, alkanolamides, amine oxides, esters, and ethers. Nonionic alcohols are usually hydroxy derivatives of long-chain C8-C18 alkane hydrocarbons, such as cetearyl alcohol, hydrogenated tallow alcohol, lanolin alcohols, alkanolamides, and the like. Alkanolamides contain at least one alkoxyl or one polyoxyethylene grouping and include alkanol-derived amides, such as acylamide DEA, N-alkyl pyrrolidone, palmamide MEA, peanutamide MIPA, and the like and ethoxylated amides, such as PEG-50 tallow amide. Amine oxides include alkylamine oxides, such as lauramine oxide; and acylamidopropyl morpholine oxides, such as cocamidopropylamine oxide; and the like. Esters include ethoxylated carboxylic acids, such as PEG-8 dilaurate, PEG-8 laurate, and the like; ethoxylated glycerides, such as PEG-4 castor oil, PEG-1 20 glyceryl stearate, triolein PEG-6 esters, and the like; glycol esters and derivatives thereof, such as glycol stearate SE, propylene glycol ricinoleate, and the like; monoglycerides, such as glyceryl myristate, glyceryl palmitate lactate, and the like; polyglyceryl esters, such as polyglyceryl-6-distearate, polyglyceryl-4 oleyl ether, and the like, polyhydric alcohol esters and ethers, such as methyl gluceth-20 sesquistearate, sucrose distearate; and the like; sorbitan/sorbitol esters, such as polysorbate-60, sorbitan sequiisostearate, and the like; and triesters of phosphoric acid, such as trideceth-3 phosphate, trioleth-8 phosphate, and the like. Ethers include ethoxylated alcohols, such as ceteareth-10, nonoxynol-9, and the like; ethoxylated lanolin, such as PEG-20 lanolin, PPG-12-PEG-65 lanolin oil, and the like; ethoxylated polysiloxanes, such as dimethicone copolyol, and the like; propoxylated POE ethers, such as meroxapol 314, poloxamer 122, PPG-5-ceteth-20, and the like; and alkyl polyglycosides, such as lauryl glucose, and the like.

Nonionic surfactants can be used as emulsifiers, suspending agents, solubilizers, foam boosters, and in some cases, as hydrotropes. Non-limiting examples of generally preferred nonionic surfactants include linear or branched alcohol ethoxylates, C8-C12 alkylphenol alkoxylates, such as octylphenol ethoxylates, polyoxyethylene polyoxypropylene block copolymers, and the like; C8-C22 fatty acid esters of polyoxyethylene glycol mono- and di-glycerides; sorbitan esters and ethoxylated sorbitan esters; C8-C22 fatty acid glycol esters; block copolymers of ethylene oxide and propylene oxide; and the like. Non-limiting examples of surfactant foam boosters or hydrotropes include alkanolamides, such as acetamide MEA, monoethanolamide, diethanolamide, cocamide DEA, isopropanolamide, and the like; amine oxides, such as hydrogenated tallowamine oxide; short chain alkyl aryl sulfonates, such as sodium toluene sulfonate; sulfosuccinates; such as disodium stearyl sulfosuccinate; and the like.

Amphoteric and zwitterionic surfactants are those compounds that have the capacity of behaving either as an acid or a base, by carrying a positive charge in strongly acidic media, carrying a negative charge in strongly basic media, and forming zwitterionic species at intermediate pH. The major classes of amphoteric surfactants are acyl/dialkyl ethylenediamines and derivatives thereof, such as disodium cocoamphocarboxymethylhydroxy-propyl sulfate, disodium cocamphodipropionate, sodium cocoamphoacetate, sodium lauroampho PG-acetatephosphate, sodium tallowamphopropionate, sodium undecylenoamphopropionate, and the like; and N-alkylamino acids, such as aminopropyl laurylglutamide, dihydroxyethyl soya glycinate, lauraminopropionic acid, and the like.

Some suitable zwitterionic surfactants for use in the present compositions include those broadly described as derivatives of aliphatic quaternary ammonium, phosphonium, and sulfonium compounds, wherein which the aliphatic radicals can be straight chain or branched, and wherein one of the aliphatic substituents contains about 8 to about 18 carbon atoms and another substituent contains an anionic water-solubilizing group, such as carboxy, sulfonate, sulfate, phosphate, phosphonate, and the like. Classes of zwitterionics include alkylamino sulfonates, alkyl betaines and alkylamido betaines, such as stearamidopropyldimethylamine, diethylaminoethylstearamide, dimethylstearamine, dimethylsoyamine, soyamine, myristylamine, tridecylamine, ethylstearylamine, N-tallowpropane diamine, ethoxylated (5 moles ethylene oxide) stearylamine, dihydroxy ethyl stearylamine, arachidylbehenylamine, and the like. Some suitable betaine surfactants include but are not limited to alkyl betaines, alkyl amidopropyl betaines, alkyl sulphobetaines, alkyl glycinates, alkyl carboxyglycinates, alkyl amphopropionates, alkyl amidopropyl hydroxysultaines, acyl taurates, and acyl glutamates, wherein the alkyl and acyl groups have from 8 to 18 carbon atoms. Non-limiting examples of preferred amphoteric surfactants include cocamidopropyl betaine, sodium cocoamphoacetate, cocamidopropyl hydroxysultaine, and sodium cocoamphopropionate, which are particularly suitable as mild-type cleansers for skin and hair.

A pH adjusting agent can be added either to a previously acid-swollen, or water-swollen copolymer or to a formulation containing said instant copolymer. Thus, the pH adjusting agent can be utilized in any amount necessary to obtain a desired pH value in the final composition. Non-limiting examples of alkaline pH adjusting agents include alkali metal hydroxides, such as sodium hydroxide, and potassium hydroxide; ammonium hydroxide; organic bases, such as triethanolamine, diisopropylamine, dodecylamine, diisopropanolamine, aminomethyl propanol, cocamine, oleamine, morpholine, triamylamine, triethylamine, tromethamine (2-amino-2-hydroxymethyl)-1,3-p-ropanediol), and tetrakis (hydroxypropyl)ethylenediamine; and alkali metal salts of inorganic acids, such as sodium borate (borax), sodium phosphate, sodium pyrophosphate, and the like, and mixtures thereof. Acidic pH adjusting agents can be organic acids, including amino acids, and inorganic mineral acids. Non-limiting examples of acidic pH adjusting agents include acetic acid, citric acid, fumaric acid, glutamic acid, glycolic acid, .alpha.-hydroxy carboxylic acids containing more than two carbon atoms, hydrochloric acid, lactic acid, nitric acid, phosphoric acid, sodium bisulfate, sulfuric acid, tartaric acid, and the like, and mixtures thereof. In one aspect of the invention, all organic acids (except glycolic acid) are contemplated for use as pH adjusting agents.

Following neutralization with an acidic pH adjusting agent to achieve a desired amount of cationic polymer swelling, a "Back-Alkaline" formulation technique can be utilized to achieve higher pH compositions. These stable aqueous surfactant containing compositions can generally maintain a smooth, acceptable rheology, without significant increases or decreases in viscosity, turbidity or pH, with no separation, settling, or creaming out. In one embodiment of the invention, the surfactant is selected from at least one amphoteric or zwitterionic surfactant. Optionally, the copolymer/surfactant composition can contain other surfactants selected from anionic, nonionic, and cationic surfactants, or combinations thereof.

The instant copolymers of the present invention can be used as a thickener, film former, or as a dye or pigment suspending agent for promoting deposition of colorants on hair and skin. Colorants for hair can be temporary, semipermanent or permanent hair dyes or color restorers that pigment the hair gradually. Temporary and semipermanent hair dyes typically are rinses, gels, sprays, shampoos, sticks, and the like, and hair color restorers are typically in the form of hair dressings or emulsions. Permanent hair dyes, and longer-lasting semipermanent hair dyes, are generally two-part products, one part containing the oxidative dye intermediates and dye couplers, and the other part containing stabilized oxidizing agent, usually hydrogen peroxide at about pH 3-4, and are mixed together immediately before use. It is known that such two-part hair dyeing products are formulated with combinations of surfactant ingredients, usually nonionic surfactants or anionic surfactants, to thicken when the dye mixture is prepared. In addition to the foregoing literature, a general discussion of hair dyeing chemistry and compositions is in Brown et al, SCC Monograph, "Permanent Hair Dyes", Society of Cosmetic Chemists (1996), incorporated herein by reference. The copolymers of the present invention may be incorporated in one or both of the two-parts of such hair dyeing systems, either as the thickener for the acidic stabilized oxidizing portion or in the non-oxidizing portion to be thickened upon mixing with the acidic portion.

In addition to ingredients discussed above, other ingredients commonly used for antiacne products, facial and body hair bleaches, and antiseptic products include oxidizing agents, such as hydrogen peroxide, benzoyl peroxide, and water-soluble inorganic persulfate compounds such as ammonium persulfate, potassium persulfate, and sodium persulfate.

The copolymers of the present invention are particularly useful as emulsification aids for water-insoluble (hydrophobic) oily materials such as natural and synthetic oils, fats, and waxes, including, for example, vegetable oils, animal oils and fats, paraffin oils and waxes, silicone oils and waxes; and the like. Many oily materials are used as solvents, carriers, emollients, or conditioning agents, for example, in hair and skin care products.

The copolymers of the present invention are surprisingly useful stabilizers of silicone fluids, which are commonly used in shampoo products, such as the so-called "two-in-one" combination cleansing/conditioning shampoos. Silicone fluids are generally described as alkylsiloxane polymers. The most common class of silicone polymers are the linear polydimethyl siloxanes having the general formula CH3-(Si(CH3)2-O)w-Si(CH3)3 where w denotes an integer greater than 2. Silicones can also be branched materials wherein one or more alkyl groups in a polymer are replaced with an oxygen atom to create a branch point. Silicone fluids are typically water-insoluble oils having a viscosity in the range of a few mPa to several hundred thousand mPa.

A particularly useful class of silicones for use in hair care products are the so-called rigid silicones (also known as silicone gums), as described, for example in U.S. Pat. No. 4,902,499, incorporated herein by reference, which generally have a viscosity (at about 20 C) of greater than about 600,000 mPa and have a weight average molecular weight of at least about 500,000 Daltons as determined by intrinsic viscosity measurement. The copolymers of the present invention are surprisingly effective for stabilizing two-in-one type shampoo formulations containing rigid silicone conditioning agents.

Another class of silicone materials that are particularly useful in combination with the copolymers of the present invention are the volatile silicones, which are often used as lubricants in hair care products, such as shampoos. Volatile silicones include cyclic and linear polydimethylsiloxanes, and the like. Cyclic volatile silicones typically contain about 3 to about 7 silicon atoms, alternating with oxygen atoms, in a cyclic ring structure. Each silicon atom is also substituted with two alkyl groups, typically methyl groups. Linear volatile silicones are silicone fluids, as described above, having viscosities of not more than about 25 mPa. A description of volatile silicones is found in Todd and Byers, "Volatile Silicone Fluids for Cosmetics", Cosmetics and Toiletries, Vol. 91(1), pp. 27-32 (1976), and in Kasprzak, "Volatile Silicones", Soap/Cosmetics/Chemical Specialities, pp. 40-43 (December 1986), each incorporated herein by reference.

Other silicone oils include the dimethicone copolyols, which are linear or branched copolymers of dimethylsiloxane (dimethicone) and alkylene oxides. The dimethicone polyols can be random or block copolymers. A generally useful class of dimethicone polyols are block copolymers having blocks of polydimethylsiloxane and blocks of polyalkylene oxide, such as blocks of polyethylene oxide, polypropylene oxide, or both. Silicone fluids, including volatile silicones, silicone gums, and silicone copolymers, are available from a variety of commercial sources such as Dow Corning, General Electric Company, and Noveon, Inc.

Other oily materials that are useful in combination with the copolymers of the present invention include, for example, acetylated lanolin alcohols; lanolin alcohol concentrates; esters of lanolin fatty acids such as the isopropyl esters of lanolin fatty acid; polyol fatty acids; ethoxylated alcohols, such as ethoxylate and castor oils; sterols; sterol esters; sterol ethoxylates; and like materials. Many of such esters and ethoxylates are also useful as non-ionic surfactants.

Numerous ingredients are known in the art as conditioning agents for hair or skin, and humectants, and in addition to those previously discussed, non-limiting examples include PCA (DL-pyrrolidone carboxylic acid) and its salts, such as lysine PCA, aluminum PCA, copper PCA, chitosan PCA, and the like, allantoin; urea; hyaluronic acid and its salts; ceramides; sorbic acid and its salts; sugars and starches and derivatives thereof; lactamide MEA; and the like.

The copolymeric rheology modifiers of the present invention do not start to build substantial viscosity until an acidic pH of about 6.8 to about 3.0 is achieved. The pH of cosmetic formulations is typically in, but not limited to, a range of about 3.0 to about 8.0.

Surprisingly, it has been found that when the formulations containing the instant copolymers of the invention in combination with an amphoteric surfactant are lowered to an acidic pH (to build a desired increase in viscosity) and then subsequently raised in pH, the viscosity, turbidity and yield value generally remain unchanged or often actually improve. This formulating technique is herein referred to as "back-alkaline" thickening. The back-alkaline formulating technique broadens the scope of application for the instant copolymers of the invention, allowing for the increase of the pH of a formulation subsequent to the acid treatment or polymer thickening step. Additionally, the process of back-alkaline thickening can be used to further increase the viscosity and stability of compositions formulated in the generally accepted pH range.

In one embodiment of the invention, the one or more copolymers, copolymers, and the like are added to water and mixed. An amphoteric surfactant is subsequently added to the aqueous polymeric solution and mixed therein. If desired, optional surfactants selected from anionic, non-ionic, and cationic surfactants, or combinations thereof can be added to the formulation. Suitable amphoteric, anionic, cationic and nonionic surfactants are described herein. An acidic pH adjusting agent is then added and mixed to decrease the pH of the composition to obtain the desired low pH formulation. In one aspect, the pH of the composition can be initially adjusted with an acid between a pH of about 0.5 to about 7.0, in another aspect between about 3.0 to about 6.0, and in still a further aspect from about 4.0 to about 5.0. The acidic pH adjusting agent can be selected from the organic and mineral acids described herein. In another embodiment, any acidic ingredient that is capable of reducing the initial pH of the instant copolymer composition and effecting a viscosity increase of the copolymer composition is contemplated within the scope of the invention. The acidic active ingredients can be employed with or without a pH adjusting agent. Examples of suitable acidic ingredients are selected from but not limited to the dermatological and cosmeceutical acidic active ingredients described herein.

Surprisingly, it has been discovered that when citric acid is employed in the instant copolymer neutralization step (i.e., pH lowering), the viscosity of the composition actually increases when the alkaline pH adjusting agent is subsequently added to the formulation. The pH of the acid thickened composition should desirably be at least about 1 and preferably 2 units and preferably at least 3 pH units below the final target pH of the composition. An alkaline pH adjusting agent is then added to increase the pH of the composition to the final target pH. Alkaline pH adjusting agents suitable for the Back-Alkaline formulation technique are described herein.

The desired pH of the compositions of the present invention is obviously dependent on the specific end product applications. Generally, personal care compositions have a pH range from about 3 to about 8. Generally, home care compositions have a pH range from about 1 to about 12.

The term "effective amount" means for example the amount necessary to achieve the desired effect.

Another embodiment of the instant invention is an aqueous personal care, household care, or fabric care composition comprising an effective amount of at least one copolymer of formulae (I) and/or (II)

wherein

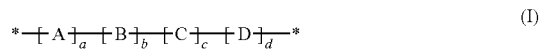

(I)

wherein a, b, c, and d represent the percentage by weight that each repeating unit or derived monomer is contained within the copolymer;

a, b, c, and d add up to total substantially 100 weight percent relative to the total weight of the copolymer;

a is from about 81 to about 99.8% by weight of the copolymer;

b is from about 0.1% to about 18.9% by weight of the copolymer;

c is from about 0.1% to about 18.9% by weight of the copolymer;

d is from about 0% to about 18.8% by weight of the copolymer;

* is a terminal group, for example, a catalyst residue;

A is an amino-substituted vinyl monomer or salt thereof selected from the group consisting of mono-(C1-C4)alkylamino(C1-C8)alkyl(meth)acrylate, di-(C1-C4)alkylamino(C1-C8)alkyl(meth)acrylate, mono-(C1-C4)alkylamino(C1-C8)alkyl-(meth)acrylamide, di-(C1-C4)alkylamino(C1-C8)alkyl(meth)acrylamide, nitrogen-containing heterocyclic (meth)acrylamide, nitrogen-containing heterocyclic (meth)acrylate, and mixtures thereof;

B is a hydrophobic nonionic vinyl monomer selected from the group consisting of $C_1$-$C_{30}$ alkyl ester of acrylic acid, $C_1$-$C_{30}$ alkyl ester of methacrylic acid, and mixtures thereof;

C is an associative-like monomer of formula (V)

(V)

wherein, each R2 is independently H, methyl, —C(O)OH, or —C(O)OR3; R3 is C1-C30 alkyl; T is —$CH_2$C(O)O—, —C(O)O—, —O—, —$CH_2$O—, —NHC(O)NH—, —C(O)NH—, —Ar—($CE_2$)z-NHC(O)O—, —Ar—($CE_2$)z-NHC(—O)NH—, or —$CH_2CH_2$NHC(O)—; Ar is a divalent aryl;

E is H or methyl; z is 0 or 1; k is an integer in the range of 0 to about 30, and m is 0 or 1, with the proviso that when k is 0, m is 0, and when k is in the range of 1 to about 30, m is 1; (R4-O)n is a polyoxyalkylene, which is a homopolymer, a random copolymer, or a block copolymer of $C_2$-$C_4$ oxyalkylene units, wherein R4 is $C_2H_4$, $C_3H_6$, $C_4H_8$, or a mixture thereof, and n is an integer in the range of about 5 to about 250, preferably about 5 to about 100, more preferably about 10 to about 80, and most preferably about 15 to about 60; Y is —R4O—, —R4NH—, —C(O)—, —C(O)NH—, —R4NHC(O)NH—, or —C(O)NHC(O)—; and R5 is a substituted or unsubstituted alkyl selected from the group consisting of a $C_8$-$C_{40}$ linear alkyl, a $C_8$-$C_{40}$ branched alkyl, a $C_8$-$C_{40}$ carbocyclic alkyl, a $C_2$-$C_{40}$ alkyl-substituted phenyl, an aryl-substituted $C_2$-$C_{40}$ alkyl, and a $C_8$-$C_{80}$ complex ester; wherein the R5 alkyl group optionally comprises one or more substituents selected from the group consisting of a hydroxyl group, an alkoxyl group, and a halogen group; and D is an associative-like vinyl monomer selected from the group consisting of cetyl polyethoxylated methacrylate (CEM), cetearyl polyethoxylated methacrylate (CSEM), stearyl polyethoxylated (meth)acrylate, arachidyl polyethoxylated (meth)acrylate, behenyl polyethoxylated methacrylate (BEM), lauryl polyethoxylated methacrylate (LEM), cerotyl polyethoxylated (meth)acrylate, monthanyl polyethoxylated (meth)acrylate, melissyl polyethoxylated (meth)acrylate, lacceryl polyethoxylated (meth) acrylate, tristyryl phenolpolyethoxylated methacrylate (TEM), hydrogenated castor oil polyethoxylated methacrylate (HCOEM), canola polyethoxylated (meth)acrylate, and cholesterol polyethoxylated methacrylate (CHEM), with the proviso that when both C and D are present in the copolymer, C and D are not the same;

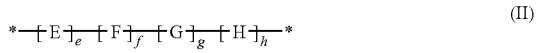

(II)

wherein e, f, g, and h represent the percentage by weight that each repeating unit or derived monomer is contained within the copolymer;

e, f, g, and h add up to total substantially 100 weight percent relative to the total weight of the copolymer;

e is from about 5% to about 99.6% by weight of the copolymer;

f is from about 5% to about 99.6% by weight of the copolymer;

g is from about 0.1% to about 40% by weight of the copolymer;

h is from about 0.1% to about 40% by weight of the copolymer;

* is a terminal group, for example, a catalyst residue;

E is an amino-substituted vinyl monomer or salt thereof selected from the group consisting of mono-(C1-C4)alkylamino(C1-C8)alkyl(meth)acrylate, di-(C1-C4)alkylamino(C1-C8)alkyl(meth)acrylate, mono-(C1-C4)alkylamino(C1-C8)alkyl-(meth)acrylamide, di-(C1-C4)alkylamino(C1-C8)alkyl(meth)acrylamide, nitrogen-containing heterocyclic (meth)acrylamide, nitrogen-containing heterocyclic (meth) acrylate, and mixtures thereof;

F is a hydrophobic nonionic vinyl monomer selected from the group consisting of $C_1$-$C_{30}$ alkyl ester of acrylic acid, $C_1$-$C_{30}$ alkyl ester of methacrylic acid, and mixtures thereof;

G is an associative-like monomer of formula (V)

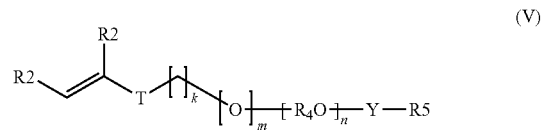

wherein, each R2 is independently H, methyl, —C(O)OH, or —C(O)OR3; R3 is C1-C30 alkyl; T is —CH$_2$C(O)O—, —C(O)O—, —O—, —CH$_2$O—, —NHC(O)NH—, —C(O)NH—, —Ar—(CE$_2$)z-NHC(O)O—, —Ar—(CE$_2$)z-NHC(—O)NH—, or —CH$_2$CH$_2$NHC(O)—; Ar is a divalent aryl; E is H or methyl; z is 0 or 1; k is an integer in the range of 0 to about 30, and m is 0 or 1, with the proviso that when k is 0, m is 0, and when k is in the range of 1 to about 30, m is 1; (R4-O)n is a polyoxyalkylene, which is a homopolymer, a random copolymer, or a block copolymer of $C_2$-$C_4$ oxyalkylene units, wherein R4 is $C_2H_4$, $C_3H_6$, $C_4H_8$, or a mixture thereof, and n is an integer in the range of about 5 to about 250, preferably about 5 to about 100, more preferably about 10 to about 80, and most preferably about 15 to about 60; Y is —R4O—, —R4NH—, —C(O)—, —C(O)NH—, —R4NHC(O)NH—, or C(O)NHC(O)—; and R5 is a substituted or unsubstituted alkyl selected from the group consisting of a $C_8$-$C_{40}$ linear alkyl, a $C_8$-$C_{40}$ branched alkyl, a $C_8$-$C_{40}$ carbocyclic alkyl, a $C_2$-$C_{40}$ alkyl-substituted phenyl, an aryl-substituted $C_2$-$C_{40}$ alkyl, and a $C_8$-$C_{80}$ complex ester; wherein the R5 alkyl group optionally comprises one or more substituents selected from the group consisting of a hydroxyl group, an alkoxyl group, and a halogen group; and H is an associative-like vinyl monomer selected from the group consisting of cetyl polyethoxylated methacrylate (CEM), cetearyl polyethoxylated methacrylate (CSEM), stearyl polyethoxylated (meth)acrylate, arachidyl polyethoxylated (meth)acrylate, behenyl polyethoxylated methacrylate (BEM), lauryl polyethoxylated methacrylate (LEM), cerotyl polyethoxylated (meth)acrylate, monthanyl polyethoxylated (meth)acrylate, melissyl polyethoxylated (meth)acrylate, lacceryl polyethoxylated (meth) acrylate, tristyryl phenolpolyethoxylated methacrylate (TEM), hydrogenated castor oil polyethoxylated methacrylate (HCOEM), canola polyethoxylated (meth)acrylate, and cholesterol polyethoxylated methacrylate (CHEM), with the proviso that G and H are not the same.

The present personal care, household care, and/or fabric care compositions may further comprise dyes, pigments or mixtures thereof.

Accordingly, the present invention further pertains to a personal care, household care, and/or fabric care composition comprising an effective amount of at least one copolymer of formulae (I) and/or (II)

a cosmetically acceptable adjuvant, and a dye or a pigment or mixtures thereof.

Dyes of component according to the present invention are for example:

disperse dyes which may be solubilized in solvents like direct hair dyes of the HC type, for example HC Red No. 3, HC Blue No. 2 and all other hair dyes listed in International Cosmetic Ingredient Dictionary and Handbook, 7$^{th}$ edition 1997) or the dispersion dyes listed in Color Index International or Society of Dyers and Colourists;

color varnishes (insoluble salts of soluble dyes, like many Ca-, Ba- or Al-salts of anionic dyes);

soluble anionic or cationic dyes, like acid dyes (anionic), basic dyes (cationic), direct dyes, reactive dyes or solvent dyes.

Generally, for the coloration of the instant compositions, all substances are suitable which have an absorption in the visible light of electromagnetic radiation (wavelength of ca. 4000 to 700 nm). The absorption is often caused by the following chromophores: Azo- (mono-, di, tris-, or poly-) stilbene-, carotenoide-, diarylmethan-, triarylmethan-, xanthen-, acridin-, quinoline, methin- (also polymethin-), thiazol-, indamin-, indophenol-, azin-, oxazin, thiazin-, anthraquinone-, indigoid-, phtalocyanine- and further synthetic, natural and/or inorganic chromophores.

According to the instant invention, pigments include inorganic pigments, metal oxides and hydroxides, mica, organic pigments, pearlescent pigments, mineral silicates, porous materials, carbons, interference pigments, and the like.

Examples of the inorganic pigments capable of being utilized according to the present invention are ultramarine blue, ultramarine violet, Prussian blue, manganese violet, titanium-coated mica, bismuth oxychloride, iron oxides, iron hydroxide, titanium dioxide, titanium lower oxides, chromium hydroxide and oxides, and carbon based pigments (e.g. Carbon Black). Of these inorganic pigments, ultramarine blue and Prussian blue are particular advantageous.

According to the instant invention, the range of useful organic pigments is slected from the group consisting of monoazo, disazo, naphthol, dioxazone, azomethin, azocondensation, metal complex, nitro, perinone, quinoline, anthraquinone, benzimidozolone, isoindoline, isoindolinone, triarylmethane, quinacridone, hydroxyanthraquinone, aminoanthraquinone, anthrapyrimidine, indanthrone, flavanthrone, pyranthrone, anthantrone, isoviolanthrone, diketopyrrolopyrrole, carbazole, indigo or thiolndigo pigments.

According to the instant invention, examples of the organic pigments are C.I. 15850, C.I. 15850:1, C.I. 15585:1, C.I. 15630, C.I. 15880:1, C.I. 73360, C.I. 12085, C.I. 15865:2, C.I. 12075, C.I. 21110, C.I. 21095, and C.I. 11680, C.I. 74160 and zirconium, barium, or aluminum lakes of C.I. 45430, C.I. 45410, C.I. 45100, C.I. 17200, C.I. 45380, C.I. 45190, C.I. 14700, C.I. 15510, C.I. 19140, C.I. 15985, C.I. 45350, C.I. 47005, C.I. 42053, C.I. 42090.

C.I. means Colour Index as compiled by the by The Society of Dyers and Colourists and The American Association of Textile Chemists and Colourists.

According to the instant invention, mixtures of the organic pigments may be used. According to the instant invention, mixtures of the inorganic and organic pigments may be used.

According to the instant invention, mixtures of dyes and organic and/or inorganic pigments may be used.

The dyes and/or pigments of the personal care, household care, and/or fabric care compositions preferably comprise no more than about 10 weight percent of the composition; more preferably no more than about 7 weight percent of the personal care, household care, and/or fabric care composition; even more preferably no more than about 5 weight percent; and still more preferably no more than about 3 weight percent. The dyes and/or pigments of the personal care, household care, and/or fabric care composition preferably comprise at least about 0.0001 weight percent of the personal care, household care, and/or fabric care composition, more preferably at least about 0.01 weight percent, even more preferably at least about 0.1 weight percent, and still more preferably at least about 0.2 by weight of the composition.

Another embodiment of the instant invention is an aqueous personal care, household care, or fabric care composition comprising an effective amount of at least one copolymer of formulae (I) and/or (II) wherein the pH is from about 0.5 to about 7. Another embodiment of the instant invention is an aqueous personal care, household care, or fabric care composition comprising an effective amount of at least one copolymer of formulae (I) and/or (II) wherein the pH is from about 1 to about 6.5.

Another embodiment of the instant invention is an aqueous personal care, household care, or fabric care composition comprising an effective amount of at least one copolymer of formulae (I) and/or (II) wherein the pH is from about 1 to about 6. Another embodiment of the instant invention is an aqueous personal care, household care, or fabric care composition comprising an effective amount of at least one copolymer of formulae (I) and/or (II) wherein the pH is 0.5, 1.0, 1.5, 2.0, 2.5, 3.0, 3.5, 4.0, 4.5, 5.0, 5.5, 6.0, 6.5, 7.0 and all values in between 0.5 and 7.0.

Another embodiment of the instant invention is a method for the rheological modification of an aqueous personal care, household care, or fabric care composition wherein said method comprises adding to said personal care, household care, or fabric care composition an effective amount of a copolymer of formula (I)

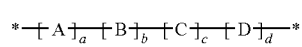

wherein a, b, c, and d represent the percentage by weight that each repeating unit or derived monomer is contained within the copolymer;

a, b, c, and d add up to total substantially 100 weight percent relative to the total weight of the copolymer;

a is from about 81 to about 99.8% by weight of the copolymer;

b is from about 0.1% to about 18.9% by weight of the copolymer;

c is from about 0.1% to about 18.9% by weight of the copolymer;

d is from about 0% to about 18.8% by weight of the copolymer;

* is a terminal group, for example, a catalyst residue;

A is an amino-substituted vinyl monomer or salt thereof selected from the group consisting of mono-(C1-C4)alkylamino(C1-C8)alkyl(meth)acrylate, di-(C1-C4)alkylamino (C1-C8)alkyl(meth)acrylate, mono-(C1-C4)alkylamino(C1-C8)alkyl-(meth)acrylamide, di-(C1-C4)alkylamino(C1-C8) alkyl(meth)acrylamide, nitrogen-containing heterocyclic (meth)acrylamide, nitrogen-containing heterocyclic (meth)acrylate, and mixtures thereof;

B is a hydrophobic nonionic vinyl monomer selected from the group consisting of $C_1$-$C_{30}$ alkyl ester of acrylic acid, $C_1$-$C_{30}$ alkyl ester of methacrylic acid, and mixtures thereof;

C is an associative-like monomer of formula (V)

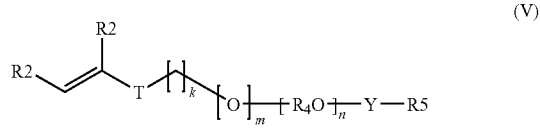

wherein, each R2 is independently H, methyl, —C(O)OH, or —C(O)OR3; R3 is C1-C30 alkyl; T is —CH$_2$C(O)O—, —C(O)O—, —O—, —CH$_2$O—, —NHC(O)NH—, —C(O)NH—, —Ar—(CE$_2$)z-NHC(O)O—, —Ar—(CE$_2$)z-NHC(—O)NH—, or —CH$_2$CH$_2$NHC(O)—; Ar is a divalent aryl; E is H or methyl; z is 0 or 1; k is an integer in the range of 0 to about 30, and m is 0 or 1, with the proviso that when k is 0, m is 0, and when k is in the range of 1 to about 30, m is 1; (R4-O)n is a polyoxyalkylene, which is a homopolymer, a random copolymer, or a block copolymer of C$_2$-C$_4$ oxyalkylene units, wherein R4 is C$_2$H$_4$, C$_3$H$_6$, C$_4$H$_8$, or a mixture thereof, and n is an integer in the range of about 5 to about 250, preferably about 5 to about 100, more preferably about 10 to about 80, and most preferably about 15 to about 60; Y is —R4O—, —R4NH—, —C(O)—, —C(O)NH—, —R4NHC(O)NH—, or —C(O)NHC(O)—; and R5 is a substituted or unsubstituted alkyl selected from the group consisting of a C$_8$-C$_{40}$ linear alkyl, a C$_8$-C$_{40}$ branched alkyl, a C$_8$-C$_{40}$ carbocyclic alkyl, a C$_2$-C$_{40}$ alkyl-substituted phenyl, an aryl-substituted C$_2$-C$_{40}$ alkyl, and a C$_8$-C$_{80}$ complex ester; wherein the R5 alkyl group optionally comprises one or more substituents selected from the group consisting of a hydroxyl group, an alkoxyl group, and a halogen group; and D is an associative-like vinyl monomer selected from the group consisting of cetyl polyethoxylated methacrylate (CEM), cetearyl polyethoxylated methacrylate (CSEM), stearyl polyethoxylated (meth)acrylate, arachidyl polyethoxylated (meth)acrylate, behenyl polyethoxylated methacrylate (BEM), lauryl polyethoxylated methacrylate (LEM), cerotyl polyethoxylated (meth)acrylate, monthanyl polyethoxylated (meth)acrylate, melissyl polyethoxylated (meth)acrylate, lacceryl polyethoxylated (meth) acrylate, tristyryl phenolpolyethoxylated methacrylate (TEM), hydrogenated castor oil polyethoxylated methacrylate (HCOEM), canola polyethoxylated (meth)acrylate, and cholesterol polyethoxylated methacrylate (CHEM), with the proviso that when both C and D are present in the copolymer, C and D are not the same.

Another embodiment of the instant invention is a method for the rheological modification of an aqueous personal care, household care, or fabric care composition wherein said method comprises adding to said personal care, household care, or fabric care composition an effective amount of a copolymer of formula (II)

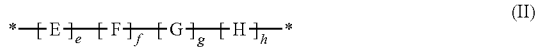
(II)

wherein e, f, g, and h represent the percentage by weight that each repeating unit or derived monomer is contained within the copolymer;

e, f, g, and h add up to total substantially 100 weight percent relative to the total weight of the copolymer;

e is from about 5% to about 99.6% by weight of the copolymer;

f is from about 5% to about 99.6% by weight of the copolymer;

g is from about 0.1% to about 40% by weight of the copolymer;

h is from about 0.1% to about 40% by weight of the copolymer;

* is a terminal group, for example, a catalyst residue;

E is an amino-substituted vinyl monomer or salt thereof selected from the group consisting of mono-(C1-C4)alkylamino(C1-C8)alkyl(meth)acrylate, di-(C1-C4)alkylamino(C1-C8)alkyl(meth)acrylate, mono-(C1-C4)alkylamino(C1-C8)alkyl-(meth)acrylamide, di-(C1-C4)alkylamino(C1-C8)alkyl(meth)acrylamide, nitrogen-containing heterocyclic (meth)acrylamide, nitrogen-containing heterocyclic (meth)acrylate, and mixtures thereof;

F is a hydrophobic nonionic vinyl monomer selected from the group consisting of C1-C30 alkyl ester of acrylic acid, C1-C30 alkyl ester of methacrylic acid, and mixtures thereof;

G is an associative-like monomer of formula (V)

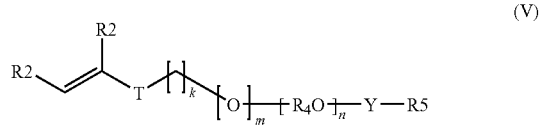
(V)

wherein, each R2 is independently H, methyl, —C(O)OH, or —C(O)OR3; R3 is C1-C30 alkyl; T is —CH$_2$C(O)O—, —C(O)O—, —O—, —CH$_2$O—, —NHC(O)NH—, —C(O)NH—, —Ar—(CE$_2$)z-NHC(O)O—, —Ar—(CE$_2$)z-NHC(—O)NH—, or —CH$_2$CH$_2$NHC(O)—; Ar is a divalent aryl; E is H or methyl; z is 0 or 1; k is an integer in the range of 0 to about 30, and m is 0 or 1, with the proviso that when k is 0, m is 0, and when k is in the range of 1 to about 30, m is 1; (R4-O)n is a polyoxyalkylene, which is a homopolymer, a random copolymer, or a block copolymer of C$_2$-C$_4$ oxyalkylene units, wherein R4 is C$_2$H$_4$, C$_3$H$_6$, C$_4$H$_8$, or a mixture thereof, and n is an integer in the range of about 5 to about 250, preferably about 5 to about 100, more preferably about 10 to about 80, and most preferably about 15 to about 60; Y is —R4O—, —R4NH—, —C(O)—, —C(O)NH—, —R4NHC(O)NH—, or —C(O)NHC(O)—; and R5 is a substituted or unsubstituted alkyl selected from the group consisting of a C$_8$-C$_{40}$ linear alkyl, a C$_8$-C$_{40}$ branched alkyl, a C$_8$-C$_{40}$ carbocyclic alkyl, a C$_2$-C$_{40}$ alkyl-substituted phenyl, an aryl-substituted C$_2$-C$_{40}$ alkyl, and a C$_8$-C$_{80}$ complex ester; wherein the R5 alkyl group optionally comprises one or more substituents selected from the group consisting of a hydroxyl group, an alkoxyl group, and a halogen group; and H is an associative-like vinyl monomer selected from the group consisting of cetyl polyethoxylated methacrylate (CEM), cetearyl polyethoxylated methacrylate (CSEM), stearyl polyethoxylated (meth)acrylate, arachidyl polyethoxylated (meth)acrylate, behenyl polyethoxylated methacrylate (BEM), lauryl polyethoxylated methacrylate (LEM), cerotyl polyethoxylated (meth)acrylate, monthanyl polyethoxylated (meth)acrylate, melissyl polyethoxylated (meth)acrylate, lacceryl polyethoxylated (meth) acrylate, tristyryl phenolpolyethoxylated methacrylate (TEM), hydrogenated castor oil polyethoxylated methacrylate (HCOEM), canola polyethoxylated (meth)acrylate, and cholesterol polyethoxylated methacrylate (CHEM), with the proviso that G and H are not the same.

The following examples describe certain embodiments of this invention, but the invention is not limited thereto. It should be understood that numerous changes to the disclosed embodiments could be made in accordance with the disclosure herein without departing from the spirit or scope of the invention. These examples are therefore not meant to limit the scope of the invention. Rather, the scope of the invention is to be determined only by the appended claims and their equivalents. In these examples all parts given are by weight unless otherwise indicated.

The following examples illustrate the invention.

EXAMPLE 1

Random Emulsion Copolymer

The following copolymer emulsion is synthesized according to the following procedure and ratios:

Monomer Emulsion

| Tertiary butyl amino ethyl methacrylate (TBAEMA, Ciba) | 200.64 g |
|---|---|
| Ethyl Acrylate (EA, Rohm & Haas) | 44.30 g |
| Butane diol diacrylate (BDDA, 10% assay, BASF) | 6.70 g |

Aqueous Emulsion

| Water (deionized) | 107.00 g |
|---|---|
| Iso tri-decyl ethoxylate (GENOPOL X407, 15% assay, Clariant 40 moles of ethoxylate [40EO]) | 160.52 g |
| *Beheneth C22 methacrylate (BEM, SIPOMER BEM, Rhodia 25 moles of ethoxylate [25EO] | 13.40 g |
| *Ceteareth C16-C18 methacrylate (PLEX, Cognis 22 moles of ethoxylate [22EO]) | 11.16 g |

*Methacrylic acid makes up about 30 wt. % of the associative monomer.

Vessel

| Iso tri-decyl ethoxylate (GENOPOL X407, 15% assay, Clariant 40 moles of ethoxylate [40 moles EO]) | 17.86 g |
|---|---|
| Flush water (GENOPOL X407 feed) | 10.00 g |
| Boiled deionized water | 318.29 g |
| 2,2'-azo bis (2-methylpropionamidine) dihydrochloride (V50, 2% assay, Chemiehandel) | 17.06 g |

Initiator Feed

| 2% V50 solution | 36.41 g |
|---|---|
| Flush water (deionized, V50 solution) | 8.00 g |

Post Addition

| Flush water (deionized, pre-emulsion) | 48.06 g |
|---|---|
| Preservative (Thor) | 0.60 g |

Lab Procedure
1. Boil vessel water for 5 minutes. Cool vessel water temperature to 80 C whilst blowing nitrogen (on full) into the headspace of the reaction flask. When at 80 C reduce nitrogen flow to a bleed.
2. Pre emulsified monomer in aqueous phase for 5 minutes using high speed homogeniser.
3. Add vessel X407 and flush followed by V50 solution and leave for 2 minutes before commencing pre-emulsion and initiator feeds at a rate to go in over 60 and 90 minutes, respectively. Flush lines out with water indicated after each feed is completed.
4. After the initiator feed is finished, hold for a further 1 hour at 80 C.
5. Cool, adding preservative at 40 C.

Molecular weight estimate of the instant copolymer is 50,000 Daltons.

The resulting particle size as supplied polymer is 129.7 nm measured on a Malvern Zetasizer Photon correlation spectrometer. The as supplied viscosity is 245cPs measured on a Brookfield RVT spindle 2 speed 20 rpm. The clarity of this polymer is measured in solution using a 0.5% active polymer in deionized water and the pH is adjusted to 4 using 1% acetic acid. The prepared solution is measured on a Hanna Instruments LP2000 turbidity meter and the measurements are made in NTUs (nepholic turbidity units). The clarity measurements for the instant copolymer is 18.74 NTUs.

EXAMPLE 2

Random Emulsion Copolymer

The synthetic procedure of Instant Example 1 is followed to synthesize a random emulsion copolymer with the following proportions by weight of monomer: TBAEMA=75 wt %; EA=22 wt %; BEM=2.25 wt %; Plex=0.75 wt %; BDDA=2500 ppm. The ratio of BEM to Plex is 3:1 by weight.

After synthesis and cooling the aqueous solution of the instant copolymer, solution solids of 29.1% is measured.

Molecular weight estimate of the instant copolymer is 50,000 Daltons.

The resulting particle size as supplied polymer is 114.9 nm measured on a Malvern Zetasizer Photon correlation spectrometer. The as supplied viscosity is 370cPs measured on a Brookfield RVT spindle 2 speed 20 rpm. The clarity of the instant copolymer is measured in solution using a 0.5% active polymer in deionized water and the pH is adjusted to 4 using 1% acetic acid. The prepared solution is measured on a Hanna Instruments LP2000 turbidity meter and the measurements are made in NTUs (nepholic turbidity units). The clarity measurements for the instant copolymer is 13.06 NTUs.

EXAMPLE 3

Random Emulsion Copolymer

The synthetic procedure of Instant Example 1 is followed to synthesize a random emulsion copolymer with the following proportions by weight of monomer: TBAEMA=75 wt %; EA=22 wt %; BEM=1.5 wt %; Plex=1.5 wt %; with x-linker BDDA added in addition on the weight of monomer solids at 2500 ppm. The ratio of BEM to Plex is 1:1 by weight.

After synthesis and cooling the aqueous solution of the instant copolymer, solution solids of 29.2% is measured.

Molecular weight estimate for the instant copolymer is 50,000 Daltons.

The resulting particle size as supplied polymer is 122.3 nm measured on a Malvern Zetasizer Photon correlation spectrometer. The as supplied viscosity is 355cPs measured on a Brookfield RVT spindle 2 speed 20 rpm. The clarity of this copolymer is measured in solution using a 0.5% active polymer in deionized water and the pH is adjusted to 4 using 1% acetic acid. The prepared solution is measured on a Hanna Instruments LP2000 turbidity meter and the measurements are made in NTUs (nepholic turbidity units). The clarity measurements for the instant copolymer is 13.24 NTUs.

EXAMPLE 4

Random Emulsion Copolymer

The synthetic procedure of Instant Example 1 is followed to synthesize a random emulsion copolymer with the following proportions by weight of monomer: TBAEMA=75 wt %; EA=22 wt %; BEM=0.75 wt %; Plex=2.25 wt %; with x-linker BDDA added in addition on the weight of monomer solids at 2500 ppm. The ratio of BEM to Plex is 1:3 by weight.

After synthesis and cooling the aqueous solution of the instant co-polymer, solution solids of 29.1% is measured.

Molecular weight estimate for the instant copolymer is 50,000 Daltons.

The resulting particle size as supplied polymer is 116.8 nm measured on a Malvern Zetasizer Photon correlation spectrometer. The as supplied viscosity is 555cPs measured on a Brookfield RVT spindle 2 speed 20 rpm. The clarity of the instant copolymer is measured in solution using a 0.5% active polymer in deionized water and the pH is adjusted to 4 using 1% acetic acid. The prepared solution is measured on a Hanna Instruments LP2000 turbidity meter and the measurements are made in NTUs (nepholic turbidity units). The clarity measurements for the instant copolymer is 13.46 NTUs.

Comparative Example 1

Random Emulsion Copolymer

The synthetic procedure of Instant Example 1 is followed to synthesize a random emulsion copolymer with the following proportions by weight of monomer: TBAEMA=75 wt %; EA=22 wt %; BEM=3 wt %; Plex=0 wt %; with x-linker BDDA added in addition on the weight of monomer solids at 2500 ppm.

After synthesis and cooling the aqueous solution of the instant co-polymer, solution solids of 29.0% is measured.

Molecular weight estimate for this copolymer is 50,000 Daltons.

The resulting particle size as supplied polymer is 129.7 nm measured on a Malvern Zetasizer Photon correlation spectrometer. The as supplied viscosity is 245cPs measured on a Brookfield RVT spindle 2 speed 20 rpm. The clarity of this copolymer is measured in solution using a 0.5% active polymer in deionized water and the pH is adjusted to 4 using 1% acetic acid. The prepared solution is measured on a Hanna Instruments LP2000 turbidity meter and the measurements are made in NTUs (nepholic turbidity units). The clarity measurement for this polymer is 18.74 NTUs.

EXAMPLE 5

Thickening Efficiency in Simple Acid Solutions

Two percent active dilutions of all prepared polymers are tested in 1% aqueous acetic acid at a pH=4 to evaluate the thickening efficiency. The viscosity measurements are made using a Brookfield RVT, spindle 2 (speed 20 rpm).

| 2% Active Polymer in 1% Acetic Acid | | |
|---|---|---|
| Example | Day 0 viscosity (cPs) | Day 1 viscosity (cPs) |
| 2 | 24000 | 29150 |
| 3 | 15000 | 16050 |
| 4 | 10350 | 13950 |

EXAMPLE 6

Synergy in Surfactant and Acid Solutions

The instant copolymer samples are evaluated (at various concentrations) in simple surfactant solutions plus acid to measure any increase in thickening efficiency when used in combination with various surfactants. The surfactants chosen are typically used in home care formulations. The concentration is 1.5% active polymer based on weight and 2% active BEROL 175 based on weight. The surfactant studied is BEROL 175=carbon chain length 12-16 Alcohol Ethoxylate 7.5 EO. The pH is adjusted to a pH=3 with 50% HCl. The viscosity measurements are made using a Brookfield RVT, spindle 2 (speed 20 rpm).

| 1.5% Active Polymer in 2% w/w C12-C16 7.5EO - pH 3 with 50% HCL | | |
|---|---|---|
| Example | Day 0 viscosity (cPs) | Day 1 viscosity (cPs) |
| None | 28 | 28 |
| Comparative Example 1 | 200 | 256 |
| Example 2 | 300 | 346 |
| Example 3 | 400 | 370 |
| Example 4 | 506 | 414 |

The instant copolymers show an improved and sustained increase in acidic solution viscosity when compared to a polymer in the prior art.

EXAMPLE 7

Synergy in Surfactant and Acid Solutions

The instant copolymer samples are evaluated (at various concentrations) in simple surfactant solutions plus acid to measure any increase in thickening efficiency when used in combination with various surfactants. The surfactants chosen are typically used in home care formulations. The concentration is 1.5% active polymer based on weight and 2% active BEROL 260 based on weight. The surfactant studied is BEROL 260=carbon chain length 9-11 Alcohol Ethoxylate 4 EO. The pH is adjusted to a pH=3 with 50% HCl. The viscosity measurements are made using a Brookfield RVT, spindle 4 (speed 20 rpm).

| 1.5% Active Polymer in 2% w/w C9-C11 4EO - pH 3 with 50% HCL | | |
|---|---|---|
| Example | Day 0 viscosity (cPs) | Day 1 viscosity (cPs) |
| None | 54 | 54 |
| Comparative | 6340 | 5640 |

-continued

| 1.5% Active Polymer in 2% w/w C9-C11 4EO - pH 3 with 50% HCL | | |
|---|---|---|
| Example | Day 0 viscosity (cPs) | Day 1 viscosity (cPs) |
| Example 1 | | |
| Example 2 | 7650 | 7000 |
| Example 3 | 6490 | 6200 |
| Example 4 | 6810 | 6900 |

The instant copolymers show an improved and sustained increase in acidic solution viscosity when compared to a polymer in the prior art.

EXAMPLE 8

Synergy in Surfactant and Acid Solutions

The instant copolymer samples are evaluated (at various concentrations) in simple surfactant solutions plus acid to measure any increase in thickening efficiency when used in combination with various surfactants. The surfactants chosen are typically used in home care formulations. The concentration is 1.5% active polymer based on weight and 2% active CRODASINIC HT based on weight. The surfactant studied is CRODASINIC HT=Myristyl di-methyl amine oxide & Sodium lauryl sarcosinate. The pH is adjusted to a pH=3 with 50% HCl. The viscosity measurements are made using a Brookfield RVT, spindle 6 (speed 20 rpm).

| 1.5% Active Polymer in 2% w/w CRODASINIC HT - pH 3 with 50% HCL | | |
|---|---|---|
| Example | Day 0 viscosity (cPs) | Day 1 viscosity (cPs) |
| None | 72 | 72 |
| Comparative Example 1 | 20400 | 19000 |
| Example 2 | 27000 | 27600 |
| Example 3 | 17500 | 21050 |
| Example 4 | 28400 | 29650 |

The instant copolymers show an improved and sustained increase in acidic solution viscosity when compared to a polymer in the prior art.

EXAMPLE 9

Synergy in Surfactant and Acid Solutions

The instant copolymer samples are evaluated (at various concentrations) in simple surfactant solutions plus acid to measure any increase in thickening efficiency when used in combination with various surfactants. The surfactants chosen are typically used in home care formulations. The concentration is 1.5% active polymer based on weight and 5% active ARQUAD T-50 based on weight. The surfactant studied is ARQUAD T-50=Tallow tri-methyl ammonium chloride 2-propanol. The pH is adjusted to a pH=3 with 50% HCl. The viscosity measurements are made using a Brookfield RVT, spindle 2 (speed 20 rpm).

| 1.5% Active Polymer in 5% w/w ARQUAD T-50 - pH 3 with 50% HCL | | |
|---|---|---|
| Example | Day 0 viscosity (cPs) | Day 1 viscosity (cPs) |
| None | 28 | 28 |
| Comparative Example 1 | 132 | 160 |
| Example 2 | 198 | 234 |
| Example 3 | 154 | 148 |
| Example 4 | 174 | 154 |

The instant copolymers show an improved and sustained increase in acidic solution viscosity when compared to a polymer in the prior art.

EXAMPLE 10

Synergy in Surfactant and Acid Solutions

The instant copolymer samples are evaluated (at various concentrations) in simple surfactant solutions plus acid to measure any increase in thickening efficiency when used in combination with various surfactants. The surfactants chosen are typically used in home care formulations. The concentration is 1.5% active polymer based on weight and 5% active ARQUAD 16-29 based on weight. The surfactant studied is ARQUAD 16-29=Hexadecyltrimethyl ammonium chloride. The pH is adjusted to a pH=3 with 50% HCl. The viscosity measurements are made using a Brookfield RVT, spindle 2 (speed 20 rpm).

| 1.5% Active Polymer in 5% w/w ARQUAD 16-29 - pH 3 with 50% HCL | | |
|---|---|---|
| Example | Day 0 viscosity (cPs) | Day 1 viscosity (cPs) |
| None | 52 | 52 |
| Comparative Example 1 | 204 | 196 |
| Example 2 | 268 | 328 |
| Example 3 | 220 | 210 |
| Example 4 | 260 | 276 |

The instant copolymers show an improved and sustained increase in acidic solution viscosity when compared to a polymer in the prior art.

EXAMPLE 11

Synergy in Surfactant and Acid Solutions

The instant copolymer samples are evaluated (at various concentrations) in simple surfactant solutions plus acid to measure any increase in thickening efficiency when used in combination with various surfactants. The surfactants chosen are typically used in home care formulations. The concentration is 1.5% active polymer based on weight and 4% active CRODAQUAT TES based on weight. The surfactant studied is CRODAQUAT TES=Polyoxyethylene (16) tallow ethylmonium ethosulfate. The pH is adjusted to a pH=3 with 50% HCl. The viscosity measurements are made using a Brookfield RVT, spindle 2 (speed 20 rpm).

1.5% Active Polymer in 4% w/w CRODAQUAT TES - pH 3 with 50% HCL

| Example | Day 0 viscosity (cPs) | Day 1 viscosity (cPs) |
|---|---|---|
| None | 20 | 20 |
| Comparative Example 1 | 124 | 152 |
| Example 2 | 150 | 154 |
| Example 3 | 106 | 122 |
| Example 4 | 132 | 128 |

The instant copolymers show an improved and sustained increase in acidic solution viscosity when compared to a polymer in the prior art.

EXAMPLE 12

Thickening Efficiency in Commercial Fabric Conditioner Formulations

The instant co-polymers are evaluated in commercial fabric conditioner formulations to study the thickening efficiency of finished commercial fabric conditioner formulations. The fabric conditioners tested are Lenor (regular summer breeze—Procter & Gamble PLC), Comfort pure (Unilever PLC) and Co-op own label bluebell mist (made for the Co-op in the UK) (typically having a pH of 3). The concentration is 0.4% active polymer based on weight of the total formulation.

Thickening Efficiency in Commercial Fabric Conditioner Formulations

| 0.4% w/w | Viscosity (cPs) No polymer | Viscosity (cPs) Comparative Example 1 | Viscosity (cPs) Example 2 |
|---|---|---|---|
| Commercial Fabric Conditioner | | | |
| Lenor fabric conditioner | 44 | 112 | 166 |
| Comfort pure fabric conditioner | 130 | 420 | 502 |
| Co-op fabric conditioner | 74 | 338 | 348 |

The results indicate that the instant copolymers give an increased thickening efficiency over a polymer of the prior art in a finished commercial fabric conditioner formulation.

EXAMPLE 13

Acidic Skin Care Emulsion

This example illustrates the use of about 0.5 to about 0.6 active weight % the Inventive Copolymers in an acidic skin care emulsion containing about 5% alpha-hydroxy acid (lactic acid) in the formulation shown below.

| Ingredient INCI/Trade Name | Wt % |
|---|---|
| 1. Water, deionized, to 100% | q.s. |
| 2. Mineral Oil, USP | 15 |
| 3. Glyceryl stearate, acid stable, self-emulsifying (Note 1) | 3.5 |
| 4. Cetyl alcohol | 2.5 |
| 5. Dow Corning 1401 fluid (Note 2) | 1 |

-continued

| Ingredient INCI/Trade Name | Wt % |
|---|---|
| 6. Metal ion chelating agent | 0.05 |
| 7. Propylene glycol | 4 |
| 8. Instant Copolymer (active %) | 0.5-0.6 |
| 9. Lactic acid (85%) | 6 |
| 10. Fragrance | q.s |
| 11. NH4OH (30%) to about pH 3-3.5 | q.s. | q.s. = quantity sufficient to meet the requirement
(Note 1). Preferably INCI compounds, Glyceryl Stearate (and) PEG-100 Stearate, such as ARLACEL 165 sold by Uniqema.
(Note 2). Trade name of Dow Corning Corp. for INCI name mixture Cyclomethicone (and) Dimethiconol.

The formulation is prepared at a temperature in the range of about 55 to about 65 C. by separately preparing at elevated temperatures an oil phase containing ingredients no. 2, 3, 4 and 5 and a water phase containing ingredients no. 1, 6, 7, 8 and 9, and then adding the oil phase to the water phase, mixing until a homogenous emulsion formed. The emulsion is then cooled to about 30 C, perfumed with ingredient no. 10 and the final pH is adjusted with ingredient ammonium hydroxide, #11.

The viscosity of the lotion can be increased to a viscous cream by increasing the amount of Instant Copolymer as needed. The composition is judged suitable for use as an acidic skin care product of the type employing alpha-hydroxy acid (AHA), beta-hydroxy acid (BHA), and the like.

EXAMPLE 14

Fabric Softener

This example illustrates the cationic salt compatibility of the Instant Copolymers, employed as thickeners in an ester-quat-containing fabric softener composition having the formula as shown below.

| Ingredient | Wt % |
|---|---|
| Instant Copolymer | 0.25-0.35 (active) |
| Water, deionized, to 100% | q.s. |
| Glycolic acid (50%) to about pH 3 | q.s. |
| DEHYQUART AU35 (35%) Note 3) | 5 |

Note 3). Trade name for the esterquat, Methyltriethanolammonium methyl sulfate dialkyl ester, sold by Cognis Corp.

The composition is prepared by neutralizing the Instant Copolymer in water with glycolic acid to provide a gel having a pH of about 4, then the esterquat component is added to the gel and mixed until homogeneous. The pH of the homogeneous mixture is then adjusted to about pH 3 with glycolic acid.

EXAMPLE 15

Hair Conditioning Hair Setting Compositions

This example illustrates the uses of Instant Copolymers as a thickener in two acidic aqueous gels containing the hair fixative, polyvinylpyrrolidone (PVP), suitable for conditioning, fixing and styling human and/or animal hair. The compositions are shown below.

| Ingredients | Instant Example 17A | Instant Example 17B |
|---|---|---|
| INCI/Trade Name | Active Weight % | Active Weight % |
| Water, deionized, to 100% | q.s. | q.s. |

-continued

| Ingredients | Instant Example 17A | Instant Example 17B |
|---|---|---|
| Instant Copolymer | 2 | 2 |
| PVP | 3 | 3 |
| CTAC | 1 | 0 |
| Polyquaternium-11 (Note 4) | 0 | 0.5 |
| Preservative | q.s. | q.s. |
| Glycolic acid (50%) | To about pH 4.5 | To about pH 4.3 |

(Note 4). INCI name for quaternized vinyl pyrrolidone/dimethylaminoethyl methacrylate, copolymer, neutralized sold under the trade name, GAFQUAT 755N by International Specialty Products.

Each composition is prepared by admixing all of the ingredients, except for the glycolic acid in the water, and then adjusting the pH downward with the glycolic acid. Both of the products are smoothly spreadable and free of any unaesthetic "stringy" character and provide good hair setting efficacy.

EXAMPLE 16

Biocidal Compatibility

This example illustrates the compatibility of Instant Copolymers with cationic biocidal salts in four formulations (Ex. 18A, 18B, 18C and 18D) shown below.

| (INCI/Trade Name) | Weight % Active Ingredient | | | |
|---|---|---|---|---|
| | Ex. 18A | Ex. 18B | Ex. 18C | Ex. 18D |
| Water, deionized, to 100% | q.s. | q.s. | q.s. | q.s. |
| Instant Copolymer | 0.75 | 0.75 | 0.75 | 0.75 |
| Didecyldimonium chloride (Note 5) | 0.1 | 0.3 | 0 | 0 |
| Benzalkonium chloride (Note 6) | 0 | 0 | 0.1 | 0.3 |
| Glycolic acid (50%) to pH = 4-4.5 | q.s. | q.s. | q.s. | q.s. |

(Note 5). INCI name for Didecyldimethyl ammonium chloride, sold under the trade name, BARDAC 2250 by Lonza, Inc.
(Note 6). INCI name for Alkyldimethyl benzyl ammonium chloride mixture (C14, 50%; C12, 40%; C16 10%) sold under the trade name, BARQUAT MB 50, by Lonza, Inc.

All of the compositions are homogeneous and have smooth flow characteristics.

EXAMPLE 17

Hair Conditioner Formulation

This example illustrates the use of the Instant Copolymers in the hair conditioner formulations and in the active amounts shown below.

| Ingredient (INCI/Trade Name | Weight % Active | | |
|---|---|---|---|
| | Ex. 19A | Ex. 19B | Ex. 19C |
| 1a. Instant Example 3 | 1 | 1 | 0 |
| 1b. Instant Example 2 | 0 | 0 | 1.5 |
| 2. Water, deionized, | q.s. to 100% | q.s. to 100% | q.s. to 100% |
| 3. Dicetyldimethyl-ammonium chloride | 3.3 | 3.3 | 3.3 |
| 4. Propylene glycol | 0.5 | 0.5 | 0.5 |
| 5. Stearamidopropyl-dimethyl amine | 0.5 | 0.5 | 0.5 |
| 6. Perfume | q.s. | q.s. | q.s. |
| 7. Cyclomethicone (Note 7) | 2 | 0 | 2 |
| 8. Panthenol | 0.1 | 0.1 | 0.1 |
| 9. Glycolic acid (50%) to pH = 4.5 | q.s. | q.s. | q.s. |
| 10. Preservative | q.s. | q.s. | q.s. |

(Note 7). INCI name for cyclic dimethyl polysiloxane compound having an average of 3-6 siloxane units, such as SILICONE SF1173 (General Electric).

The compositions are prepared by admixing ingredient nos. 2, 3, 4 and 5 together at a temperature in the range of about 62 to about 63 C until homogeneous, cooling the admixture to a temperature in the range of about 46 to about 47 C, then admixing in either ingredient no. 1a or 1b, as indicated, ingredients no. 7, when present, no. 8, no. 6 and no. 10 until homogeneous. The pH of the product is then adjusted to about pH 4.5 with ingredient no. 9.

All of the compositions are smooth in texture and flowable.

EXAMPLE 18

Hair Conditioner

This example illustrates the use of the Instant Copolymers at two concentrations (Ex. 20A, 20B) in the formulation shown below, suitable for use as a hair conditioner.

| Ingredient (INCI/Trade Name) | Weight % Active |
|---|---|
| Phase A | |
| Water, deionized, to 100% | q.s. |
| Instant Example 3 | 1-1.5 |
| Phase B | |
| Stearalkonium Chloride | 3 |
| Polyquaternium-28 (Note 8) | 1 |
| Panthenol | 1 |
| UV Absorber | q.s. |
| Sodium lactate | 0.5 |
| Dow Corning 1401 fluid (Note 9) | 30 |
| Phase C | |
| Lactic Acid to pH = 4.5 | q.s. |

(Note 8). INCI name for quaternary ammonium salt consisting of vinyl pyrrolidone and dimethylaminopropyl methacylamide monomers.
(Note 9). Trade name of Dow Corning for INCI mixtures Cyclomethicone (and) Dimethiconol.

The compositions are prepared by premixing the components of Phase A and heating the mixture to a temperature in the range of about 55 to about 60 C. The components of Phase B are added in the order listed, stirring the batch until homogeneous, the batch is then cooled to a temperature of about 30 C, and the pH is adjusted to about 4.5 with Phase C. The final product is a creamy-white in appearance with very good flow characteristics and silky to the touch.

EXAMPLE 19

Gel

This example illustrates the use of the Instant Copolymers in three low-pH aqueous gels (Ex. 21A, 21B, and 21C) in the active polymer weight % amounts shown below.

| Ingredient | Active Weight % | | |
|---|---|---|---|
| | Ex. 21A | Ex. 21B | Ex. 21C |
| Instant Copolymer | 2 | 2.5 | 3 |
| Deionized, water, to 100% | q.s. | q.s. | q.s. |
| Citric acid (50%) | 25 | 25 | 25 |
| pH | 1.8 | 1.8 | 1.5 |

The gels are judged suitable for use as a general purpose rust and stain removal acid cleaner, such as an acid toilet bowl cleaner, truck cleaner, tank car cleaner, floor cleaner and the like.

The aqueous gels can also be prepared with inorganic mineral acids, such as hydrochloric acid, sulfuric acid or phosphoric acid, instead of citric acid, to produce economical low pH gels suitable for rust removal or industrial applications.

EXAMPLE 20

Clear Bath Gel

This example illustrates the use of the Instant Copolymers at an active polymer weight of about 1% in a clear gel composition. The gel composition is prepared at varying pH levels (Gels 22A, 22B, and 22C) employing the formula shown below.

| Ingredient (INCI/Trade Name) | Weight % |
|---|---|
| 1. Water, deionized, to 100% | q.s. |
| 2. Instant Copolymer (active %) | 1 |
| 3. Sodium laureth-3 sulfate (28%) | 40 |
| 4. Glycolic acid (50%) to about pH 4 | 2.5 |
| 5. Cocamidopropyl betaine (35%) | 14.3 |
| 6. Preservative | q.s. |
| 7. Sodium hydroxide to about pH 5-5.6, As indicated below for Gels 22B and 22C | q.s. |

Gel 20A

Gel 20A is prepared as follows. Ingredient nos. 1 and 2 are premixed, ingredient no. 3 is added to the premix with gentle mixing and then the mixture is neutralized to about pH 4 with Ingredient No. 4. Ingredient nos. 6 and 7 are then added to the neutralized polymer gel with stir mixing until the gel is homogeneous and clear.

Gel 20B

Gel 20B is prepared by adjusting the pH of the previously prepared clear Gel 20A with ingredient no. 7 to about pH 5.2.

Gel 20C

Gel 20C is prepared by further adjusting the pH of the remaining previously prepared Gel 20B with ingredient no. 7 to about pH 5.6. The turbidity value for each of Gels 20A, 20B and 20C is low; therefore, all of the gels are judged suitable for use as clear bath gels.

EXAMPLE 21

Shampoo

The example illustrates the use of the Instant Copolymers at an active polymer weight of about 1% in a shampoo composition having the formula shown below.

| Ingredient (INCI/Trade Name) | Weight % |
|---|---|
| 1. Water, deionized, to 100% | q.s. |
| 2. Sodium laureth-3 sulfate (28%) | 40 |
| 3. Cocamidopropyl betaine (35%) | 5 |
| 4. Cocamide DEA | 3 |
| 5. Instant Copolymer (active %) | 1 |
| 6. Citric acid (50%) to about pH 4-4.6 | q.s. |
| 7. Fragrance | q.s. |

The shampoo is prepared by admixing the ingredients in the order listed, then adjusting the pH, as needed, with ingredient no. 6, and mixing until homogenous. The pH of the completed shampoo is about 4.6. The turbidity value for the shampoo formulation is low; therefore, the shampoo is judged suitable for use as an all-purpose type shampoo.

EXAMPLE 22

Anti-Dandruff Shampoo

This example illustrates the use of Instant Copolymers at an active polymer weight of about 1% in an anti-dandruff shampoo composition, containing zinc pyrithione as the active dandruff control ingredient, and having the following formula shown below.

| Ingredient (INCI/Trade Name) | Weight % |
|---|---|
| 1. Water, deionized, to 100% | q.s. |
| 2. Instant Copolymer (active %) | 1 |
| 3. Glycolic acid (50%) to about pH 4-4.5 | q.s. |
| 4. PLANTAREN PS-100 (50%) (Note 10) | 25 |
| 5. Cocamide DEA | 3 |
| 6. Cocamidopropyl betaine (35%) | 5 |
| 7. Zinc pyrithione (48%) (Note 11) | 2 |
| 8. Preservative | q.s. |
| 9. Fragrance | q.s. |

(Note 10). Trade name of nonionic/anionic surfactant blend of Alkyl Polyglycoside and Ammonium Laureth Sulfate having an alkyl distribution of C8-C16, sold by Cognis, Corp.
(Note 11). INCI name of compound sold under the trade name ZINC OMADINE as a 48% dispersion by Arch Chemicals, Inc.

The shampoo is prepared by admixing the ingredients in the order listed, then adjusting the pH with ingredient no. 3, as needed, and mixing until homogenous.

EXAMPLE 23

Conditioning Shampoo

The example illustrates the use of Instant Copolymers at an active polymer weight of about 1.5% in a conditioning shampoo composition having the formula shown below.

| Ingredient (INCI/Trade Name) | Weight % |
|---|---|
| Phase A | |
| 1. Water, deionized, to 100% | q.s. |
| 2. Instant Copolymer (active %) | 1.5 |
| 3. Sodium laureth-3 sulfate (28%) | 30 |
| 4. Glycolic acid (50%) to about pH 4.5 | q.s. |
| Phase B | |
| 5. Cocamidopropyl hydroxysultaine (50%) | 10 |
| 6. Disodium laureth sulfosuccinate (40%) (Note 12) | 10 |
| Phase C | |
| 7. Water, deionized, to 100% | 3 |
| 8. Mica and Titanium dioxide (Note 13) | 0.2 |

| Ingredient (INCI/Trade Name) | Weight % |
|---|---|
| Phase D | |
| 9. Dimethicone (60,000 cSt) | 3 |
| 10. Preservative | q.s. |
| 11. Fragrance | q.s. |
| 12. Citric acid (50%) to about pH 4.5 | q.s. |

(Note 12). INCI name for the disodium salt of an ethoxylated lauryl alcohol half ester of sulfosuccinic acid, having an average of ethylene oxide units between 1 and 4.
(Note 13). Mixture sold under the trade name TIMIRON MP-115 Starluster by Rona/Merck KGaA reportedly having 69-75% Mica and 25-31% Titanium dioxide.

The shampoo is prepared as follows. Phase A is prepared by admixing ingredients no. 1 and 2, adding ingredient no. 3 with gentle mixing and then acidifying the mixture to about pH 4.5 with ingredient no. 4. The components of phase B are added to phase A with mixing, in the order indicated. Phase C is separately prepared by premixing ingredients no. 7 and 8, and then adding phase C to the mixture of phases A and B. The remaining ingredients no. 9, 10 and 11 of phase D are added to the batch in the order listed and the pH adjusted to about 4.5 with ingredient 12.

The shampoo is judged suitable for use as a conditioning shampoo of the type commonly referred to as "two-in-one" conditioning shampoo.

EXAMPLE 24

Cationic Cream Conditioner

This example illustrates the use of the Instant Copolymers at an active polymer weight of about 1.6% in a cationic, creamy conditioner formulation shown below.

| Ingredient | Wt % as is basis |
|---|---|
| 1. Water, deionized, to 100% | q.s. |
| 2. Glycerin | 3.8 |
| 3. Propylene Glycol | 2 |
| 4. Stearalkonium Chloride (25%) | 2.3 |
| 5. Preservative | q.s. |
| 6. Mineral Oil (light) | 5 |
| 7. Instant Copolymer (active weight %) | 1.6 |
| 8. Citric Acid (50%) to pH 3.2-3.8 | q.s. |

The cream formulation is prepared by mixing ingredient nos. 1, 2 and 3 without aeration. Ingredient no. 4 is added to the mixture and admixed thoroughly before adding ingredients nos. 5 and 6. Ingredient no. 7 is then added to the foregoing mixture and mixed thoroughly before adjusting the pH range. The resulting formulation has a white creamy appearance and smooth consistency.

EXAMPLE 25

Cationic Conditioner

This example illustrates the use of the Instant Copolymers at an active polymer weight of about 2% in a cationic conditioner formulation shown below.

| Ingredient | Wt % as is basis |
|---|---|
| 1. Water, deionized, to 100% | q.s. |
| 2. Glycerin | 3.8 |
| 3. Propylene Glycol | 2 |
| 4. CTAC | 2 |
| 5. Preservative | q.s. |
| 6. Instant Copolymer (active weight %) | 2 |
| 7. Citric Acid (50%) to pH 3.5 | q.s. |

The clear conditioner formulation is prepared by mixing ingredient nos. 1, 2 and 3 without aeration. Ingredient no. 4 is added to the mixture and admixed thoroughly before adding ingredient no. 5. Ingredient no. 6 is then added to the foregoing mixture and mixed thoroughly before adjusting the pH with ingredient no. 7. The resulting formulation is substantially clear and has a smooth consistency.

EXAMPLE 26

Hair Care Setting and Conditioning Compositions

This example illustrates the use of the Instant Copolymers at an active polymer weight of about 3% in aqueous hair care conditioning compositions, useful for setting, styling, and/or conditioning hair. In one study, Instant Example 3 is used alone, (Ex. 26A), as the sole conditioning, rheology modifying, film-forming hair-fixative polymer. In additional studies, Instant Example 3 is used in combination with an active polymer weight of about 3% of a commercial nonionic auxiliary hair-fixative polymer (Exs. 26B-26D); an active polymer weight of about 3% of a commercial cationic auxiliary hair-fixative polymer (Exs. 26E-26L); an active polymer weight of about 1% or 3% of a commercial amphoteric auxiliary hair-fixative polymer (Exs. 26M and 26N, respectively); or an active polymer weight of about 1% or about 3% of a commercial auxiliary cationic conditioning polymer (Exs. 26O-26T), in the aqueous formulation and in the amounts shown below.

| Ingredients (INCI/Trade Name) | Wt. % |
|---|---|
| 1. Instant Copolymer (active wt. %) | 3 |
| 2. Water, deionized, to 100% | q.s. |
| 3. Commercial polymer (active wt. %), identified in Table below Exs. 26B-26L, 26N-26S | 3 |
| Ex. 26M, Ex. 26T | 1 |
| 4. Preservative | q.s. |
| 5. Glycolic acid (50%) to pH 4-6 | q.s. |

Each of the compositions is prepared by dispersing in water the commercial auxiliary polymer ingredient no. 3 indicated in the Table below and mixing to provide an aqueous polymer solution, the Instant Copolymer is then admixed into the aqueous polymer solution, the pH is adjusted to about 5 with ingredient no. 5, ingredient no. 4 is then added and the pH adjusted with ingredient no. 5 to a range of about 4 to about 6, as needed. The appearance of the composition is noted, and after 24 hours, the Brookfield viscosity is measured, as well as turbidity, clarity, and hair setting efficacy.

| Ex. No. | Commercial Polymer (INCI/Tradename) |
|---|---|
| 26A | None Instant Copolymer Only |
| 26B | PVP (Note 14) |
| 26C | PVP (Note 15) |
| 26D | PVP/VA (Note 16) |

-continued

| Ex. No. | Commercial Polymer (INCI/Tradename) |
|---|---|
| 26E | Polyquaternium-11 (Note 4) |
| 26F | Polyquaternium-11 (Note 17) |
| 26G | Polyquaternium-28 (Note 18) |
| 26H | Polyquaternium-4 (Note 19) |
| 26I | Polyquaternium-16 (Note 20) |
| 26J | Polyquaternium-46 (Note 21) |
| 26K | Polyquaternium-55 (Note 22) |
| 26L | Gaffix VC-713 (Note 23) |
| 26M | Amphomer .RTM. (Note 24) |
| 26N | Diaformer Z-731 (Note 25) |
| 26O | Polyquaternium-10 (Note 26) |
| 26P | Polyquaternium-39 (Note 27) |
| 26Q | Polyquaternium-7 (Note 28) |
| 26R | JAGUAR EXCEL (Note 29) |
| 26S | Chitosan PCA (Note 30) |
| 26T | Polyquaternium-10 (Note 31) |

(Note 14). PVP K90, BASF (weight average molecular weight reportedly about 1,300,000 Daltons).
(Note 15). PVP K30, BASF (weight average molecular weight reportedly about 60,000 Daltons).
(Note 16). PVP 73W, BASF.
(Note 17). GAFQUAT 734N, ISP, supplied as 50% in ethanol.
(Note 18). GAFQUAT HS-100, ISP.
(Note 19). CELQUAT H-100, National Starch.
(Note 20). LUVIQUAT FC-370, BASF.
(Note 21). LUVIQUAT HOLD, BASF.
(Note 22). STYLEZE W20, ISP.
(Note 23). Trade name for a cationic fixative polymer having the INCI name vinylcaprolactam/PVP/dimethylaminoethylmethacrylate copolymer sold by ISP.
(Note 24). Trade name for an amphoteric polymer having the INCI name octylacryamide/acrylates/butylaminoethylmethacrylate copolymer, sold by National Starch.
(Note 25). Trade name for an amphoteric polymer, supplied as 40% in ethanol, having the INCI name Arcylates/Lauryl Acrylate/Stearyl Acrylate/Ethylamine Oxide Metharcylate Copolymer sold by Clariant.
(Note 26). UCARE Polymer JR-400, Amerchol.
(Note 27). MERQUAT 3330, Ondeo Nalco.
(Note 28). MACKERNIUM 007, McIntyre Group, Ltd.
(Note 29). Trade name for a quaternized guar derivative having the INCI name, Guar hydroxypropyltrimonium chloride, sold by Rhodia.
(Note 30). KYTAMER PC, Amerchol.
(Note 31). CELQUAT SC-230M, National Starch & Chemical.

EX. 26A

The aqueous composition containing the Instant Copolymer as the sole conditioning, fixative polymer has a pH of about 4.1 and is a clear gel, and, surprisingly, provides excellent hair setting efficacy.

EXS. 26B-26D

The aqueous compositions containing the Instant Copolymer and the commercial nonionic polymer, PVP (Ex. 26B, 26C) or PVP/VA (Ex. 26D) have a pH in the range of about 4.3 to about 5.5, and are substantially clear gels.

EXS. 26E-26L

The compositions containing the Instant Copolymer and commercial cationic fixative polymers have a pH in the range of about 4.1 to about 4.4. The compositions of Exs. 28E-28L are substantially clear.

EXS. 26M-26N

The gel compositions containing the Instant Copolymer and amphoteric polymer have a pH of about 4.2 and about 4.4.

EXS. 26O-26T

The compositions of Exs. 26O-26T containing the Instant Copolymer and cationic conditioning polymers have a pH of about 4.2 to about 4.3.

Hydroalcoholic Compositions

In a second study, the formulations of Exs. 26A-26T are prepared as hydroalcoholic compositions by repeating the procedure described above, except that, in step 1, the commercial polymers are dispersed in a mixture of ethanol SD-40 and water, so that the final hydroalcoholic hair care composition contains about 10 weight percent ethanol.

EXAMPLE 27

Hair Conditioner Compositions

This example illustrates the use of the Instant Copolymers in hair conditioner compositions, at an active polymer weight of about 2% as the sole conditioning agent (Ex. 27A), and in combination with an added dimethicone copolyol (Exs. 27B, 27C), and in combination with both added dimethicone copolyol and quaternary ammonium compound (Exs. 27D, 27E) in the amounts shown below.

| | Weight % | | | | |
|---|---|---|---|---|---|
| Ingredient (INCI/Tradename) | EX. 27A | EX. 27B | EX. 27C | EX. 27D | EX. 27E |
| 1. Deionized, Water, to 100% | q.s. | q.s. | q.s. | q.s. | q.s. |
| 2. Propylene glycol | 2 | 2 | 2 | 0 | 0 |
| 3. Varisoft Clear (Active Weight %) (Note 32) | 0 | 0 | 0 | 0.6 | 0.3 |
| 4. Polyquaternium-39 (Note 26) | 0 | 0 | 0 | 2.5 | 0 |
| 5. PEG-7 Glycerylcocoate (Note 33) | 3 | 3 | 3 | 2 | 2 |
| 6. Glycerin | 3 | 3 | 3 | 2 | 2 |
| 7. Instant Copolymer (Active Weight %) | 2 | 2 | 2 | 2 | 2 |
| 8. D-Panthenol | 2 | 2 | 2 | 1 | 1 |
| 9. PEG-12 Dimethicone (Note 34) | 0 | 1 | 3 | 1 | 1 |
| 10. Preservative | q.s. | q.s. | q.s. | q.s. | q.s. |
| 11. Chelating Agent | q.s. | q.s. | q.s. | q.s. | q.s. |
| 12. Glycolic acid (50%) to pH | q.s. | q.s. | q.s. | q.s. | q.s. |
| 13. Fragrance | q.s. | q.s. | q.s. | q.s. | q.s. |

(Note 32). Trade name for a mixture having the INCI name, Palmitamidopropyl trimonium chloride; and PPG-3 myristylether and trimethylpentanolhydroxyethyl ether sold by Degussa Care Specialties.
(Note 33) CETIOL HE, Cognis.
(Note 34) DOW CORNING 193, Dow Corning.

The compositions are prepared by gently admixing the Instant Copolymer and water, partially neutralizing the polymer solution with ingredient no. 12 to a pH of about 5, then admixing the remaining ingredients in the order listed, and adjusting the pH to about 4 as needed with Ingredient No. 12. The compositions are substantially clear after being prepared.

EXAMPLE 28

Cationic Conditioner Compositions

This example illustrates the compatibility of various concentrations of the Instant Copolymers with various cationic quaternary ammonium compounds in the formulations and amounts shown below.

| | Weight % | | | | | |
|---|---|---|---|---|---|---|
| Ingredient (INCI/Tradename) | EX. 28A | EX. 28B | EX. 28C | EX. 28D | EX. 28E | EX. 28F |
| Part A | | | | | | |
| 1. Deionized Water to 100% | q.s. | q.s. | q.s. | q.s. | q.s. | q.s. |
| 2. Instant Copolymer | 1 | 1 | 0.6 | 0.3 | 0.3 | 0.3 |
| 3. Propylene glycol | 2.5 | 2.5 | 2.5 | 2.5 | 2.5 | 2.5 |
| 4. CTAC (Note 35) | 1 | 0 | 1 | 1 | 0 | 0 |
| 5. Quaternium-18 (Note 36) | 0 | 1 | 0 | 0 | 0 | 0 |

-continued

| Ingredient (INCI/Tradename) | Weight % | | | | | |
|---|---|---|---|---|---|---|
| | EX. 28A | EX. 28B | EX. 28C | EX. 28D | EX. 28E | EX. 28F |
| 6. BTAC (Note 37) | 0 | 0 | 0 | 0 | 1 | 0 |
| 7. Quaternium-31 (Note 38) | 0 | 0 | 0 | 0 | 0 | 1 |
| Part B | | | | | | |
| 8. Cetyl alcohol | 2.2 | 2.2 | 1.1 | 1.1 | 1.1 | 1.1 |
| 9. Stearyl alcohol | 1.25 | 1.25 | 0.63 | 0.63 | 0.63 | 0.63 |
| 10. Hydrogenated Vegetable Oil | 1.2 | 1.2 | 0.6 | 0.6 | 0.6 | 0.6 |
| 11. Caprylic/capric triglyceride (Note 39) | 3.4 | 3.4 | 1.68 | 1.68 | 1.68 | 1.68 |
| Part C | | | | | | |
| 12. Preservative | q.s. | q.s. | q.s. | q.s. | q.s. | q.s. |
| Part D | | | | | | |
| 13. Citric Acid (10%) to pH 4-4.4 | q.s. | q.s. | q.s. | q.s. | q.s. | q.s. |

(Note 35). CTAC refers to Cetrimonium chloride.
(Note 36). INCI name for distearyldimethyl ammonium chloride.
(Note 37). BTAC refers to the quaternary ammonium compound having the INCI name
(Note 38). INCI name for dicetyldimethyl ammonium chloride. Behentrimonium chloride, assigned to N,N,N-trimethyl-1-docosaminium chloride.
(Note 39). INCI name for product sold under the tradename NEOBEE M-5 by the Stepan Company.

The compositions are manufactured as follows. Part A is prepared by gradually dispersing the Instant Copolymer (Ingredient No. 2) into water with moderate mixing agitation and mixing until a clear solution resulted. The remaining ingredients of Part A are then added and the mixture is heated to a temperature in the range of about 65 to about 70 C. In a separate vessel, Part B is prepared by admixing the ingredients of Part B and heating the mixture to a temperature in the range of about 65 to about 70 C, mixing until a solid-free homogeneous mixture is obtained. Part B is then added to Part A with moderate mixing agitation and mixed until homogeneous (about 15 minutes). The resulting mixture is then cooled to a temperature in the range of about 35 to about 40 C. Part C is then added and the pH is adjusted to a range of about 4 to about 4.4 by adding Part D, as needed.

EXAMPLE 29

Sanitizer Compositions

This example illustrates the use of Instant Copolymers Example 1 and Example 2 in alcohol-free, antimicrobial, sanitizer formulations and in the active amounts shown below.

| Active Ingredient (INCI/Trade Name) | Weight % Active | | | | |
|---|---|---|---|---|---|
| | Ex. 29A | Ex. 29B | Ex. 29C | Ex. 29D | Ex. 29E |
| 1. Water, deionized, to 100% | q.s. | q.s. | q.s. | q.s. | q.s. |
| 2a. Instant Example 1 | 0 | 0 | 0 | 0 | 2 |
| 2b. Instant Example 2 | 1 | 1.5 | 1.75 | 2 | 0 |
| 3. Benzethonium Chloride) (Note 40 | 0.3 | 0.3 | 0.3 | 0.3 | 0.3 |
| 4. Glycolic Acid (50% to pH | q.s. | q.s. | q.s. | q.s. | q.s. |
| 5. PEG-33 (and) PEG-8 Dimethicone (and) PEG-14 (Note 41) | 0 | 1 | 0 | 2 | 0 |
| pH | 4.6 | 4.4 | 4.5 | 4.6 | 4.4 |

(Note 40). INCI name for Diisobutylphenoxyethoxy-ethyldimethylbenzylammonium chloride monohydrate sold under the tradename LONZAGARD by Lonza, Inc.
(Note 41). INCI name for a product sold by Noveon, Inc.

The compositions are prepared by admixing ingredient no. 3 with ingredient no. 1 at ambient room temperature until homogeneous (about 15 minutes), then adding ingredient no. 2, and admixing until homogenous, adjusting the pH with ingredient no. 4 to a range of about 4.4 to about 4.7 and then measuring the pH, viscosity and turbidity values. Ingredient no. 5 is then added to the formulation of Exs. 31B and 31D, as indicated above.

The compositions are judged suitable as sanitizing compositions, and particularly suitable as hand sanitizers.

EXAMPLE 30

Acidic Surfactant Skin Cleanser

This example illustrates the compatibility of the Instant Copolymers, with anionic surfactants in an acidic surfactant skin cleanser formulation, containing an amphoteric hydroxy complex of alpha-hydroxy acid (Lactic acid) and L-Arginine.

| Ingredient INCI/Trade Name | Wt % |
|---|---|
| 1. Water, deionized, to 100% | q.s. |
| 2. Glycol Distearate(and)Glycerine(and)Laureth-4 | 1 |
| 3. Coco-Glucoside(and)Glyceryl Oleate (Note 42) | 2 |
| 4. Cocamidopropylamine Oxide (Note 43) | 1 |
| 5. Sodium Laureth Sulfate(and)Cocamidopropyl | 23.5 |
| 6. Lactic Acid(and)L-Arginine blend (Note 44) | 10 |
| 7. Sodium Hydroxide (50%) to pH | q.s. |
| 8. Preservative | q.s. |
| 9. Instant Copolymer (Active Weight %) | 1 |

(Note 42). INCI name for product sold under the tradename LAMESOFT PO-65 (65%) by Cognis.
(Note 43). INCI name for product sold under the tradename STANDAMOX CAW by Cognis.
(Note 44). INCI name for the product sold under the tradename AHCARE L-65 by Cognis.

The composition is prepared by dispersing in water, ingredients nos. 2 through 6 in the order shown, mixing well between each addition. The pH of the admixture is adjusted to a range of about 3.8 to about 3.9 with ingredient no. 7. Ingredient no. 8 is then added, followed by the Instant Copolymer (no. 9), and the pH is then adjusted with ingredient no. 7 to a range of about 4.1 to about 4.2 as needed.

The composition is judged particularly suitable as a body cleanser, typically referred to as a body wash.

EXAMPLE 31

Mousse Formulation

| Ingredient INCI/Trade Name | Wt. % (as supplied) |
|---|---|
| 1. Water, deionized, to 100% | q.s. |
| 2. Instant Copolymer (Active Polymer Weight) | 0.5 |
| 3. Polyquaternium 11 (20% solids) | 20 |
| 4. SD alcohol | 6 |
| 5. Cocamidopropyl betaine (35%) | 0.5 |
| 6. PEG 40 Hydrogenated Castor Oil | 0.3 |
| 7. Citric Acid (50%) to pH | q.s. |
| 8. Preservative | q.s. |
| 9. Fragrance | q.s. |

The Instant Copolymer is dispersed into deionized water. Ingredient nos. 3, 4, and 5 are then added in the order listed, mixing after each addition until uniform. Ingredient no. 8 is added and mixed until the batch is uniform. Ingredients nos. 6 and 9 are premixed and added to the foregoing batch. The pH is adjusted to about 5 with citric acid. The formulation is judged suitable for use in a mousse product.

EXAMPLE 32

Shampoos for Color Treatment and Color Maintenance

This example illustrates two shampoos (32A and 32B) suitable for color treatment and color maintenance.

| Ingredient (INCI/Trade Name) | Wt. % as supplied 32A | Wt. % as supplied 32B |
|---|---|---|
| 1. Water, deionized, to 100% | q.s. | q.s. |
| 2. Instant Copolymer (Active Polymer Wt. %) | 1 | 1 |
| 3. Sodium Laureth Sulfate (Note 45) | 20 | 20 |
| 4. Lamesoft. RTM. PO-65 (Note 42) | 3 | 3 |
| 5. Cocamidopropyl Betaine | 5.5 | 5.5 |
| 6. Ammonium Laureth Sulfate (Note 46) | 15 | 15 |
| 7. EUPERLAN PK-3000 (Note 49) | 3 | 3 |
| 8. Tocopherol | 0.1. | 0.1. |
| 9. Preservative | q.s. | q.s. |
| 10. Sodium cocoyl hydrolyzed wheat (Note 47) | 0.5 | 0.5 |
| 11. C.I. Brown 17 (Note 48a) | 0.13 | 0 |
| 12. C.I. Blue 99 (Note 48b) | 0.13 | 0 |
| 13. C.I. Red 76 (Note 48c) | 0.2 | 0 |
| 14. Fragrance | q.s. | q.s. |
| 15. Citric Acid (50%) to pH | q.s. | q.s. |

(Note 45). INCI name for product sold under the tradename STANDAPOL ES-2 by Cognis.
(Note 46). INCI name for product sold under the tradename STANDAPOL EA-2 by Cognis.
(Note 47). INCI name for product sold under the tradename GLUADIN WK sold by Cognis.
(Note 48). INCI name for (a) ARIANOR Sienna Brown (b); ARIANOR Steel Blue (c); ARIANOR Madder Red, all sold by Warner Jenkinson Europe, Ltd.
(Note 49). INCI name for product sold under the tradename EUPERLAN PK-3000 by Cognis.

Shampoo 32A is prepared by dispersing the Instant Copolymer in the deionized water with gentle mixing, adding ingredient nos. 3 and 6 with mixing, partially neutralizing the mixture to pH of about 5 with citric acid, and then adding the remaining ingredient nos. 4, 5, 7, 8, 9 and 10 in the order listed. A blend of ingredient nos. 11, 12, 13 and fragrance is added into the mixture, and the pH adjusted to a range of about 4.7 to about 5.0 with ingredient no. 15.

Shampoo 32A is judged suitable for coloring the hair during use, and for maintaining the hair color through continued use as a treatment shampoo.

Shampoo 32B is prepared following the procedure of Shampoo 32A, except that no colorant dyes are present. Shampoo 32B is judged suitable for washing hair that has been colored or chemically treated without removing the color from the hair.

EXAMPLE 33

Shampoo Formulation Back-Alkaline Method

This example illustrates the use of the Instant Copolymer in a shampoo composition. It demonstrates that the viscosity, turbidity, and yield value can be improved by using a back-alkaline method of formulation.

| Phase A | Weight % |
|---|---|
| 1 Deionized water | q.s |
| 2. Instant Copolymer (active %) | 1.5 |
| 3. Sodium Laureth Sulfate (3 mole, 28%) | 30.00 |
| 4. Citric acid (50% by wt. in water) | 1.00 |

-continued

| | Weight % |
|---|---|
| Phase B | |
| 5. Cocamidopropyl Hydroxysultaine (50% by wt. in water) | 10.00 |
| 6. Disodium Laureth Sulfosuccinate (40% by wt. in water) | 10.00 |
| Phase C | |
| 7. Preservative | 0.50 |
| 8. Citric Acid (50% by wt. in water) to about pH 4 | |
| 9. NaOH (50% by wt. in water) to target pH | |

Select example formulations are prepared using the "Back-Alkaline" formulation technique. The Instant Copolymer at an active weight of about 1.5% is used as shown above. The shampoo is prepared as follows. Phase A is prepared by admixing ingredients No. 1 and 2, adding ingredient No. 3 with gentle mixing and then acidifying the mixture to about pH 4.5 with ingredient No. 4. The components of Phase B are added to Phase A with mixing, in the order indicated. Phase C is added to the batch in the order listed and the pH adjusted to about 4 with ingredient 8. The shampoo is prepared to about 4.0 pH with Citric acid and then raising pH upward with 50% NaOH solution.

EXAMPLES 34 AND 35

Shampoo Formulation (Back-Alkaline Method)

The shampoo compositions of Examples 34 and 35 are prepared as described in Example 33 except that Instant Examples 2 and 3 are utilized in the respective formulations. The shampoo formulations are then subjected to the back-alkaline thickening procedure described in Example 33.

EXAMPLES 36-38

Conditioning Shampoo Formulations (Back-Alkaline Method)

The example illustrates the use of the Instant Copolymers in a conditioning shampoo composition having the formula shown below. The shampoo (Example 36) is prepared as follows. Phase A is prepared by admixing ingredients nos. 1 and 2 and then adding ingredient no 3 with gentle mixing. Phase A is then acidified to a pH of about 4.5 with ingredient No. 4. The components of Phase B are then added to Phase A (with mixing) in the order indicated. Phase C is separately prepared by premixing ingredients no. 7 and 8 and then adding phase C to the mixture of Phases A and B. The remaining ingredients, nos. 9, 10 and 11, of Phase D are added to the batch in the indicated order and the pH is adjusted to about 4.8 with ingredient 12.

A portion of Example 36 is further adjusted to pH 4.1 with citric acid and a sample is taken and labeled Example 37.

A portion of Example 36 is treated with 50% NaOH to bring the final pH to 6.1 and a sample is taken and labeled Example 38.

| Phase A | Weight, % |
|---|---|
| 1. Deionized water | q.s |
| 2. Instant Copolymer (active %) | 1.5 |
| 3. Sodium Laureth Sulfate (3 mole, 28%) | 30.00 |
| 4. Citric acid (50% by wt. in water) | 1.00 |

-continued

| | Weight, % |
|---|---|
| Phase B | |
| 5. Cocamidopropyl Hydroxysultaine (50% by wt. in water) | 10.00 |
| 6. Disodium Laureth Sulfosuccinate (40% by wt. in water) | 10.00 |
| Phase C | |
| 7. Deionized water | 3.00 |
| 8. Mica and titanium dioxide (Note 19) | 0.20 |
| Phase D | |
| 9. Dimethicone (60,000 cSt) | 3.00 |
| 10. Preservative | 0.50 |
| 11. Fragrance | 0.50 |
| 12. Citric Acid (50% by wt. in water) to about pH 4.5 | 0.20 |
| 13. NaOH (50% by wt. in water) to target pH | |

EXAMPLE 39

Shower Gel formulation (Back-Alkaline Method)

A shower gel formulation is prepared utilizing the ingredients set forth below. Phase A is prepared by admixing ingredients No. 1 and 2, and then adding ingredient no. 3. with gentle mixing. The components of Phase B are added to Phase A with mixing, in the order indicated. The pH is adjusted with ingredient 9 in increments to about pH 4. The pH of the acidified composition is then raised in increments by the addition of ingredient 10.

| | Weight % |
|---|---|
| Phase A | |
| 1. Deionized water | q.s |
| 2. Instant Copolymer (active %) | 1.5 |
| 3. Sodium Laureth Sulfate (2 mole, 28%) | 40.00 |
| Phase B | |
| 4. Cocamidopropylbetaine (30% by wt. in water) | 16.67 |
| 5. Polyquaternium-39 (10% by wt. in water) | 2.10 |
| 6. Tetrasodium EDTA | 0.05 |
| 7. Preservative | 0.50 |
| 8. Gelatin Microcapsules with Vitamin E | 1.00 |
| 9. Citric Acid (50% by wt. in water) to pH 4 | q.s. |
| 10. NaOH (50% by wt. in water) to target pH | |

EXAMPLES 40 & 41

Shower Gel formulation (Back-Alkaline Method)

The same formulation steps are followed in these Examples as set forth in the preparation of the shower gel composition of Example 39 except that Instant Polymers 2 and 3 are used, respectively.

What is claimed is:

1. An aqueous personal care, household care, or fabric care composition comprising an effective amount of at least one copolymer of formula (II)

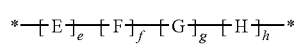 (II)

wherein e, f, g, and h represent the percentage by weight that each repeating unit or derived monomer is contained within the copolymer;

e, f, g, and h add up to total substantially 100 weight percent relative to the total weight of the copolymer;

e is from about 20% to about 80% by weight of the copolymer;

f is from about 20% to about 80% by weight of the copolymer;

g is from about 1% to about 15% by weight of the copolymer;

h is from about 1% to about 15% by weight of the copolymer;

* is a terminal catalyst residue;

E is 2-(tert-butylamino)ethyl methacrylate or salt thereof;

F is a hydrophobic nonionic vinyl monomer selected from the group consisting of ethyl (meth) acrylate and methyl (meth)acrylic and mixtures thereof;

G and H are an associative- vinyl monomer selected from the group consisting of cetyl polyethoxylated methacrylate (CEM), cetearyl polyethoxylated methacrylate (CSEM), stearyl polyethoxylated (meth)acrylate, arachidyl polyethoxylated (meth)acrylate, behenyl polyethoxylated methacrylate (BEM), lauryl polyethoxylated methacrylate (LEM), cerotyl polyethoxylated (meth)acrylate, monthanyl polyethoxylated (meth)acrylate, melissyl polyethoxylated (meth)acrylate, lacceryl polyethoxylated (meth) acrylate, tristyryl phenolpolyethoxylated methacrylate (TEM), hydrogenated castor oil polyethoxylated methacrylate (HCOEM), canola polyethoxylated (meth)acrylate, and cholesterol polyethoxylated methacrylate (CHEM), E, F, G, and H are covalently attached to each other;

with the proviso that G and H are not the same and optionally one or more crosslinking monomers.

2. A composition according to claim 1 where the copolymer of formula (II) is present in the personal care, household care, or fabric care composition in a concentration of about 0.0001 weight percent to about 50 weight percent based on the total composition by weight.

3. A composition according to claim 2 where the copolymer of formula (II) is present in the personal care, household care, or fabric care composition in a concentration of about 0.01 weight percent to about 25 weight percent based on the total composition by weight.

4. A composition according to claim 3 where the copolymers of formula (II) are present in the personal care, household care, or fabric care composition in a concentration of about 0.1 weight percent to about 7 weight percent based on the total composition by weight.

5. A composition according to claim 4 where the copolymers of formula (II) is present in the personal care, household care, or fabric care composition in a concentration of about 0.2 weight percent to about 5 weight percent based on the total composition by weight.

6. A composition according to claim 1 wherein the copolymers of formula (II) comprises a weight average molecular weight from about 1,000 to about 10 million.

7. A composition according to claim 6 wherein the copolymer of formula (II) comprises a weight average molecular weight from about 25,000 to about 5 million.

8. A composition according to claim 7 wherein the copolymers of formula (II) comprises a weight average molecular weight from about 50,000 to about 2 million.

9. A composition according to claim 8 wherein the copolymers of formula (II) comprises a weight average molecular weight from about 50,000 to about one million Daltons.

10. A composition according to claim 1 further comprising at least one dye, at least one pigment, or mixtures thereof.

11. A composition according to claim 1 wherein the personal care compositions are selected from the group consisting of hair care products, skin care products, antiaging products, skin protectants, skin color products, hair colorants, pigmented skin colorants bath and shower products, nail care products, hair-removal products, deodorants and antiperspirants, oral care products, facial and body hair bleach, sunless tanning compositions, skin depigmenting and lightening compositions, foot care products and foot and toenail conditioning compositions.

12. A composition according to claim 11 wherein the hair care products are selected from the group consisting of shampoos, two-in-one conditioning shampoos, post-shampoo rinses, setting and style maintenance agents, hair setting gels, hair setting sprays, pomades, conditioners, perms, relaxers and hair smoothing products.

13. A composition according to claim 1 wherein the fabric care compositions are selected from the group consisting laundry detergents, liquid fabric softeners, fabric softener sheets, ironing sprays, dry cleaning aids, antiwrinkle sprays and spot removers.

14. A composition according to claim 1 wherein the household care compositions are selected from the group consisting hard surface cleansers for the kitchen and bathroom, toilet bowl gels, tub and shower cleaners, hard water deposit removers, floor and tile cleansers, wall cleansers, floor and chrome fixture polishes, alkali-strippable vinyl floor cleaners, marble and ceramic cleaners, air freshener gels, liquid cleansers for dishes, automatic dishwasher detergents and rinses, toilet bowl disinfectant cleaners, bidet disinfectant cleaners, disinfectant hand soaps, and room deodorizers.

15. An aqueous personal care, household care, or fabric care composition comprising an effective amount of at least one copolymer of formula (II) according to claim 1 wherein the pH is from about 0.5 to about 7.

16. A method for the rheological modification of an aqueous personal care, household care, or fabric care composition wherein said method comprises adding to said personal care, household care, or fabric care composition an effective amount of a copolymer of formula (II) according to claim 1.

* * * * *